(12) United States Patent
Haskell-Luevano et al.

(10) Patent No.: US 10,899,793 B2
(45) Date of Patent: Jan. 26, 2021

(54) MELANOCORTIN LIGANDS AND METHODS OF USE THEREOF

(71) Applicants: REGENTS OF THE UNIVERSITY OF MINNESOTA, Minneapolis, MN (US); TORREY PINES INSTITUTE FOR MOLECULAR STUDIES, Port St. Lucie, FL (US)

(72) Inventors: Carrie Haskell-Luevano, Minneapolis, MN (US); Skye Ross Doering, Minneapolis, MN (US); Jon R. Appel, Port St. Lucie, FL (US); Marc A. Giulianotti, Port St. Lucie, FL (US); Richard A. Houghten, Port St. Lucie, FL (US); Clemencia Pinilla, Port St. Lucie, FL (US); Radleigh G. Santos, Port St. Lucie, FL (US)

(73) Assignees: Regents of the University of Minnesota, Minneapolis, MN (US); Torrey Pines Institute for Molecular Studies, Port St. Lucie, FL (US)

( * ) Notice: Subject to any disclaimer, the term of this patent is extended or adjusted under 35 U.S.C. 154(b) by 66 days.

(21) Appl. No.: 15/605,213

(22) Filed: May 25, 2017

(65) Prior Publication Data

US 2017/0342107 A1 Nov. 30, 2017

Related U.S. Application Data

(60) Provisional application No. 62/342,715, filed on May 27, 2016.

(51) Int. Cl.
| | | |
|---|---|---|
| *C07K 5/10* | (2006.01) | |
| *A61K 38/00* | (2006.01) | |
| *A61K 38/07* | (2006.01) | |
| *C07K 14/575* | (2006.01) | |

(52) U.S. Cl.
CPC ............ *C07K 5/1027* (2013.01); *A61K 38/00* (2013.01); *A61K 38/07* (2013.01); *C07K 5/10* (2013.01); *C07K 14/575* (2013.01)

(58) Field of Classification Search
CPC ...... A61K 38/00; A61K 38/07; C07K 5/1027; C07K 14/575; C07K 5/10
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,612,302 A | 9/1986 | Szabo et al. |
| 4,684,620 A | 8/1987 | Hruby et al. |
| 4,820,508 A | 4/1989 | Wortzman |
| 4,853,371 A | 8/1989 | Coy et al. |
| 4,938,949 A | 7/1990 | Borch et al. |
| 4,992,478 A | 2/1991 | Geria |
| 6,500,934 B1 | 12/2002 | Lerner et al. |
| 8,946,265 B2 | 2/2015 | Zhang et al. |
| 9,040,663 B2 | 5/2015 | Dodd et al. |
| 2004/0224901 A1 | 11/2004 | Chaturvedula et al. |
| 2011/0009341 A1 | 1/2011 | Sharma et al. |
| 2018/0118789 A1 | 5/2018 | Haskell-Luevano et al. |
| 2018/0360972 A1 | 12/2018 | Haskell-Luevano et al. |

FOREIGN PATENT DOCUMENTS

| | | |
|---|---|---|
| WO | 2002018437 A2 | 3/2002 |
| WO | 2003006604 A2 | 1/2003 |
| WO | 2011153817 A1 | 12/2011 |

OTHER PUBLICATIONS

Marcelo F. Masnnan, Synthesis & conformational analysis of his-phe-arg-trp-nh2 & analogues with antifungal properties, Bioorganic and Medicinal Chemistry (2006) 14, 7604-7614.*

Jerry Ryan Holder, Characterization of aliphatic, cyclic, and aromatic N-terminally "capped" His-D-Phe-Arg-Trp-NH2 tetrapeptides at the melanocortin receptors, European Journal of Pharmacology 462 (2003) 41-52.*

Houghten, et al., "Mixture-Based Synthetic Combinatorial Libraries", J. Med. Chem. 42(19), 3743-3778 (1999).

Houghten, et al., "Strategies for the Use of Mixture-Based Synthetic Combinatorial Libraries: Scaffold Ranking, Direct Testing In Vivo, and Enhanced Deconvolution by Computational Methods", J. Comb. Chem. 10(1), 3-19 (2008).

Hruby, et al., "Cyclic lactam .alpha.-melanotropin analogs of Ac-Nle4-cyclo[Asp5,D-Phe7,Lys10]-.alpha.-melanocyte-stimulating hormone-(4-10)-NH2 with bulky aromatic amino acids at position 7 show high antagonist potency and selectivity at specific melanocortin receptors", J. Med. Chem. 38(18), 3454-3461 (1995).

Hruby, et al., "α-Melanotropin: the minimal active sequence in the frog skin bioassay", J. Med. Chem. 30(11), 2126-2130 (1987).

Hunter, et al., "Preparation of Iodine-131 Labelled Human Growth Hormone of High Specific Activity", Nature 194(4827), 495-496 (1962).

Irani, et al., "Implication of the melanocortin-3 receptor in the regulation of food intake", Eur. J. Pharmacol. 660(1), 80-87 (2011).

Irani, et al., "Progress in the development of melanocortin receptor selective ligands", Current Pharmaceutical Design 10(28), 3443-3479 (2004).

Joseph, et al., "Chimeric NDP-MSH and MTII melanocortin peptides with agouti-related protein (AGRP) Arg-Phe-Phe amino acids possess agonist melanocortin receptor activity", Peptides 24(12), 1899-1908 (2003).

(Continued)

*Primary Examiner* — James H Alstrum-Acevedo
*Assistant Examiner* — Erinne R Dabkowski
(74) *Attorney, Agent, or Firm* — Viksnins Harris Padys Malen LLP

(57) ABSTRACT

Certain embodiments of the invention provide a compound of formula (I):

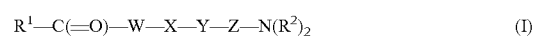

$$R^1-C(=O)-W-X-Y-Z-N(R^2)_2 \quad (I)$$

or a salt thereof, wherein $R^1$, $R^2$, W, X, Y and Z are as defined herein, as well as methods of use thereof.

20 Claims, 14 Drawing Sheets
Specification includes a Sequence Listing.

(56) References Cited

OTHER PUBLICATIONS

Joseph, et al., "Modified melanocortin tetrapeptide Ac-His-dPhe-Arg-Trp-NH at the arginine side chain with ureas and thioureas", J Pept Res 66(5), 297-307 (2005).

Joseph, et al., "Stereochemical Studies of the Monocyclic Agouti-Related Protein (103-122) Arg-Phe-Phe Residues: Conversion of a Melanocortin-4 Receptor Antagonist into an Agonist and Results in the Discovery of a Potent and Selective Melanocortin-1 Agonist", J. Met Chem. 47(27), 6702-6710 (2004).

Joseph, et al., "γ2-Melanocyte stimulation hormone (γ2-MSH) truncation studies results in the cautionary note that γ2-MSH is not selective for the mouse MC3R over the mouse MC5R", Peptides 31(12), 2304-2313 (2010).

Kavarana, et al., "Novel Cyclic Templates of α-MSH Give Highly Selective and Potent Antagonists/Agonists for Human Melanocortin-3/4 Receptors", J. Med. Chem. 45(12), 2644-2650 (2002).

Kiefer, et al., "Melanocortin Receptor Binding Determinants in the Agouti Protein", Biochemistry 37(4), 991-997 (1998).

Koikov, et al., "Sub-nanomolar hMC1R agonists by end-capping of the melanocortin tetrapeptide His-D-Phe-Arg-Trp-NH(2)", Bioorg. Med. Chem. Lett. 13(16), 2647-2650 (2003).

Lensing, et al., "Ac-Trp-DPhe(p-I)-Arg-Trp-NH2, a 250-Fold Selective Melanocortin-4 Receptor (MC4R) Antagonist over the Melanocortin-3 Receptor (MC3R), Affects Energy Homeostasis in Male and Female Mice Differently", ACS Chem. Neurosci., 1283-1291 (2016).

Mayorov, et al., "Solid-phase peptide head-to-side chain cyclodimerization: Discovery of C2-symmetric cyclic lactam hybrid α-melanocyte-stimulating hormone (MSH)/agouti-signaling protein (ASIP) analogues with potent activities at the human melanocortin receptors", Peptides 31(10), 1894-1905 (2010).

Miller, et al., "Cloning of the mouse agouti gene predicts a secreted protein ubiquitously expressed in mice carrying the lethal yellow mutation", Genes. Dev. 7(3), 454-467 (1993).

Mo, et al., "Activation of MAPK by inverse agonists in six naturally occurring constitutively active mutant human melanocortin-4 receptors", Biochim. Biophys. Acta. 1832(12) 1939-1948 (2013).

Mountjoy, et al., "Localization of the melanocortin-4 receptor (MC4-R) in neuroendocrine and autonomic control circuits in the brain", Mol. Endocrinol. 8(10), 1298-1308 (1994).

Mountjoy, et al., "The cloning of a family of genes that encode the melanocortin receptors", Science 257(5074), 1248-1251 (1992).

Mutulis, et al., "Reductive amination products containing naphthalene and indole moieties bind to melanocortin receptors", Bioorg. Med. Chem. Lett. 12(7), 1035-1038 (2002).

Nakanishi, et al., "Nucleotide sequence of cloned cDNA for bovine corticotropin-beta-lipotropin precursor", Nature 278(5703), 423-427 (1979).

Ni, et al., "Central receptors mediating the cardiovascular actions of melanocyte stimulating hormones", J. Hypertens. 24(11), 2239-2246 (2006).

Ollmann, et al., "Antagonism of Central Melanocortin Receptors in Vitro and in Vivo by Agouti-Related Protein", Science 278(5335), 135-138 (1997).

Ostresh, et al., "Peptide libraries: Determination of relative reaction rates of protected amino acids in competitive couplings", Biopolymers 34(12), 1681-1689 (1994).

Otsuka, et al., "Synthesis of peptides related to the N-terminal structure of corticotropin. III. The synthesis of L-histidyl-L-phenylalanyl-L-tryptophan, the smallest peptideexhibiting the melanocyte-stimulating and the lipolytic activities", Bull. Chem. Soc. Jpn. 37(10), 1465-1471 (1964).

Pinilla, et al., "Advances in the use of synthetic combinatorial chemistry: mixture-based libraries", Nat. Med. 9(1), 118-122 (2003).

Pinilla, et al., "Rapid identification of high affinity peptide ligands using positional scanning synthetic peptide combinatorial libraries", BioTechniques 13(6), 901-905 (1992).

Proneth, et al., "Melanocortin Tetrapeptide Ac-His-DPhe-Arg-Trp-NH2 Modified at the Para Position of the Benzyl Side Chain (DPhe): Importance for Mouse Melanocortin-3 Receptor Agonist versus Antagonist Activity", J. Med. Chem. 51(18), 5585-5593 (2008).

Roselli-Rehfuss, et al., "Identification of a receptor for gamma melanotropin and other proopiomelanocortin peptides in the hypothalamus and limbic system", Proc. Natl. Acad. Sci. U.S.A. 90(19), 8856-8860 (1993).

Santos, et al., "Use and Implications of the Harmonic Mean Model on Mixtures for Basic Research and Drug Discovery", ACS Comb. Sci. 13(3), 337-344 (2011).

Sawyer, et al., "4-Norleucine, 7-D-phenylalanine-α-melanocyte-stimulating Hormone: A Highly Potent α-melanotropin with Ultralong Biological Activity", Proc. Natl. Acad. Sci. U.S.A. 77(10), 5754-5758 (1980).

Schild, "pA, A New Scale for the Measurement of Drug Antagonism", British Journal of Pharmacology 2(3), 189-206 (1947).

Schiöth, et al., "Major pharmacological distinction of the ACTH receptor from other melanocortin receptors", Life Sci. 59(10), 797-801 (1996).

Singh, et al., "Synthesis and pharmacology of α/β3-peptides based on the melanocortin agonist Ac-His-d Phe-Arg-Trp-NH2 sequence", A.C.S. Med. Chem. Lett. 6(5) 568-572 (2015).

Tala, et al., "Microwave-assisted solid-phase synthesis of side-chain to side-chain lactam-bridge cyclic peptides", Bioorg. Med. Chem. Lett. 25(24), 5708-5711 (2015).

Tam, et al., "An SN2 deprotection of synthetic peptides with a low concentration of hydrofluoric acid in dimethyl sulfide: evidence and application in peptide synthesis", J. Am. Chem. Soc. 105(21), 6442-6455 (1983).

Todorovic, et al., "N-Terminal Fatty Acylated His-dPhe-Arg-Trp-NH2 Tetrapeptides: Influence of Fatty Acid Chain Length on Potency and Selectivity at the Mouse Melanocortin Receptors and Human Melanocytes", J. Med. Chem. 48(9), 3328-3336 (2005).

Todorovic, et al., "Synthesis and activity of the melanocortin Xaa-d-Phe-Arg-Trp-NH tetrapeptides with amide bond modifications", The journal of peptide research: official journal of the American Peptide Society 63(3), 270-278 (2004).

Tota, et al., "Molecular Interaction of Agouti Protein and Agouti-Related Protein with Human Melanocortin Receptors", Biochemistry 38(3), 897-904 (1999).

Van Der Ploeg, et al., "A role for the melanocortin 4 receptor in sexual function", Proc. Natl. Acad. Sci. U.S.A. 99(17), 11381-11386 (2002).

Weeden, et al., "A retro-inverso α-melanocyte stimulating hormone analog with MC1R-binding selectivity", J. Pept. Sci. 17(1), 47-55 (2011).

Wessells, et al., "Synthetic melanotropic peptide initiates erections in men with psychogenic erectile dysfunction: double-blind, placebo controlled crossover study", J. Urol. 160(2), 389-393 (1998).

Wilczynski, et al., "Identification of Putative Agouti-Related Protein(87-132)-Melanocortin-4 Receptor Interactions by Homology Molecular Modeling and Validation Using Chimeric Peptide Ligands", J. Med. Chem. 47(9), 2194-2207 (2004).

Ye, et al., "Structure-activity relationship of linear tetrapeptides Tic-DPhe-Arg-Trp-NH2 at the human melanocortin-4 receptor and effects on feeding behaviors in rat", Peptides 26(10), 2017-2025 (2005).

Atalayer, et al., "Food demand and meal size in mice with single or combined disruption of melanocortin type 3 and 4 receptors", Am. J. Physiol. Intergr. Comp. Physiol. 298(6), R1667-R1674 (2010).

Ballet, et al., "Novel selective human melanocortin-3 receptor ligands: Use of the 4-amino-1,2,4,5-tetrahydro-2-benzazepin-3-one (Aba) scaffold", Bioorg. Med. Chem. Lett. 17(9), 2492-2498 (2007).

Boeglin, et al., "Aza-scanning of the Potent Melanocortin Receptor Agonist Ac-His-d-Phe-Arg-Trp-NH2", Chem Biol Drug Des 67(4), 275-283 (2006).

Büch, et al., "Pertussis Toxin-sensitive Signaling of Melanocortin-4 Receptors in Hypothalamic GT1-7 Cells Defines Agouti-related Protein as a Biased Agonist", J. Biol. Chem. 284(39), 26411-26420 (2009).

Bultman, et al., "Molecular characterization of the mouse agouti locus", Cell 71(7), 1195-1204 (1992).

(56) References Cited

OTHER PUBLICATIONS

Carotenuto, et al., "Discovery of Novel Potent and Selective Agonists at the Melanocortin-3 Receptor", J. Med. Chem. 58(24), 9773-9778 (2015).
Chen, et al., "A Colorimetric Assay for Measuring Activation of Gs- and Gq-Coupled Signaling Pathways", Anal. Biochem. 226(2), 349-354 (1995).
Chen, et al., "Calcium phosphate-mediated gene transfer: a highly efficient transfection system for stably transforming cells with plasmid DNA", BioTechniques 6(7), 632-638 (1988).
Chen, et al., "Exocrine Gland Dysfunction in MC5-R-Deficient Mice: Evidence for Coordinated Regulation of Exocrine Gland Function by Melanocortin Peptides", Cell 91(6), 789-798 (1997).
Cheung, et al., "Structure-Activity relationship of linear peptide Bu-His-DPhe-Arg-Trp-Gly-NH2 at the human melanocortin-1 and -4 receptors: arginine substitution", Bioorg. Med. Chem. Lett. 12(17), 2407-2410 (2002).
Chhajlani, et al., "Molecular cloning and expression of the human melanocyte stimulating hormone receptor eDNA", FEBS Lett 309(3), 417-420 (1992).
Chorev, et al., "A dozen years of retro-inverso peptidomimetics", Acc. Chem. Res. 26(5), 266-273 (1993).
Chorev, et al., "Partially modified retro-inverso-enkephalinamides: topochemical long-acting analogs in vitro and in vivo", Science 204(4398), 1210-1212 (1979).
Danho, et al., "Structure-Activity relationship of linear peptide Bu-His6-DPhe7-Arg8-Trp9-Gly10-NH2 at the human melanocortin-1 and -4 receptors: DPhe7 and Trp9 substitution", Bioorg. Med. Chem. Lett. 13(4), 649-652 (2003).
Day, et al., "Small molecule-mediated disruption of Wnt-dependent signaling in tissue regeneration and cancer", Nat Chem Biol 5(10), 749-757 (2009).
Doering, et al., "Discovery of Mixed Pharmacology Melanocortin-3 Agonists and Melanocortin-4 Receptor Tetrapeptide Antagonist Compounds (TACOs) Based on the Sequence Ac-Xaa1-Arg-(pI)DPhe-Xaa4-NH2", J Med Chem 60(10), 4342-4357 (2017).
Doering, et al., "Melanocortin Antagonist Tetrapeptides with Minimal Agonist Activity at the Mouse Melanocortin-3 Receptor", A.C.S. Med. Chem. Lett. 6(2), 123-127 (2015).
Dooley, et al., "Selective Ligands for the μ, δ, and κ Opioid Receptors Identified from a Single Mixture Based Tetrapeptide Positional Scanning Combinatorial Library", J. Biol. Chem. 273(30), 18848-18856 (1998).
Dooley, et al., "The use of positional scanning synthetic peptide combinatorial libraries for the rapid determination of opioid receptor ligands", Life Sci. 52(18), 1509-1517 (1993).
Ericson, et al., "A fragment of the *Escherichia coli* ClpB heat-shock protein is a micromolar melanocortin 1 receptor agonist", Bioorg. Med. Chem. Lett. 25(22), 5306-5308 (2015).
Ericson, et al., "Discovery of a β-Hairpin Octapeptide, c[Pro-Arg-Phe-Phe-Dap-Ala-Phe-DPro], Mimetic of Agouti-Related Protein(87-132)[Agrp(87-132)] with Equipotent Mouse Melanocortin-4 Receptor (mMC4R) Antagonist Pharmacology", J. Med. Chem. 58(11), 4638-4647 (2015).
Fan, et al., "Role of melanocortinergic neurons in feeding and the agouti obesity syndrome", Nature 385(6612), 165-168 (1997).
Farooqi, et al., "Clinical Spectrum of Obesity and Mutations in the Melanocortin 4 Receptor Gene", N. Engl. J. Med. 348(12), 1085-1095 (2003).
Fields, et al., "Solid phase peptide synthesis utilizing 9-fluorenylmethoxycarbonyl amino acids", Int. J. Pept. Protein Res. 35(3), 161-214 (1990).
Finan, et al., "A rationally designed monomeric peptide triagonist corrects obesity and diabetes in rodents", Nat. Med. 21(1), 27-36 (2015).
Finan, et al., "Unimolecular Dual Incretins Maximize Metabolic Benefits in Rodents, Monkeys, and Humans", Science Translational Medicine 5(209), 209ra151-209ra151 (2013).
Gantz, et al., "Molecular cloning of a novel melanocortin receptor", J. Biol. Chem. 268(11), 8246-8250 (1993).
Gantz, et al., "Molecular cloning, expression, and characterization of a fifth melanocortin receptor", Biochem. Biophys. Res. Commun. 200(3), 1214-1220 (1994).
Gantz, et al., "Molecular cloning, expression, and gene localization of a fourth melanocortin receptor", J. Biol. Chem. 268(20), 15174-15179 (1993).
Ghamari-Langroudi, et al., "G-protein-independent coupling of MC4R to Kir7.1 in hypothalamic neurons", Nature 520(7545), 94-98 (2015).
Goodman, et al., "On the concept of linear modified retro-peptide structures", Acc. Chem. Res. 12(1), 1-7 (1979).
Greenfield, et al., "Modulation of Blood Pressure by Central Melanocortinergic Pathways", New England Jounral of Medicine 360, 44-52 (2009).
Grieco, et al., "D-Amino acid scan of gamma-melanocyte-stimulating hormone: importance of Trp(8) on human MC3 receptor selectivity", J. Med. Chem. 43(26), 4998-5002 (2000).
Grieco, et al., "Further structure-activity studies of lactam derivatives of MT-II and SHU-9119: Their activity and selectivity at human melanocortin receptors 3, 4 and 5", Peptides 28(6), 1191-1196 (2007).
Grieco, et al., "Structure-Activity Studies of the Melanocortin Peptides: Discovery of Potent and Selective Affinity Antagonists for the hMC3 and hMC4 Receptors", J. Med. Chem. 45(24), 5287-5294 (2002).
Hadley, "Discovery that a melanocortin regulates sexual functions in male and female humans", Peptides 26(10), 1687-1689 (2005).
Hano, et al., "Evaluation of the physiological properties of d-histidyl-d-phenylalanyl-d-arginyl-d-tryptophyl-glycine in frog melanocyte", Biochimica et Biophysica Acta 9BBA)—General Subjects 90(1), 201-204 (1964).
Haskell-Luevano, et al., "Characterization of Melanocortin NDP-MSH Agonist Peptide Fragments at the Mouse Central and Peripheral Melanocortin Receptors", J. Med. Chem. 44(13), 2247-2252 (2001).
Haskell-Luevano, et al., "Discovery of Prototype Peptidomimetic Agonists at the Human Melanocortin Receptors MC1R and MC4R", J. Med. Chem. 40(14), 2133-2139 (1997).
Haskell-Luevano, et al., "Structure Activity Studies of the Melanocortin-4 Receptor by in Vitro Mutagenesis: Identification of Agouti-Related Protein (AGRP), Melanocortin Agonist and Synthetic Peptide Antagonist Interaction Determinants", Biochemistry 40(20), 6164-6179 (2001).
Haskell-Luevano, et al., "Truncation studies of alpha-melanotropin peptides identify tripeptide analogues exhibiting prolonged agonist bioactivity", Peptides 17(6), 995-1002 (1996).
Haslach, et al., "Identification of Tetrapeptides from a Mixture Based Positional Scanning Library That Can Restore hM Full Agonist Function of the L106P, I69T, I102S, A219V, C271Y, and C271R Human Melanocortin-4 Polymorphic Receptors (hMC4Rs)", J. Med. Chem. 57(11), 4615-4628 (2014).
Haynes, "The activation of adrenal phosphorylase by the adrenocorticotropic hormone", J. Biol. Chem 233(5), 1220-1222 (1958).
Holder, et al., "Design and pharmacology of peptoids and peptide-peptoid hybrids based on the melanocortin agonists core tetrapeptide sequence", Bioorg. Med. Chem. Lett. 13(24), 4505-4509 (2003).
Holder, et al., "Structure-Activity Relationships of the Melanocortin Tetrapeptide Ac-His-DPhe-Arg-Trp-NH2 at the Mouse Melanocortin Receptors. 1. Modifications at the His Position", J. Med. Chem. 45(13), 2801-2810 (2002).
Holder, et al., "Structure-Activity Relationships of the Melanocortin Tetrapeptide Ac-His-d-Phe-Arg-Trp-NH2 at the Mouse Melanocortin Receptors. 4. Modifications at the Trp Position", J. Med. Chem. 45(26), 5736-5744 (2002).
Holder, et al., "Structure-Activity Relationships of the Melanocortin Tetrapeptide Ac-His-DPhe-Arg-Trp-NH2 at the Mouse Melanocortin Receptors: Part 2 Modifications at the Phe Position", Med. Chem. 45(14), 3073-3081 (2002).
Holder, et al., "Structure-activity relationships of the melanocortin tetrapeptide Ac-His-DPhe-Arg-Trp-NH2 at the mouse melanocortin receptors. Part 3: modifications at the Arg position", Peptides 24(1), 73-82 (2003).

(56) References Cited

OTHER PUBLICATIONS

Houghten, "General method for the rapid solid-phase synthesis of large numbers of peptides: specificity of antigen-antibody interaction at the level of individual amino acids", Proc. Natl. Acad. Sci. U.S.A 82(15), 5131-5135 (1985).
Houghten, et al., "Generation and use of synthetic peptide combinatorial libraries for basic research and drug discovery", Int. J. Pept. Protein Res. 27(6), 673-678 (1986).
Akgun, et al., "Inhibition of Inflammatory and Neuropathic Pain by Targeting a Mu Opioid Receptor/Chemokine Receptor5 Heteromer (MOR-CCR5).", J Med Chem 58(21), 8647-8657 (2015).
Albizu, et al., "Time-resolved FRET between GPCR ligands reveals oligomers in native tissues.", Nat Chem Biol 6(8), 587-594 (2010).
Allen, "The Results of Extirpation of the Anterior Lobe of the Hypophysis and of the Thyroid of Rana Pipiens Larvae", Science 44, 755-758 (1916).
Altschul, et al., "Basic local alignment search tool.", J Mol Biol 215, 403-410 (1990).
Altschul, et al., "Gapped BLAST and PSI-BLAST: a new generation of protein database search programs.", Nucleic Acids Res 25(17), 3389-3402 (1997).
Barkey, et al., "Development of melanoma-targeted polymer micelles by conjugation of a Melanocortin 1 Receptor (MC1R) specific ligand.", J Med Chem 54, 8078-8084 (2011).
Barnea, et al., "The genetic design of signaling cascades to record receptor activation.", PNAS 105(1), 64-69 (2008).
Barrett, et al., "Neonatal melanocortin receptor agonist treatment reduces play fighting and promotes adult attachment in prairie voles in a sex-dependent manner.", Neuropharmacology 85, 357-366 (2014).
Bolin, et al., "NMR structure of a minimized human agouti related protein prepared by total chemical synthesis.", FEBS Lett 451, 125-131 (1999).
Bowen, et al., "Design, Synthesis, and Validation of a Branched Flexible Linker for Bioactive Peptides.", J Org Chem 72(5), 1675-1680 (2007).
Brabez, et al., "Design, synthesis and biological studies of efficient multivalent melanotropin ligands: tools towards melanoma diagnosis and treatment.", J Med Chem 54(20), 7375-7384 (2011).
Brabez, et al., "Multivalent Interactions: Synthesis and Evaluation of Melanotropin Multimers—Tools for Melanoma Targeting.", ACS Med Chem Lett 4, 98-102 (2013).
Breit, et al., "Alternative G protein-coupling and biased agonism: new insights into melanocortin-4 receptor signalling", Mol Cell Endocrinol 331, 232-240 (2010).
Brock, et al., "Activation of a Dimeric Metabotropic Glutamate Receptor by Intersubunit Rearrangement.", J Biol Chem 282, 33000-33008 (2007).
Broussard, et al., "Fluorescence resonance energy transfer microscopy as demonstrated by measuring the activation of the serine/threonine kinase Akt.", Nat Protoc 8(2), 265-281 (2013).
Brown, et al., "Central injection in rats of a-melanocyte-stimulating hormone analog: effects on food intake and brain Fos.", Regul Peptides 78, 89-94 (1998).
Butler, et al., "A unique metabolic syndrome causes obesity in the melanocortin-3 receptor-deficient mouse.", Endocrinol 141(9), 3518-3521 (2000).
Cai, et al., "Cell Signaling and Trafficking of Human Melanocortin Receptors in Real Time Using Two-photon Fluorescence and Confocal Laser Microscopy: Differentiation of Agonists and Antagonists.", Chem Biol Drug Des 68(4), 183-193 (2006).
Carpino, et al., "The 9-Fluorenylmethoxycarbonyl Amino-Protecting Group.", J Org Chem 37(22), 3404-3409 (1972).
Carpino, et al., "The 9-Fluorenylmethoxycarbonyl Function, a New Base-Sensitive Amino-Protecting Group.", J Am Chem Soc 92, 5748-5749 (1970).
Carrithers, et al., "Synthesis and characterization of bivalent peptide ligands targeted to G-protein-coupled receptors.", Chemistry & Biology 3(7), 537-542 (1996).

Casado, et al., "Old and new ways to calculate the affinity of agonists and antagonists interacting with G-protein-coupled monomeric and dimeric receptors: The receptor-dimer cooperativity index.", Pharmacol Ther 116, 343-354 (2007).
Chapman, et al., "The melanocortin 4 receptor: Oligomer formation, interaction sites and functional significance.", Biochim Biophys Acta 1828, 535-542 (2013).
Chen, et al., "Functional characterization of the modified melanocortin peptides responsible for ligand selectivity at the human melanocortin receptors.", Peptides 27, 2836-2845 (2006).
Chen, et al., "Inactivation of the mouse melanocortin-3 receptor results in increased fat mass and reduced lean body mass.", Nat Genet 26, 97-102 (2000).
Chhajlani, et al., "Molecular cloning of a novel human melanocortin receptor.", Biochem Biophys Res Commun 195, 866-873 (1993).
Christensen, "A Qualitative Test for Monitoring Coupling Completeness in Solid Phase Peptide Synthesis Using Chloranil.", Acta Chemica Scandinavica B 33, 763-766 (1979).
Clayton, et al., "Bremelanotide for female sexual dysfunctions in premenopausal women: a randomized, placebo-controlled dose-finding trial.", Women's Health 12, 325-337 (2016).
Comps-Agrar, et al., "The oligomeric state sets GABAB receptor signalling efficacy.", EMBO J 30, 2336-2349 (2011).
Corpet, et al., "Multiple sequence alignment with hierarchical clustering.", Nucl Acids Res 16, 10881-10890 (1988).
Cottet, et al., "BRET and time-resolved FRET strategy to study GPCR oligomerization: from cell lines toward native tissues.", Front Endocrinol 3, 92 (2012).
Damian, et al., "Asymmetric conformational changes in a GPCR dimer controlled by G-proteins.", EMBO J 25(24), 5693-5702 (2006).
Danho, "Highly Selective Cyclic Peptides for Human Melanocortin-4 Receptor (MC-4 R): Design, Synthesis, Bioactive Conformation, and Pharmacological Evaluation as an Anti-Obesity Agent", Peptides: The Wave of the Future, 701-703 (2001).
Daniels, et al., "Opioid-induced tolerance and dependence in mice is modulated by the distance between pharmacophores in a bivalent ligand series.", Proc Natl Acad Sci 102(52), 19208-19213 (2005).
Deboer, et al., "Cachexia: lessons from melanocortin antagonism.", Trends Endocrinol Metab 17, 199-204 (2006).
Dehigaspitiya, et al., "Linear scaffolds for multivalent targeting of melanocortin receptors.", Org Biomol Chem 13, 11507-11517 (2015).
Dehigaspitiya, et al., "Synthesis and bioactivity of MSH4 oligomers prepared by an A2 + B2 strategy.", Tetrahedron Lett 56(23), 3060-3065 (2015).
Doering, "Discovery of Peptide and Peptidomimetic Based Ligands Targeting the Melanocortin Receptors: A campaign in mixture-based positional scanning, chemical topology, and structure-activity relationships", Dissertation Submitted to the Faculty of the University of Minnesota, in Partial Fulfillment of the Requirements for the Degree of Doctor of Philosophy, 181 pages (Jul. 2016).
Durroux, "Principles: A model for the allosteric interactions between ligand binding sites within a dimeric GPCR.", Trends Pharmacol Sci 26, 376-384 (2005).
Ebihara, et al., "Involvement of Agouti-Related Protein, an Endogenous Antagonist of Hypothalamic Melanocortin Receptor, in Leptin Action.", Diabetes 48, 2028-2033 (1999).
Echalier, et al., "Heating and microwave assisted SPPS of C-terminal acid peptides on trityl resin: the truth behind the yield.", Amino Acids 45, 1395-1403 (2013).
Ellacott, et al., "Assessment of feeding behavior in laboratory mice.", Cell Metab 12(1), 10-17 (2010).
Elshan, et al., "Trigonal scaffolds for multivalent targeting of melanocortin receptors.", Org Biomol Chem 13(6), 1778-1791 (2015).
Elster, et al., "Bioluminescence Resonance Energy Transfer as a Screening Assay: Focus on Partial and Inverse Agonism.", J Biomol Screen 12, 41-49 (2007).
Emmerson, "Melanocortin-4 receptor agonists for the treatment of obesity", Current Topics in Medicinal Chemistry 7(11), 1121-1130 (2007).

(56) References Cited

OTHER PUBLICATIONS

Erez, et al., "Narcotic Antagonistic Potency of Bivalent Ligands Which Contain β-Naltrexamine. Evidence for Bridging between Proximal Recognition Sites.", J Med Chem 25, 847-849 (1982).
Ericson, et al., "A Macrocyclic Agouti-Related Protein/[Nle4, DPhe7]α-Melanocyte Stimulating Hormone Chimeric Scaffold Produces Subnanomolar Melanocortin Receptor Ligands", J Med Chem 60(2), 805-813 (2017).
Ericson, et al., "Bench-top to clinical therapies: A review of melanocortin ligands from 1954 to 2016.", Biochim Biophys Acta Mol Basis Dis 1863, 2414-2435 (2017).
Fernandes, et al., "Synthesis and evaluation of bivalent ligands for binding to the human melanocortin-4 receptor.", Bioorg Med Chem 22, 6360-6365 (2014).
Ferre, "G Protein-Coupled Receptor Oligomerization Revisited: Functional and Pharmacological Perspectives.", Pharmacol Rev 66, 413-434 (2014).
Ferre, et al., "The GPCR Heterotetramer: Challenging Classical Pharmacology.", Trends Pharmacol Sci 36(3), 145-152 (2015).
Filpula, et al., "Releasable PEGylation of proteins with customized linkers.", Advanced Drug Delivery 60, 29-49 (2008).
Gao, et al., "Agonist-Dependent Internalization of the Human Melanocortin-4 Receptors in Human Embryonic Kidney 293 Cells.", J Pharmacol Exp Ther 307, 870-877 (2003).
Giuliani, et al., "Melanocortins protect against progression of Alzheimer's disease in tripletransgenic mice by targeting multiple pathophysiological pathways.", Neurobiol Aging 35, 537-547 (2014).
Giuliani, et al., "NDP-α-MSH induces intense neurogenesis and cognitive recovery in Alzheimer transgenic mice through activation of melanocortin MC4 receptors.", Mol Cell Neurosci 67, 13-21 (2015).
Gracia, et al., "Homodimerization of adenosine A1 receptors in brain cortex explains the biphasic effects of caffeine.", Neuropharmacology 71, 56-69 (2013).
Grant, et al., "Agonist-dependent Dissociation of Human Somatostatin Receptor 2 Dimers.", J Biol Chem 279(35), 36179-36183 (2004).
Griffon, et al., "Molecular cloning and characterization of the rat fifth melanocortin receptor.", Biochem Biophys Res Commun 200(2), 1007-1014 (1994).
Hahn, et al., "Coexpression of Agrp and NPY in fasting-activated hypothalamic neurons.", Nat Neurosci 1, 271-272 (1998).
Han, et al., "Allosteric communication between protomers of dopamine Class A GPCR dimers modulates activation.", Nat Chem Biol 5, 688-695 (2009).
Handl, et al., "Synthesis and Evaluation of Bivalent NDP-α-MSH(7) Peptide Ligands for Binding to the Human Melanocortin Receptor 4 (hMC4R).", Bioconjug Chem 18(4), 1101-1109 (2007).
Haskell-Luevano, et al., "Characterization of the Neuroanatomical Distribution of Agouti-Related Protein Immunoreactivity in the Rhesus Monkey and the Rat.", Endocrinology 140, 1408-1415 (1999).
Haynes, et al., "Studies on the mechanism of action of the adrenocorticotropic hormone.", J Biol Chem 225, 115-124 (1957).
Hess, et al., "Backbone cyclic peptidomimetic melanocortin-4 receptor agonist as a novel orally administrated drug lead for treating obesity", J Med Chem 51(4), 1026-1034 (2008).
Higgins, et al., "CLUSTAL: a package for performing multiple sequence alignment on a microcomputer.", Gene 73(1), 237-244 (1988).
Higgins, et al., "Fast and sensitive multiple sequence alignments on a microcomputer.", CABIOS 5(2), 151-153 (1989).
Hiller, et al., "Class A G-Protein-Coupled Receptor (GPCR) Dimers and Bivalent Ligands.", J Med Chem 56, 6542-6559 (2013).
Hlavackova, et al., "Evidence for a single heptahelical domain being turned on upon activation of a dimeric GPCR.", EMBO J 24, 499-509 (2005).
Huang, et al., "Parallelization of a local similarity algorithm.", CABIOS 8(2), 155-165 (1992).
Huszar, et al., "Targeted disruption of the melanocortin-4 receptor results in obesity in mice.", Cell 88(1), 131-141 (1997).
Iglesias, et al., "Serotonin-2A homodimers are needed for signalling via both phospholipase A2 and phospholipase C in transfected CHO cells.", Eur J Pharmacol 800, 63-69 (2017).
Jackson, et al., "Chimeras of the agouti-related protein: Insights into agonist and antagonist selectivity of melanocortin receptors.", Peptides 26, 1978-1987 (2005).
Jackson, et al., "Design, Pharmacology, and NMR Structure of a Minimized Cystine Knot with Agouti-Related Protein Activity.", Biochemistry 41, 7565-7572 (2002).
Jagadish, et al., "Squalene-derived Flexible Linkers for Bioactive Peptides.", Bioorg Med Chem Lett 17(12), 3310-3313 (2007).
Joppa, et al., "Central administration of peptide and small molecule MC4 receptor antagonists induce hyperphagia in mice and attenuate cytokine-induced anorexia.", Peptides 26, 2294-2301 (2005).
Josan, et al., "Cell-Specific Targeting by Heterobivalent Ligands.", Bioconjugate Chem 22(7), 1270-1278 (2011).
Josan, et al., "Solid-Phase Synthesis of Heterobivalent Ligands Targeted to Melanocortin and Cholecystokinin Receptors.", Int J Pept Res Ther 14, 293-300 (2008).
Journe, et al., "N1-linked melatonin dimers as bivalent ligands targeting dimeric melatonin receptors.", Medchemcomm 5, 792-796 (2014).
Kaiser, et al., "Color test for detection of free terminal amino groups in the solid-phase synthesis of peptides.", Anal Biochem 34(2), 595-598 (1970).
Karlin, et al., "Applications and statistics for multiple high-scoring segments in molecular sequences.", Proc Natl Acad Sci 90, 5873-5877 (1993).
Karlin, et al., "Methods for assessing the statistical significance of molecular sequence features by using general scoring schemes.", Proc Natl Acad Sci 87(6), 2264-2268 (1990).
Kingsberg, "Bremelanotide for Hypoactive Sexual Desire Disorder: Analyses from a Phase 2B Does-Ranging Study", 4th International Consultation on Sexual Medicine, J Sex Med 12(suppl 6), 389 (2015).
Kniazeff, et al., "Closed state of both binding domains of homodimeric mGlu receptors is required for full activity.", Nat Struct Mol Biol 11, 706-713 (2004).
Kniazeff, et al., "Locking the Dimeric GABAB G-Protein-Coupled Receptor in Its Active State.", J Neurosci 24, 370-377 (2004).
Kopanchuk, et al., "Co-operative regulation of ligand binding to melanocortin receptor subtypes: evidence for interacting binding sites", Eur J Pharmacol 512, 85-95 (2005).
Kopanchuk, et al., "Kinetic evidence for tandemly arranged ligand binding sites in melanocortin 4 receptor complexes.", Neurochem Int 49, 533-542 (2006).
Kroeze, et al., "PRESTO-TANGO: an open-source resource for interrogation of the druggable human GPCR-ome.", Nat Struct Mol Biol 22, 362-369 (2015).
Kuhhorn, et al., "Development of a Bivalent Dopamine D2 Receptor Agonist.", J Med Chem 54, 7911-7919 (2011).
Langendonk, et al., "Afamelanotide for Erythropoietic Protoporphyria.", N Engl J Med 373, 48-59 (2015).
Le Naour, et al., "Bivalent Ligands That Target μ Opioid (MOP) and Cannabinoid1 (CB1) Receptors Are Potent Analgesics Devoid of Tolerance.", J Med Chem 56(13), 5505-5513 (2013).
Le Naour, et al., "Putative Kappa Opioid Heteromers as Targets for Developing Analgesics Free of Adverse Effects.", J Med Chem 57, 6383-6392 (2014).
Lensing, et al., "A Direct In Vivo Comparison of the Melanocortin Monovalent Agonist Ac-His-DPhe-Arg-Trp-NH2 versus the Bivalent Agonist Ac-His-DPhe-Arg-Trp-PEDG20-His-DPhe-Arg-Trp-NH2: A Bivalent Advantage.", ACS Chem Neurosci 8(6), 1262-1278 (2017).
Lensing, et al., "An in vitro and in vivo investigation of bivalent ligands that display preferential binding and functional activity for different melanocortin receptor homodimers.", J Med Chem 59, 3112-3128 (2016).
Lensing, et al., "Bivalent Ligands as Pharmacological Probes for the Melanocortin Receptors: The Bivalent Advantage", Dissertation submitted to the Faculty of University of Minnesota in Partial

(56) References Cited

OTHER PUBLICATIONS

Fulfillment of the Requirements for the Degree of Doctor of Philosophy, 327 pages, May 2017.
Lensing, et al., "Developing a Biased Unmatched Bivalent Ligand (BUmBL) Design Strategy to Target the GPCR Homodimer Allosteric Signaling (cAMP over β-Arrestin 2 Recruitment) Within the Melanocortin Receptors.", J Med Chem, Just Accepted (2018).
Lensing, et al., "The Ac-Trp-DPhe(p-I)-Arg-Trp-NH2 250-Fold Selective Melanocortin-4 Receptor (MC4R) Antagonist over the Melanocortin-3 Receptor (MC3R) Affects Energy Homeostasis in Male and Female Mice Differently.", ACS Chem Neurosci 7(9), 1283-1291 (2016).
Lu, et al., "Agouti protein is an antagonist of the melanocyte-stimulating-hormone receptor.", Nature 371(6500), 799-802 (1994).
Mandrika, et al., "Melanocortin receptors form constitutive homo- and heterodimers.", Biochem Biophys Res Commun 326, 349-354 (2005).
Marsh, et al., "Effects of neuropeptide Y deficiency on hypothalamic agouti-related protein expression and responsiveness to melanocortin analogues.", Brain Research 848, 66-77 (1999).
Marsh, et al., "Response of melanocortin-4 receptor-deficient mice to anorectic and orexigenic peptides.", Nat Genet 21, 119-122 (1999).
Marti-Solano, et al., "Drugging specific conformational states of GPCRs: challenges and opportunities for computational chemistry", Drug Discovery Today 21, 625-631 (2016).
Marvyn, et al., "Data onoxygenconsumptionrate,respiratory exchangeratio,andmovementinC57BL/6J female miceonthethirddayofconsuming a high-fatdiet.", Data in Brief 7, 472-475 (2016).
Mcnulty, et al., "High-Resolution NMR Structure of the Chemically-Synthesized Melanocortin Receptor Binding Domain AGRP(87-132) of the Agouti-Related Protein", Biochemistry 40, 15520-15527 (2001).
Merrifield, et al., "Solid Phase Peptide Synthesis. I. The Synthesis of a Tetrapeptide", JACS 85, 2149-2154 (1963).
Myers, et al., "Optimal alignments in linear space", CABIOS 4(1), 11-17 (1988).
Needleman, et al., "A General Method Applicable to the Search for Similarities in the Amino Acid Sequence of Two Proteins.", J Mol Biol 48, 443-453 (1970).
Nickolls, et al., "Dimerization of the melanocortin 4 receptor: A study using bioluminescence resonance energy transfer.", Peptides 27, 380-387 (2006).
Nickolls, et al., "Functional Selectivity of Melanocortin 4 Receptor Peptide and Nonpeptide Agonists: Evidence for Ligand-Specific Conformational States", J Pharmacol Exp Ther 313, 1281-1288 (2005).
Odagami, "Design of cyclic peptides with agonist activity at melanocortin receptor-4", Bioorg Med Chem Lett 16(14), 3723-3726 (2006).
Orcel, et al., "Differential Coupling of the Vasopressin V1b Receptor through Compartmentalization within the Plasma Membrane.", Mol Pharmacol 75, 637-647 (2009).
Pearson, et al., "Improved tools for biological sequence comparison.", Proc Natl Acad Sci 85, 2444-2448 (1988).
Pearson, et al., "Using the FASTA program to search protein and DNA sequence databases.", Meth Mol Biol 24, 307-331 (1994).
Pellissier, et al., "G Protein Activation by Serotonin Type 4 Receptor Dimers.", J Biol Chem 286, 9985-9997 (2011).
Penagarikano, et al., "Exogenous and evoked oxytocin restores social behavior in the Cntnap2 mouse model of autism.", Sci Transl Med 7(271), 271ra8 (2015).
Pfleger, et al., "Bioluminescence resonance energy transfer (BRET) for the real-time detection of protein-protein interactions.", Nat Protoc 1(1), 337-345 (2006).
Piechowski, et al., "Inhibition of melanocortin-4 receptor dimerization by substitutions in intracellular loop 2.", J Mol Endocrinol 51, 109-118 (2013).
Pin, et al., "Allosteric functioning of dimeric class C G-protein-coupled receptors.", Febs J 272, 2947-2955 (2005).
Poggioli, et al., "ACTH-(1-24) and alpha-MSH antagonize feeding behavior stimulated by kappa opiate agonists.", Peptides 7, 843-848 (1986).
Portoghese, et al., "Heteromer Induction: An Approach to Unique Pharmacology?", ACS Chem Neurosci 8, 426-428 (2017).
Portoghese, et al., "Opioid Agonist and Antagonist Bivalent Ligands as Receptor Probes.", Life Sciences, 31(12 & 13), 1283-1286 (1982).
Rask-Andersen, et al., "Trends in the exploitation of novel drug targets.", Nat Rev Drug Discov 10, 579-590 (2011).
Russo, et al., "Synthesis of specific bivalent probes that functionally interact with 5-HT(4) receptor dimers.", J Med Chem 50(18), 4482-4492 (2007).
Santos, et al., "A comprehensive map of molecular drug targets.", Nat Rev Drug Discov 16, 19-34 (2017).
Sartania, et al., "Agonist occupancy of a single monomeric element is sufficient to cause internalization of the dimenc β2-adrenoceptor.", Cell Signal 19, 1928-1938 (2007).
Shinyama, et al., "Regulation of Melanocortin-4 Receptor Signaling: Agonist-Mediated Desensitization and Internalization.", Endocrinology 144, 1301-1314 (2003).
Singh, et al., "Incorporation of a Bioactive Reverse-Turn Heterocycle into a Peptide Template Using Solid-Phase Synthesis to Probe Melanocortin Receptor Selectivity and Ligand Conformations by 2D 1H NMR.", J Med Chem 54, 1379-1390 (2011).
Smeester, et al., "Targeting putative mu opioid/metabotropic glutamate receptor-5 heteromers produces potent antinociception in a chronic murine bone cancer model.", Eur J Pharmacol. 743, 48-52 (2014).
Smith, et al., "Allostery at G Protein-Coupled Receptor Homo- and Heteromers: Uncharted Pharmacological Landscapes.", Pharmacol Rev 62, 701-725 (2010).
Smith, et al., "Comparison of biosequences.", Adv Appl Math 2(4), 482-489 (1981).
Smith, "Experimental Ablation of the Hypophysis in the Frog Embryo", Science 44(1130), 280-282 (1916).
Stephenson, "A Modification of Receptor Theory", Br J Pharmacol Chemother 11, 379-393 (1956).
Szalai, "Allosteric interactions within the AT1 angiotensin receptor homodimer: Role of the conserved DRY motif.", Biochem Pharmacol 84, 477-485 (2012).
Tabor, et al., "Visualization and ligand-induced modulation of dopamine receptor dimerization at the single molecule level.", Sci Rep 6, 33233 (2016).
Takeyasu, et al., "Experimental evidence and dynamic aspects of spare receptor.", Life Sci 25(20), 1761-1771 (1979).
Tanner, et al., "Fasting-induced reductions in cardiovascular and metabolic variables occur sooner in obese vs. lean mice.", Exp Biol Med (Maywood) 235(12), 1489-1497 (2010).
Teitler, et al., "A new approach for studying GPCR dimers: drug-induced inactivation and reactivation to reveal GPCR dimer function in vitro, in primary culture, and in vivo.", Pharmacol Ther 133, 205-217 (2012).
Uckert, et al., "Melanocortin receptor agonists in the treatment of male and female sexual dysfunctions: results from basic research and clinical studies.", Expert Opin Invest Drugs 23(11), 1477-1483 (2014).
Vagner, et al., "Novel targeting strategy based on multimeric ligands for drug delivery and molecular imaging: homooligomers of α-MSH.", Bioorg Med Chem Lett 14, 211-215 (2004).
Violin, et al., "Biased ligands at G-protein-coupled receptors: promise and progress", Trends Pharmacol Sci 35, 308-316 (2014).
Wilczynski, et al., "Structure-Activity Relationships of the Unique and Potent Agouti-Related Protein (AGRP)-Melanocortin Chimeric Tyr-c[â-Asp-His-DPhe-Arg-Trp-Asn-Ala-Phe-Dpr]-Tyr-NH2 Peptide Template.", J Med Chem 48, 3060-3075 (2005).
Xiang, et al., "Peptide and Small Molecules Rescue the Functional Activity and Agonist Potency of Dysfunctional Human Melanocortin-4 Receptor Polymorphisms.", Biochemistry 46, 8273-8287 (2007).
Xiang, et al., "Pharmacological Characterization of 30 Human Melanocortin-4 Receptor Polymorphisms with the Endogenous Proopiomelanocortin Derived Agonists, Synthetic Agonists, and the

(56) References Cited

OTHER PUBLICATIONS

Endogenous Agouti-Related Protein (AGRP) Antagonist.", Biochemistry 49(22), 4583-4600 (2010).

Xiang, et al., "Pharmacological Characterization of 40 Human Melanocortin-4 Receptor Polymorphisms with the Endogenous Proopiomelanocortin-Derived Agonists and the Agouti-Related Protein (AGRP) Antagonist.", Biochemistry 45, 7277-7288 (2006).

Xu, et al., "Heterobivalent ligands target cell-surface receptor combinations in vivo.", Proc Natl Acad Sci USA 109, 21295-21300 (2012).

Yang, et al., "Biased signaling initiated by agouti-related peptide through human melanocortin-3 and -4 receptors", Biochim Biophys Acta 1862, 1485-1494 (2016).

Yang, et al., "Characterization of Agouti-Related Protein Binding to Melanocortin Receptors.", Mol Endocrinol 13, 148-155 (1999).

Zhao, et al., "Drug Conjugates with Poly(Ethylene Glycol).", Drug Delivery in Oncology, 627-656 (2012).

Zheng, et al., "Induced association of mu opioid (MOP) and type 2 cholecystokinin (CCK2) receptors by novel bivalent ligands.", J Am Chem 52(2), 247-258 (2009).

Zylbergold, et al., "A division of labor: asymmetric roles for GPCR subunits in receptor dimers.", Nat Chem Biol 5(9), 608-609 (2009).

\* cited by examiner (A) Illustration of Overlays of SKY4-48-44 and SKY4-48-46 Crude Analytical Traces (B) Illustration of Parallel Purification of SKY4-48-44 and SKY4-48-46

Comparing Function Dose-Response Curves for SKY4-48-18 [Ac-Arg-Arg-Arg-(pI)DPhe-Tic-NH$_2$] at the Selected MCRs Comparison of Binding and Function for SKY4-48-1 (Ac-His-DPhe-Arg-Trp-NH$_2$) and SKY6-24-2 [Ac-His-Arg-(pI)DPhe-Tic-NH$_2$] at the mMC3R and mMC4R Ac-His-Arg-(pI)DPhe-Tic-NH$_2$ R-DXaa-(pI)LPhe-DArg-DHis-NH$_2$

SEQUENCE LISTING

```
<160> NUMBER OF SEQ ID NOS: 120

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: DPhe
<220> FEATURE:
<223> OTHER INFORMATION: C-term NH2

<400> SEQUENCE: 1
```

```
Ser Tyr Ser Xaa Glu His Phe Arg Trp Gly Lys Pro Val
1               5                   10
```

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: DPhe
<220> FEATURE:
<223> OTHER INFORMATION: C-term NH2

<400> SEQUENCE: 2

```
His Phe Arg Trp
1
```

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 3

```
His Arg Phe Xaa
1
```

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 4

```
Arg Arg Phe Xaa
1
```

<210> SEQ ID NO 5

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 5

His Arg Phe Xaa
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 6

Xaa Arg Phe Xaa
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2
```

```
<400> SEQUENCE: 7

Ala Arg Phe Xaa
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 8

Xaa Arg Phe Xaa
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 9

Phe Arg Phe Xaa
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
<222> LOCATION: (3)..(3)
<223> OTHER INFORMATION: (pI)DPhe
```

```
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 10

Xaa Arg Phe Xaa
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Bip
<220> FEATURE:
<223> OTHER INFORMATION: C-term NH2

<400> SEQUENCE: 11

Xaa Arg Phe Xaa
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 12

Arg Arg Phe Ala
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 13

His Arg Phe Ala
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 14

Xaa Arg Phe Ala
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 15

Ala Arg Phe Ala
1

<210> SEQ ID NO 16
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 16

Xaa Arg Phe Ala
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 17

Phe Arg Phe Ala
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 18
```

```
Xaa Arg Phe Ala
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: 3Bal
<220> FEATURE:
<223> OTHER INFORMATION: C-term NH2

<400> SEQUENCE: 19

Xaa Arg Phe Ala
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 20

Arg Arg Phe Xaa
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
```

```
<222> LOCATION: (4)..(4)
<223> OTHER INFORMATION: Tic
<220> FEATURE:
<223> OTHER INFORMATION: C-term NH2

<400> SEQUENCE: 21

Xaa Arg Phe Xaa
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 22

Ala Arg Phe Xaa
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 23

Xaa Arg Phe Xaa
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 24

Phe Arg Phe Xaa
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 25

Xaa Arg Phe Xaa
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 26

Xaa Arg Phe Xaa
1

<210> SEQ ID NO 27
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 27

Arg Arg Phe Phe
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 28

His Arg Phe Phe
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 29

Xaa Arg Phe Phe
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 30

Ala Arg Phe Phe
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 31

Xaa Arg Phe Phe
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 32

Phe Arg Phe Phe
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
```

```
<222> LOCATION: (3)..(3)
<223> OTHER INFORMATION: (pI)DPhe
<220> FEATURE:
<223> OTHER INFORMATION: C-term NH2

<400> SEQUENCE: 33

Xaa Arg Phe Phe
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 34

Xaa Arg Phe Phe
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 35

Arg Arg Phe Xaa
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
```

```
<223> OTHER INFORMATION: Nal(2')
<220> FEATURE:
<223> OTHER INFORMATION: C-term NH2

<400> SEQUENCE: 36

His Arg Phe Xaa
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 37

Xaa Arg Phe Xaa
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 38

Ala Arg Phe Xaa
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 39

Xaa Arg Phe Xaa
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 40

Phe Arg Phe Xaa
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 41

Xaa Arg Phe Xaa
1

<210> SEQ ID NO 42
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Nal(2')
<220> FEATURE:
<223> OTHER INFORMATION: C-term NH2

<400> SEQUENCE: 42

Xaa Arg Phe Xaa
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 43

Arg Arg Phe Xaa
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 44

His Arg Phe Xaa
1
```

```
<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Bip
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 45

Xaa Arg Phe Xaa
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: 3Bal
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 46

Ala Arg Phe Xaa
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Tic
<220> FEATURE:
<221> NAME/KEY: MOD_RES
<222> LOCATION: (3)..(3)
<223> OTHER INFORMATION: (pI)DPhe
<220> FEATURE:
```

```
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 47

Xaa Arg Phe Xaa
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 48

Phe Arg Phe Xaa
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Nal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 49

Xaa Arg Phe Xaa
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(1)
<223> OTHER INFORMATION: DNal(2')
<220> FEATURE:
<221> NAME/KEY: MOD_RES
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: DNal(2')
<220> FEATURE:
<223> OTHER INFORMATION: C-term NH2

<400> SEQUENCE: 50

Xaa Arg Phe Xaa
1

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 51

Ser Tyr Ser Met Glu His Phe Arg Trp Gly Lys Pro Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 52

Ser Tyr Ser Met Glu His Arg Phe Trp Gly Lys Pro Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: DPhe
<220> FEATURE:
<223> OTHER INFORMATION: C-term NH2

<400> SEQUENCE: 53

Ser Tyr Ser Xaa Glu His Phe Arg Trp Gly Lys Pro Val
1               5                   10
```

```
<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (8)..(8)
<223> OTHER INFORMATION: DPhe
<220> FEATURE:
<223> OTHER INFORMATION: C-term NH2

<400> SEQUENCE: 54

Ser Tyr Ser Xaa Glu His Arg Phe Trp Gly Lys Pro Val
1               5                   10

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: DPhe
<220> FEATURE:
<223> OTHER INFORMATION: C-term NH2

<400> SEQUENCE: 55

His Arg Phe Trp
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DTrp
<220> FEATURE:
<221> NAME/KEY: MOD_RES
<222> LOCATION: (2)..(2)
<223> OTHER INFORMATION: DArg
<220> FEATURE:
<221> NAME/KEY: MOD_RES
<222> LOCATION: (4)..(4)
<223> OTHER INFORMATION: DHis
<220> FEATURE:
<223> OTHER INFORMATION: C-term NH2

<400> SEQUENCE: 56

Trp Arg Phe His
1
```

```
<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: (pI)DPhe
<220> FEATURE:
<223> OTHER INFORMATION: C-term NH2

<400> SEQUENCE: 57

His Phe Arg Trp
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: (pI)DPhe
<220> FEATURE:
<223> OTHER INFORMATION: C-term NH2

<400> SEQUENCE: 58

His Arg Phe Trp
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DPhe
<220> FEATURE:
<221> NAME/KEY: MOD_RES
<222> LOCATION: (2)..(2)
<223> OTHER INFORMATION: (pI)Phe
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DHis
<220> FEATURE:
<223> OTHER INFORMATION: C-term NH2

<400> SEQUENCE: 59

Phe Phe Arg His
1
```

```
<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term For
<220> FEATURE:
<221> NAME/KEY: MOD_RES
<222> LOCATION: (1)..(1)
<223> OTHER INFORMATION: DPhe
<220> FEATURE:
<221> NAME/KEY: MOD_RES
<222> LOCATION: (2)..(2)
<223> OTHER INFORMATION: (pI)Phe
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DHis
<220> FEATURE:
<223> OTHER INFORMATION: C-term NH2

<400> SEQUENCE: 60

Phe Phe Arg His
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: DTic
<220> FEATURE:
<221> NAME/KEY: MOD_RES
<222> LOCATION: (2)..(2)
<223> OTHER INFORMATION: (pI)Phe
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DHis
<220> FEATURE:
<223> OTHER INFORMATION: C-term NH2

<400> SEQUENCE: 61

Xaa Phe Arg His
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term For
<220> FEATURE:
<221> NAME/KEY: MOD_RES
```

```
<222> LOCATION: (1)..(1)
<223> OTHER INFORMATION: DTic
<220> FEATURE:
<221> NAME/KEY: MOD_RES
<222> LOCATION: (2)..(2)
<223> OTHER INFORMATION: (pI)Phe
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: DHis
<220> FEATURE:
<223> OTHER INFORMATION: C-term NH2

<400> SEQUENCE: 62

Xaa Phe Arg His
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 63

His Arg Phe Xaa
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 64

His Arg Phe Xaa
1

<210> SEQ ID NO 65
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 65

His Arg Phe Pro
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 66

His Arg Phe Xaa
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 67

His Arg Phe Xaa
1

<210> SEQ ID NO 68
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 68

His Arg Phe Xaa
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 69

His Arg Phe Pro
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 70

His Gln Phe Xaa
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
              peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 71

His Gln Phe Xaa
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 72

His Gln Phe Xaa
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 73

His Gln Phe Pro
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 74

His Gln Phe Xaa
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 75

His Gln Phe Xaa
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 76

His Gln Phe Xaa
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 77

His Gln Phe Pro
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 78

Arg Arg Phe Xaa
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 79

Arg Arg Phe Xaa
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

```
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 80

Arg Arg Phe Pro
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 81

Arg Arg Phe Xaa
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 82

Arg Arg Phe Xaa
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 83

Arg Arg Phe Xaa
 1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 84

Arg Arg Phe Pro
 1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 85

Arg Gln Phe Xaa
 1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 86

Arg Gln Phe Xaa
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 87

Arg Gln Phe Xaa
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 88

Arg Gln Phe Pro
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
```

<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 89

Arg Gln Phe Xaa
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 90

Arg Gln Phe Xaa
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 91

Arg Gln Phe Xaa
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe

```
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 92

Arg Gln Phe Pro
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 93

Val Arg Phe Xaa
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 94

Val Arg Phe Xaa
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
```

```
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 95

Val Arg Phe Xaa
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 96

Val Arg Phe Pro
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 97

Val Arg Phe Xaa
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
```

<222> LOCATION: (4)..(4)
<223> OTHER INFORMATION: DTic
<220> FEATURE:
<223> OTHER INFORMATION: C-term NH2

<400> SEQUENCE: 98

Val Arg Phe Xaa
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 99

Val Arg Phe Xaa
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 100

Val Arg Phe Pro
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)

```
<223> OTHER INFORMATION: LTic
<220> FEATURE:
<223> OTHER INFORMATION: C-term NH2

<400> SEQUENCE: 101

Val Gln Phe Xaa
1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 102

Val Gln Phe Xaa
1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: LCha
<220> FEATURE:
<223> OTHER INFORMATION: C-term NH2

<400> SEQUENCE: 103

Val Gln Phe Xaa
1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pI)Phe
<220> FEATURE:
<221> NAME/KEY: MOD_RES
<222> LOCATION: (4)..(4)
<223> OTHER INFORMATION: DPro
```

```
<220> FEATURE:
<223> OTHER INFORMATION: C-term NH2

<400> SEQUENCE: 104

Val Gln Phe Pro
1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LTic
<220> FEATURE:
<223> OTHER INFORMATION: C-term NH2

<400> SEQUENCE: 105

Val Gln Phe Xaa
1

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DTic
<220> FEATURE:
<223> OTHER INFORMATION: C-term NH2

<400> SEQUENCE: 106

Val Gln Phe Xaa
1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: LCha
<220> FEATURE:
```

<223> OTHER INFORMATION: C-term NH2

<400> SEQUENCE: 107

Val Gln Phe Xaa
1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: D(pCl)Phe
<220> FEATURE:
<221> NAME/KEY: MOD_RES
<222> LOCATION: (4)..(4)
<223> OTHER INFORMATION: DPro
<220> FEATURE:
<223> OTHER INFORMATION: C-term NH2

<400> SEQUENCE: 108

Val Gln Phe Pro
1

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: (pI)DPhe
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: C-term NH2

<400> SEQUENCE: 109

Xaa Phe Arg Xaa
1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES -continued

```
<222> LOCATION: (3)..(3)
<223> OTHER INFORMATION: (pI)DPhe
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: C-term NH2

<400> SEQUENCE: 110

Xaa Arg Phe Xaa
1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: (pI)Phe
<220> FEATURE:
<221> NAME/KEY: MOD_RES
<222> LOCATION: (3)..(3)
<223> OTHER INFORMATION: DArg
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: C-term NH2

<400> SEQUENCE: 111

Xaa Phe Arg Xaa
1

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Bu
<220> FEATURE:
<221> NAME/KEY: MOD_RES
<222> LOCATION: (2)..(2)
<223> OTHER INFORMATION: DPhe
<220> FEATURE:
<223> OTHER INFORMATION: C-term NH2

<400> SEQUENCE: 112

His Phe Arg Trp Gly
1               5

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 113

His Phe Arg Trp
1

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Nle
<220> FEATURE:
<223> OTHER INFORMATION: C-term NH2

<400> SEQUENCE: 114

Ser Tyr Ser Xaa Glu His Arg Phe Phe Gly Lys Pro Val
1               5                   10

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (1)..(4)
<223> OTHER INFORMATION: Cyclic
<220> FEATURE:
<221> NAME/KEY: MOD_RES
<222> LOCATION: (3)..(3)
<223> OTHER INFORMATION: DPhe or LPhe
<220> FEATURE:
<221> NAME/KEY: MOD_RES
<222> LOCATION: (5)..(5)
<223> OTHER INFORMATION: DTrp or LTrp
<220> FEATURE:
<223> OTHER INFORMATION: C-term NH2

<400> SEQUENCE: 115

Cys Arg Phe Cys Trp
1               5

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: (X)DPhe where X is an hydrogen or iodine
      replacement
<220> FEATURE:
<223> OTHER INFORMATION: C-term NH2

<400> SEQUENCE: 116

His Phe Arg Trp
1
```

```
<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(4)
<223> OTHER INFORMATION: Any amino acid
<220> FEATURE:
<223> OTHER INFORMATION: C-term NH2

<400> SEQUENCE: 117

Ala Xaa Xaa Xaa
1

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(4)
<223> OTHER INFORMATION: Any amino acid
<220> FEATURE:
<223> OTHER INFORMATION: C-term NH2

<400> SEQUENCE: 118

His Xaa Xaa Xaa
1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(4)
<223> OTHER INFORMATION: Any amino acid
<220> FEATURE:
<223> OTHER INFORMATION: C-term NH2

<400> SEQUENCE: 119

Arg Xaa Xaa Xaa
1

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Tic
<220> FEATURE:
<223> OTHER INFORMATION: C-term NH2

<400> SEQUENCE: 120

Xaa Xaa Xaa Xaa
1
```

MELANOCORTIN LIGANDS AND METHODS OF USE THEREOF

RELATED APPLICATION

This application claims the benefit of priority of U.S. Provisional Application Ser. No. 62/342,715 filed on May 27, 2016, which application is incorporated by reference herein.

GOVERNMENT FUNDING

This invention was made with government support under RO1 DK091906 awarded by the National Institutes of Health. The government has certain rights in the invention.

BACKGROUND OF THE INVENTION

Many signaling systems in the human body control appetite and body weight. All of these different signaling systems feed into the brain; however, the final process that controls appetite and weight is mediated by the melanocortin receptors. The two melanocortin receptors expressed in the brain are the melanocortin-3 receptor (MC3R) and the melanocortin-4 receptor (MC4R). Natural mutations in the melanocortin-4 receptor in humans have been reported to cause severe childhood-onset morbid obesity. It has been hypothesized the melanocortin-4 receptor affects immediate satiety whereas the melanocortin-3 receptor affects the long-term energy needs and food consumption in the body. There has been an enormous effort in the development of anti-obesity drugs targeting the melanocortin-4 receptor; however, these compounds have been reported to have number of side effects, including increased blood pressure (New England Journal of Medicine, 2009, vol 360, pp 44-52). Accordingly, there is a need for new melanocortin ligands, such as melanocortin-3 ligands (e.g., selective melanocortin-3 ligands). Specifically, there is a need for melanocortin-3 ligands (e.g., selective melanocortin-3 ligands), which do not have unwanted side effects.

SUMMARY OF THE INVENTION

Accordingly, described herein are compounds that are able to simultaneously activate the melanocortin-3 receptor and block the activation of the melanocortin-4 receptor, as well as compounds that selectively block the activation of the melanocortin-3 receptor and do not either activate or block the melanocortin-4 receptor. There is evidence suggesting that (1) targeting the melanocortin-3 receptor does not increase blood pressure upon activation and (2) targeting the melanocortin-3 receptor may induce weight loss. Thus, in certain embodiments, a compound of the invention may be used to treat obesity without the unwanted side effects associated with compounds that target MC4R. Additionally, compounds may be used as a therapy to modify appetite.

Accordingly, certain embodiments of the invention provide a compound of formula (I):

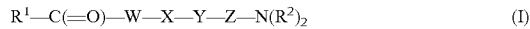

$$R^1-C(=O)-W-X-Y-Z-N(R^2)_2 \qquad (I)$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-arginine or L-glutamine and Y is a residue of D-phenylalanine, wherein the phenyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl; or X is a residue of L-phenylalanine, wherein the phenyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl, and Y is a residue of D-arginine or D-glutamine; and Z is a residue of an amino acid; or a salt thereof.

Certain embodiments of the invention provide a pharmaceutical composition comprising a compound of formula (I) as described herein, or a pharmaceutically acceptable salt thereof, and a pharmaceutically acceptable carrier.

Certain embodiments of the invention provide a dietary supplement comprising a compound of formula (I) as described herein, or a salt thereof.

Certain embodiments of the invention provide a method for modulating metabolic activity in a mammal in need thereof, comprising administering an effective amount of a compound of formula (I) as described herein, or a pharmaceutically acceptable salt thereof, to the mammal.

Certain embodiments of the invention provide a compound of formula (I) as described herein, or a pharmaceutically acceptable salt thereof, for modulating metabolic activity in a mammal.

Certain embodiments of the invention provide the use of a compound of formula (I) as described herein, or a pharmaceutically acceptable salt thereof, to prepare a medicament for modulating metabolic activity in a mammal in need thereof.

Certain embodiments of then invention provide a method of treating obesity or a disease associated with obesity (e.g., diabetes, cardiovascular disease or hypertension) in a mammal in need thereof, comprising administering an effective amount of a compound of formula (I) as described herein, or a pharmaceutically acceptable salt thereof, to the mammal.

Certain embodiments of the invention provide a compound of formula (I) as described herein, or a pharmaceutically acceptable salt thereof, for the prophylactic or therapeutic treatment of obesity or a disease associated with obesity in a mammal in need thereof.

Certain embodiments of the invention provide the use of a compound of formula (I) as described herein, or a pharmaceutically acceptable salt thereof, to prepare a medicament for the treatment of obesity or a disease associated with obesity in a mammal in need thereof.

Certain embodiments of the invention provide a method of treating cachexia in a mammal in need thereof, comprising administering an effective amount of a compound of formula (I) as described herein, or a pharmaceutically acceptable salt thereof, to the mammal.

Certain embodiments of the invention provide a compound of formula (I) as described herein, or a pharmaceutically acceptable salt thereof, for the prophylactic or therapeutic treatment of cachexia in a mammal in need thereof.

Certain embodiments of the invention provide the use of a compound of formula (I) as described herein, or a pharmaceutically acceptable salt thereof, to prepare a medicament for the treatment of cachexia in a mammal in need thereof.

Certain embodiments of the invention provide a method of modulating appetite in a mammal in need thereof, comprising administering an effective amount of a compound of formula (I) as described herein, or a pharmaceutically acceptable salt thereof, to the mammal.

Certain embodiments of the invention provide a compound of formula (I) as described herein, or a pharmaceutically acceptable salt thereof, for modulating appetite in a mammal in need thereof.

Certain embodiments of the invention provide the use of a compound of formula (I) as described herein, or a pharmaceutically acceptable salt thereof, to prepare a medicament for modulating appetite in a mammal in need thereof.

Certain embodiments of the invention provide a compound of formula (I) as described herein, or a pharmaceutically acceptable salt thereof, for use in medical therapy.

DETAILED DESCRIPTION

Figure 1:
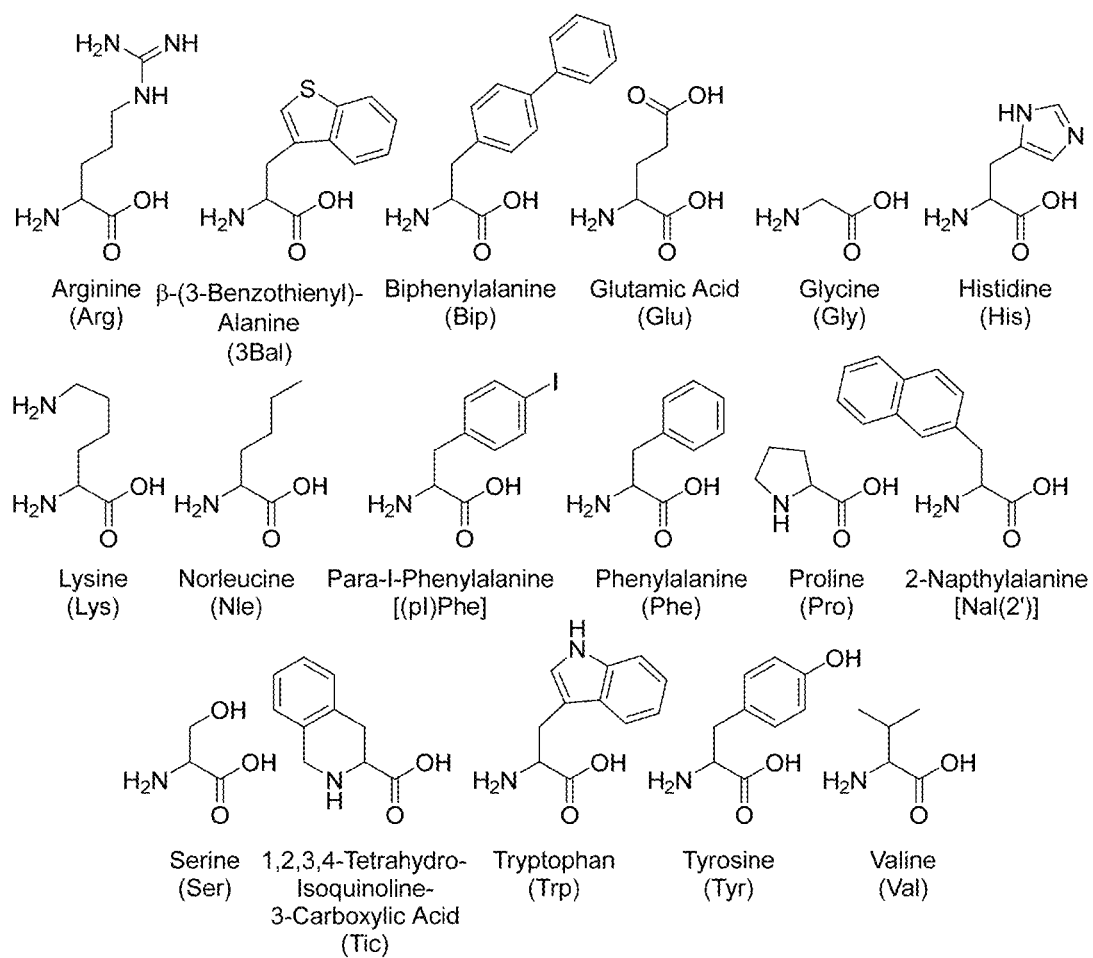
FIG. 1. Amino acid building blocks for the reported library. The stereochemistry is not shown; however, it is included in the compound sequences.

As described herein, certain compounds of the invention are capable of simultaneously activating the melanocortin-3 receptor and blocking the activation of the melanocortin-4 receptor (e.g., compounds of formula (Ia); e.g., Ac-Xaa(1)-Arginine-(para-Iodo)-D-Phenylalanine-Xaa(4)-NH$_2$(SEQ ID NO:110), wherein Xaa(1) and Xaa(4) are various natural and non-natural amino acids and Ac indicates the N-terminus is acetylated). Additionally, certain other compounds of the invention selectively block the activation of the melanocortin-3 receptor and do not activate or block the melanocortin-4 receptor (e.g., compounds of formula (Ib); e.g., Ac-Xaa(1)-(para-Iodo)-L-Phenylalanine-D-Arginine-Xaa (4)-NH$_2$ (SEQ ID NO:11, wherein Xaa(1) and Xaa(4) are various natural and non-natural amino acids and Ac indicates the N-terminus is acetylated).

Compounds of Formula (I)

Certain embodiments of the invention provide a compound of formula (I):

$$R^1—C(=O)—W—X—Y—Z—N(R^2)_2 \quad (I)$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-arginine or L-glutamine and Y is a residue of D-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl; or X is a residue of L-phenylalanine, wherein the phenyl ring is optionally substituted with one or more halo groups, $(C_1-C_4)$alkyl, $—O(C_1-C_4)$alkyl, $(C_1-C_4)$haloalkyl, $—O(C_1-C_4)$haloalkyl, and Y is a residue of D-arginine or D-glutamine; and Z is a residue of an amino acid;

or a salt thereof.

Certain embodiments of the invention provide a compound of formula (I'):

$$R^1—C(=O)—W—X—Y—Z—N(R^2)_2 \quad (I')$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-arginine and Y is a residue of D-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl; or X is a residue of L-phenylalanine, wherein the phenyl ring is optionally substituted with one or more halo groups, $(C_1-C_4)$alkyl, $—O(C_1-C_4)$alkyl, $(C_1-C_4)$haloalkyl, $—O(C_1-C_4)$haloalkyl, and Y is a residue of D-arginine; and Z is a residue of an amino acid;

or a salt thereof.

Certain embodiments of the invention provide a compound of formula (Ia):

$$R^1—C(=O)—W—X—Y—Z—N(R^2)_2 \quad (Ia)$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-arginine or L-glutamine and Y is a residue of D-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl; and Z is a residue of an amino acid;

or a salt thereof.

Certain embodiments of the invention provide a compound of formula (Ia'):

$$R^1—C(=O)—W—X—Y—Z—N(R^2)_2 \quad (Ia')$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-arginine and Y is a residue of D-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl; and Z is a residue of an amino acid;

or a salt thereof.

In certain embodiments, X is a residue of L-arginine and Y is a residue of D-phenylalanine, wherein the phenyl ring is substituted with one or more halo groups, $(C_1-C_4)$alkyl, $—O(C_1-C_4)$alkyl, $(C_1-C_4)$haloalkyl, or $—O(C_1-C_4)$haloalkyl.

In certain embodiments, X is a residue of L-arginine and Y is a residue of D-phenylalanine, wherein the phenyl ring is optionally substituted with one or more halo groups (e.g., fluoro, chloro, bromo, or iodo).

In certain embodiments, X is a residue of L-arginine and Y is a residue of D-phenylalanine, wherein the phenyl ring is substituted with one or more halo groups (e.g., fluoro, chloro, bromo, or iodo).

In certain embodiments, X is a residue of L-arginine and Y is a residue of D-phenylalanine, wherein the phenyl ring is substituted with one halo group (e.g., fluoro, chloro, bromo, or iodo). In certain embodiments, the ring is substituted with an iodo group. In certain embodiments, the ring is para-substituted with an iodo group. In certain embodiments, the ring is substituted with a chloro group. In certain embodiments, the ring is para-substituted with an chloro group.

In certain embodiments, X is a residue of L-glutamine and Y is a residue of D-phenylalanine, wherein the phenyl ring is substituted with one or more halo groups, $(C_1-C_4)$alkyl, $—O(C_1-C_4)$alkyl, $(C_1-C_4)$haloalkyl, or $—O(C_1-C_4)$haloalkyl.

In certain embodiments, X is a residue of L-glutamine and Y is a residue of D-phenylalanine, wherein the phenyl ring is optionally substituted with one or more halo groups (e.g., fluoro, chloro, bromo, or iodo).

In certain embodiments, X is a residue of L-glutamine and Y is a residue of D-phenylalanine, wherein the phenyl ring is substituted with one or more halo groups (e.g., fluoro, chloro, bromo, or iodo).

In certain embodiments, X is a residue of L-glutamine and Y is a residue of D-phenylalanine, wherein the phenyl ring is substituted with one halo group (e.g., fluoro, chloro, bromo, or iodo). In certain embodiments, the ring is substituted with an iodo group. In certain embodiments, the ring is para-substituted with an iodo group. In certain embodiments, the ring is substituted with a chloro group. In certain embodiments, the ring is para-substituted with a chloro group.

Certain embodiments of the invention provide a compound of formula (Ib):

$$R^1—C(=O)—W—X—Y—Z—N(R^2)_2 \quad (Ib)$$

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl; and Y is a residue of D-arginine or D-glutamine; and Z is a residue of an amino acid;

or a salt thereof.

Certain embodiments of the invention provide a compound of formula (Ib'):

R¹—C(=O)—W—X—Y—Z—N(R²)₂    (Ib')

wherein $R^1$ is H, $(C_1-C_6)$cycloalkyl or $(C_1-C_4)$alkyl, optionally substituted with cycloalkyl;

each $R^2$ is independently H or $(C_1-C_6)$alkyl;

W is a residue of an amino acid;

X is a residue of L-phenylalanine, wherein the phenyl ring is optionally substituted with one or more halo groups, $(C_1-C_4)$alkyl, —O$(C_1-C_4)$alkyl, $(C_1-C_4)$haloalkyl, or —O$(C_1-C_4)$haloalkyl; and Y is a residue of D-arginine; and Z is a residue of an amino acid;

or a salt thereof.

In certain embodiments X is a residue of L-phenylalanine, wherein the phenyl ring is substituted with one or more halo groups, $(C_1-C_4)$alkyl, —O$(C_1-C_4)$alkyl, $(C_1-C_4)$haloalkyl, or —O—$(C_1-C_4)$haloalkyl, and Y is a residue of D-arginine.

In certain embodiments X is a residue of L-phenylalanine, wherein the phenyl ring is optionally substituted with one or more halo groups (e.g., fluoro, chloro, bromo, or iodo), and Y is a residue of D-arginine.

In certain embodiments X is a residue of L-phenylalanine, wherein the phenyl ring is substituted with one or more halo groups (e.g., fluoro, chloro, bromo, or iodo), and Y is a residue of D-arginine.

In certain embodiments, X is a residue of L-phenylalanine, wherein the phenyl ring is substituted with one halo group, and Y is a residue of D-arginine. In certain embodiments, the ring is substituted with an iodo group. In certain embodiments, the ring is para-substituted with an iodo group. In certain embodiments, the ring is substituted with an chloro group. In certain embodiments, the ring is para-substituted with an chloro group.

In certain embodiments X is a residue of L-phenylalanine, wherein the phenyl ring is substituted with one or more halo groups, $(C_1-C_4)$alkyl, —O$(C_1-C_4)$alkyl, $(C_1-C_4)$haloalkyl, or —O—$(C_1-C_4)$haloalkyl, and Y is a residue of D-glutamine.

In certain embodiments X is a residue of L-phenylalanine, wherein the phenyl ring is optionally substituted with one or more halo groups (e.g., fluoro, chloro, bromo, or iodo), and Y is a residue of D-glutamine.

In certain embodiments X is a residue of L-phenylalanine, wherein the phenyl ring is substituted with one or more halo groups (e.g., fluoro, chloro, bromo, or iodo), and Y is a residue of D-glutamine.

In certain embodiments X is a residue of L-phenylalanine, wherein the phenyl ring is substituted with one halo group, and Y is a residue of D-glutamine. In certain embodiments, the ring is substituted with an iodo group. In certain embodiments, the ring is para-substituted with an iodo group. In certain embodiments, the ring is substituted with an chloro group. In certain embodiments, the ring is para-substituted with an chloro group.

In certain embodiments, $R^1$ is H.
In certain embodiments, $R^1$ is $(C_1-C_6)$cycloalkyl.
In certain embodiments, $R^1$ is $(C_1-C_4)$alkyl, optionally substituted with cycloalkyl.
In certain embodiments, $R^1$ is $(C_1-C_4)$alkyl, substituted with cycloalkyl.
In certain embodiments, $R^1$ is methyl.
In certain embodiments, each $R^2$ is H.
In certain embodiments, each $R^2$ is $(C_1-C_6)$alkyl.
In certain embodiments, one $R^2$ is H and one $R^2$ is $(C_1-C_6)$alkyl.

In certain embodiments, W is a residue of a D amino acid. In certain embodiments, W is residue of an L amino acid. In certain embodiments, W is a natural amino acid. In certain embodiments, W is a non-natural amino acid. In certain embodiments, W is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO₂)L-Phe, (pNO₂)D-Phe, 2-L-Nal, 2-D-Nal, β-Ala, ε-Aminocaproic acid, D-Met[O₂], L-Met[O₂], L-dehydPro, D-dehydPro, L-(3I)Tyr and D-(3I)Tyr.

In certain embodiments, W is a residue of His (e.g., L-His or D-His). In certain embodiments, W is a residue of Arg (e.g., L-Arg or D-Arg). In certain embodiments, W is a residue of Val (e.g., L-Val or D-Val).

In certain embodiments, W is a residue of Tic (e.g., D-Tic or L-Tic). In certain embodiments, W is a residue of Phe (e.g., D-Phe or L-Phe).

In certain embodiments, W is a residue of L-His, L-Arg, D-Tic, L-Val or D-Phe.

In certain embodiments, Z is a residue of a D amino acid. In certain embodiments, Z is residue of an L amino acid. In certain embodiments, Z is a natural amino acid. In certain embodiments, Z is a non-natural amino acid. In certain embodiments, Z is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO₂)L-Phe, (pNO₂)D-Phe, 2-L-Nal, 2-D-Nal, β-Ala, ε-Aminocaproic acid, D-Met[O₂], L-Met[O₂], L-dehydPro, D-dehydPro, L-(3I)Tyr and D-(3I)Tyr.

In certain embodiments, Z is residue of Tic (e.g., L-Tic or D-Tic). In certain embodiments, Z is residue of 2-Nal (e.g., 2-D-Nal or 2-L-Nal). In certain embodiments, Z is residue of His (e.g., D-His or L-His). In certain embodiments, Z is residue of Cha (e.g., L-Cha or D-Cha). In certain embodiments, Z is residue of Pro (e.g., D-Pro or L-Pro).

In certain embodiments, Z is residue of L-Tic, D-Tic, L-Cha, D-Pro, 2-D-Nal or D-His.

In certain embodiments, a compound of formula (Ia) is:

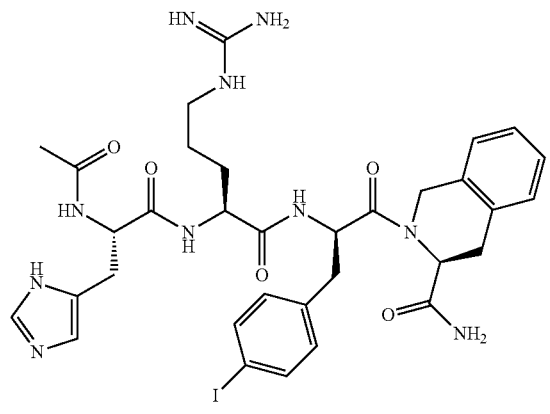

-continued

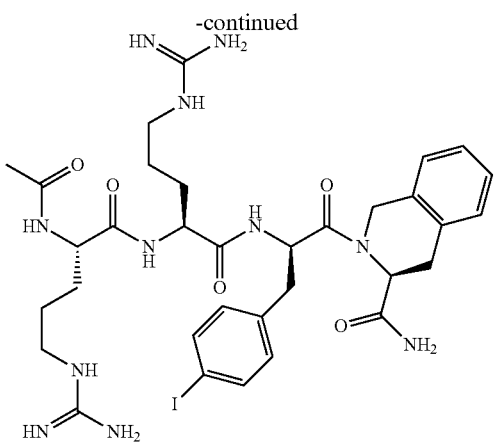

or

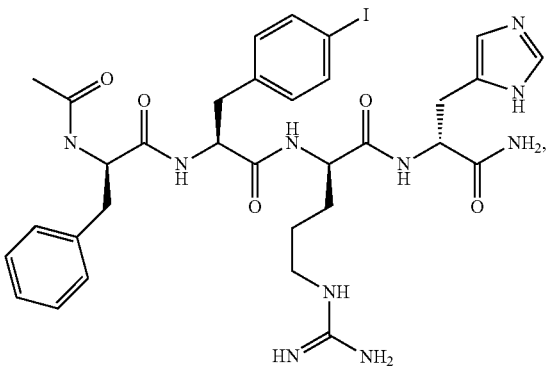

or a salt thereof.

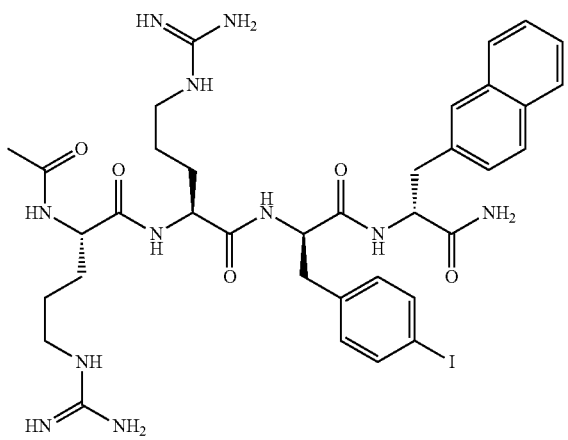

or a salt thereof.

Certain embodiments of the invention provide a compound of formula (Ia) as described in Table 1 or Table 5. Certain embodiments of the invention provide a compound of formula (Ia) as described in Table 9b.

In certain embodiments, a compound of formula (Ib) is:

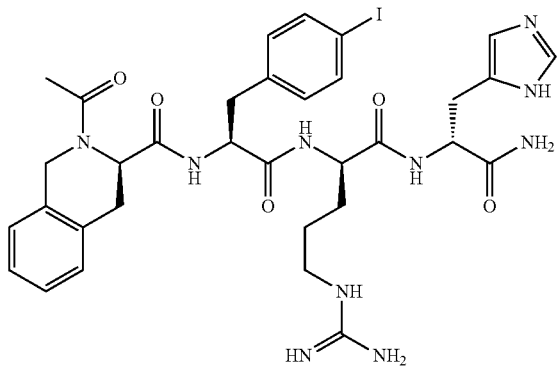

or a salt thereof.

Certain embodiments of the invention provide a compound as described in Table 5 selected from SKY2-125-5, SKY2-125-3, SKY5-121 and CJL-1-20, and salts thereof.

Certain embodiments of the invention provide a compound of formula (Ib) as described in Table 5.

In one embodiment, the compound of formula (I) is selective (e.g., a selective agonist or antagonist) for a specific melanocortin receptor(s) (e.g., MC1R, MC2R, MC3R, MC4R and/or MC5R). As described herein, agonist activity is the ability of a compound of the invention to stimulate a melanocortin receptor. The activity may be measured using an assay described in the Examples and may be reported as an $EC_{50}$ value (i.e., the concentration of compound needed to achieve 50% stimulation). In contrast, antagonist activity is the ability of a compound of the invention to block a melanocortin receptor. Antagonist activity of a given compound may be reported as a $pA_2$ value and measured using an assay described herein. $pA_2$ is defined as the negative $Logic_{10}$ of the molar concentration of the antagonist needed to reduce the activity of an agonist such that double the concentration of the agonist is needed to recover the level of activity observed when the agonist is assayed alone (Schild, British Journal of Pharmacology, 1947, volume 2, issue 3, pages 189-206). The antagonist activity may also be reported as a $K_i$ value, which is the inverse Log of $pA_2$. For example, a compound of the invention may be at least 5, at least 10, at least 50, at least 100, at least 500, or at least 1,000 fold selective for a given melanocortin receptor (e.g., MC1R, MC2R, MC3R, MC4R and/or MC5R) over another melanocortin receptor(s) in a selected assay (e.g., an assay described in the Examples herein). In one embodiment the compound may be at least 5, at least 10, at least 50, at least 100, at least 500, or at least 1,000 fold selective (e.g., a selective agonist or antagonist) for MC3R over another melanocortin receptor(s) (e.g., over MC4R). In one embodiment the inhibitor may be at least 5, at least 10, at least 50, at least 100, at least 500, or at least 1,000 fold selective (e.g., selective antagonist) for MC4R over another melanocortin receptor(s).

In certain embodiments, a compound of formula (Ia) is a melanocortin-3 receptor (MC3R) agonist (i.e., activates MC3R). In certain embodiments, a compound of formula (Ia) is a selective melanocortin-3 receptor (MC3R) agonist (i.e., selectively activates MC3R, e.g., over MC4R) (e.g., at least 5, at least 10, at least 50, at least 100, at least 500, or at least 1,000 fold selective). In certain embodiments, a compound of formula (Ia) is melanocortin-4 receptor (MC4R) antagonist (i.e., blocks activation of MC4R). In certain embodiments, a compound of formula (Ia) is a selective melanocortin-4 receptor (MC4R) antagonist (i.e., selectively blocks activation of MC4R) (e.g., at least 5, at least 10, at least 50, at least 100, at least 500, or at least 1,000 fold selective). In certain embodiments, a compound of formula (Ia) is a MC3R agonist and a MC4R antagonist. In certain embodiments, a compound of formula (Ia) is a selective MC3R agonist and a selective MC4R antagonist (e.g., at least 5, at least 10, at least 50, at least 100, at least 500, or at least 1,000 fold selective for agonist and/or antagonist activity).

In certain embodiments, a compound of formula (Ib) is a melanocortin-3 receptor (MC3R) antagonist (i.e., blocks activation of MC3R). In certain embodiments, a compound of formula (Ib) is a selective melanocortin-3 receptor (MC3R) antagonist (i.e., selectively blocks activation of MC3R over MC4R) (e.g., at least 5, at least 10, at least 50, at least 100, at least 500, or at least 1,000 fold selective). In certain embodiments, a compound of formula (Ib) is not a melanocortin-4 receptor (MC4R) agonist or antagonist (e.g., at least 5, at least 10, at least 50, at least 100, at least 500, or at least 1,000 fold selective for MC3R antagonist activity). In certain embodiments, a compound of formula (Ib) is a MC3R antagonist and is not a MC4R agonist or antagonist.

In certain embodiments, a compound of formula (Ia) has an $EC_{50}$ at MCR3 of less than 10 μM, e.g., less than 1 μM, e.g., less than 100 nM, e.g., less than 50 nM, e.g., less than 25 nM, e.g., less than 10 nM, e.g., less than 1 nM, e.g., or greater than 0.01 nM.

In certain embodiments, a compound of formula (Ia) has an $K_i$ at MCR4 of less than 10 μM, e.g., less than 1 μM, e.g., less than 500 nM, e.g., less than 250 nM, e.g., less than 100 nM, e.g., less than 50 nM, e.g., less than 25 nM, e.g., less than 10 nM, e.g., less than 1 nM, e.g., or greater than 0.01 nM.

In certain embodiments, a compound of formula (Ib) has an K at MCR3 of less than 10 μM, e.g., less than 1 μM, e.g., less than 500 nM, e.g., less than 250 nM, e.g., less than 100 nM, e.g., less than 50 nM, e.g., less than 25 nM, e.g., less than 10 nM, e.g., less than 1 nM, e.g., or greater than 0.01 nM.

In certain embodiments, a compound of formula (Ib) has an $EC_{50}$ at MC4R of greater than 1 μM and a $K_i$ at MCR4 of greater than 1 μM. In certain embodiments, a compound of formula (Ib) has an $EC_{50}$ at MC4R of greater than 10 μM and a $K_i$ at MCR4 of greater than 10 μM.

Certain embodiments of the invention provide a compound of formula (I), or a salt thereof, comprising one or more protecting groups. In certain embodiments, the protecting group is Boc, Fmoc or Tos. In certain embodiments, one or more amino acid side-chains contain a protecting group (e.g., Boc, Fmoc or Tos). In certain embodiments, the protecting group is Tos.

Compositions and Prodrugs

Certain embodiments of the invention provide a composition comprising a compound of formula (I) or a salt thereof, and a carrier.

Certain embodiments of the invention provide a pharmaceutical composition comprising a compound of formula (I) or a pharmaceutically acceptable salt thereof, and a pharmaceutically acceptable carrier.

Certain embodiments of the invention provide a dietary supplement comprising a compound of formula (I) or a salt thereof.

Certain embodiments of the invention also provide a prodrug of a compound of formula (I) or a salt thereof. As used herein the term "prodrug" refers to a biologically inactive compound that can be metabolized in the body to produce a biologically active form of the compound.

Methods of the Invention

Certain embodiments of the invention provide a method for modulating the activity of a melanocortin receptor, comprising contacting the melanocortin receptor in vitro, in situ, ex vivo or in vivo with a compound of formula (I) or a salt thereof. In certain embodiments, such a method comprises contacting a cell comprising the melanocortin receptor. In certain embodiments, the cell is in a mammal. In certain embodiments, the cell is contacted by administering the compound of formula (I) or a salt thereof (e.g., a pharmaceutically acceptable salt thereof) to the mammal. In certain embodiments, the compound of formula (I) or a salt thereof, increases the activity of the melanocortin receptor (e.g., as compared to a control). In certain embodiments, the compound of formula (I) or a salt thereof, decreases the activity the melanocortin receptor (e.g., as compared to a control). In certain embodiments, the melanocortin receptor is a melanocortin-3 receptor. In certain embodiments, the compound of formula (I) or a salt thereof, increases the activity of the melanocortin-3 receptor (e.g., as compared to a control). In certain embodiments, the compound of formula (I) or a salt thereof, decreases the activity of the melanocortin-3 receptor (e.g., as compared to a control). In certain embodiments, the melanocortin receptor is a melanocortin-4 receptor. In certain embodiments, the compound of formula (I) or a salt thereof, decreases the activity of the melanocortin-3 receptor (e.g., as compared to a control).

Certain embodiments of the invention provide a method for modulating appetite (i.e., increasing or decreasing appetite) in a mammal (e.g., a human) in need thereof, comprising administering an effective amount of a compound of formula (I), or a pharmaceutically acceptable salt thereof, to the mammal.

Certain embodiments of the invention provide a compound of formula (I), or a pharmaceutically acceptable salt thereof, for modulating appetite in a mammal.

Certain embodiments of the invention provide the use of a compound of formula (I), or a pharmaceutically acceptable salt thereof, to prepare a medicament for modulating appetite in a mammal in need thereof.

Certain embodiments of the invention provide a method for modulating metabolic activity (i.e., altering the desire to eat or not eat, altering activity, e.g., increasing or decreasing metabolic activity) in a mammal in need thereof, comprising administering an effective amount of a compound of formula (I), or a pharmaceutically acceptable salt thereof, to the mammal.

Certain embodiments of the invention provide a compound of formula (I), or a pharmaceutically acceptable salt thereof, for modulating metabolic activity in a mammal.

Certain embodiments of the invention provide the use of a compound of formula (I), or a pharmaceutically acceptable salt thereof, to prepare a medicament for modulating metabolic activity in a mammal in need thereof.

Certain embodiments of the invention provide a method of treating obesity or a disease associated with obesity (e.g., diabetes, cardiovascular disease or hypertension) in a mammal in need thereof, comprising administering an effective amount of a compound of formula (I), or a pharmaceutically acceptable salt thereof, to the mammal.

Certain embodiments of the invention provide a compound of formula (I), or a pharmaceutically acceptable salt thereof, for the prophylactic or therapeutic treatment of obesity or a disease associated with obesity in a mammal in need thereof.

Certain embodiments of the invention provide the use of a compound of formula (I), or a pharmaceutically acceptable salt thereof, to prepare a medicament for the treatment of obesity or a disease associated with obesity in a mammal in need thereof.

Certain embodiments of the invention provide a method of inducing weight loss or reducing weight gain in a mammal in need thereof, comprising administering an effective amount of a compound of formula (I), or a pharmaceutically acceptable salt thereof, to the mammal.

Certain embodiments of the invention provide a compound of formula (I), or a pharmaceutically acceptable salt thereof, for inducing weight loss or reducing weight gain in a mammal in need thereof.

Certain embodiments of the invention provide the use of a compound of formula (I), or a pharmaceutically acceptable salt thereof, to prepare a medicament for inducing weight loss or reducing weight gain in a mammal in need thereof.

Certain embodiments of the invention provide a method of inducing weight gain in a mammal in need thereof, comprising administering an effective amount of a compound of formula (Ib), or a pharmaceutically acceptable salt thereof, to the mammal.

Certain embodiments of the invention provide a compound of formula (I), or a pharmaceutically acceptable salt thereof, for inducing weight gain in a mammal in need thereof.

Certain embodiments of the invention provide the use of a compound of formula (I), or a pharmaceutically acceptable salt thereof, to prepare a medicament for inducing weight gain in a mammal in need thereof.

Certain embodiments of the invention provide a method of treating cachexia in a mammal in need thereof, comprising administering an effective amount of a compound of formula (I), or a pharmaceutically acceptable salt thereof, to the mammal.

Certain embodiments of the invention provide a compound of formula (I), or a pharmaceutically acceptable salt thereof, for the prophylactic or therapeutic treatment of cachexia in a mammal in need thereof.

Certain embodiments of the invention provide the use of a compound of formula (I), or a pharmaceutically acceptable salt thereof, to prepare a medicament for the treatment of cachexia in a mammal in need thereof.

In certain embodiments, the mammal has a disease associated cachexia, such as cancer or HIV/AIDS.

The ability of a compound of formula (I) to, e.g., modulate appetite, modulate metabolic activity, treat obesity or diseases associated with obesity (e.g., diabetes, cardiovascular disease or hypertension), induce weight loss, increase weight gain, decrease weight gain or treat cachexia or a disease associated with cachexia may be test using an assay known in the art or described in the Examples (e.g., Examples 3 and 4, describing in vivo feeding studies in mice).

In certain embodiments, the mammal is a human.

Certain embodiments of the invention provide a compound of formula (I), or a pharmaceutically acceptable salt thereof, for use in medical therapy.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of formula (I) (including salts and prodrugs thereof) can be formulated as pharmaceutical compositions and administered to a mammalian host, such as a human patient in a variety of forms adapted to the chosen route of administration, i.e., orally or parenterally, by intravenous, intramuscular, topical, nasal, inhalation, suppository, sub dermal osmotic pump, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I or II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. For example, compounds of formula (I), or salts thereof, may be administered with other agents that are useful for modulating appetite (i.e., increasing or decreasing), modulating metabolic activity, treating obesity or diseases associated with obesity (e.g., diabetes, cardiovascular disease or hypertension), inducing weight loss, increasing or decreasing weight gain, or treating cachexia or a disease associated with cachexia (e.g., cancer or HIV/AIDS). Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising compound of formula (I), or a pharmaceutically acceptable salt thereof, at least one other therapeutic agent, packaging material, and instructions for administering the compound of formula (I) or the pharmaceutically acceptable salt thereof and the other therapeutic agent or agents to an animal to modulate appetite, modulate metabolic activity, treat obesity or diseases associated with obesity (e.g., diabetes, cardiovascular disease or hypertension), induce weight loss, increase weight gain, decrease weight gain or treat cachexia or a disease associated with cachexia (e.g., cancer or HIV/AIDS).

Certain Definitions

The following definitions are used, unless otherwise described: "halo" or "halogen" refers to fluoro, chloro, bromo, or iodo. Alkyl denotes both straight and branched groups; but reference to an individual radical such as propyl embraces only the straight chain radical, a branched chain isomer such as isopropyl being specifically referred to. For example, an alkyl group can have 1 to 8 carbon atoms (i.e., $(C_1-C_8)$alkyl) or 1 to 6 carbon atoms (i.e., $(C_1-C_6$ alkyl) or 1 to 4 carbon atoms.

The term "haloalkyl" as used herein refers to an alkyl as defined herein, wherein one or more hydrogen atoms are each replaced by a halo substituent. For example, a $(C_1-C_6)$ haloalkyl is a $(C_1-C_6)$alkyl wherein one or more of the hydrogen atoms have been replaced by a halo substituent. Such a range includes one halo substituent on the alkyl group to complete halogenation of the alkyl group.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$ cycloalkyl can be cyclopropyl, cyclobutyl, cyclopentyl, or cyclohexyl; $(C_3-C_6)$ cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. PyrAla, ThiAla, (pCl)Phe, (pNO$_2$)Phe, ε-Aminocaproic acid, Met[O$_2$], dehydPro, (3I)Tyr, norleucine (Nle), para-I-phenylalanine ((pI)Phe), 2-napthylalanine (2-Nal), β-cyclohexylalanine (Cha), β-alanine (β-Ala), phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid (Tic), penicillamine, ornithine, citruline, α-methyl-alanine, para-benzoylphenylalanine, phenylglycine, propargylglycine, sarcosine, and tert-butylglycine) in D or L form. The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

As used herein, the term "residue of an amino acid" means a portion of an amino acid. For example, variables W, X, Y and Z are amino acids, wherein certain atoms (e.g., H or OH) have been removed to link the amino acids via a peptide bond. Additionally, further atoms may be removed from W and Z to form linkages with $R^1$ and $R^2$.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

The terms "treat" and "treatment" refer to both therapeutic treatment and prophylactic or preventative measures, wherein the object is to prevent or decrease an undesired physiological change or disorder, such as a metabolic disorder (e.g., obesity or cachexia) or a disease associated with the metabolic disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "mammal" as used herein refers to, e.g., humans, higher non-human primates, rodents, domestic, cows, horses, pigs, sheep, dogs and cats. In one embodiment, the mammal is a human. In one embodiment, the mammal is a female human. In one embodiment, the mammal is a male human.

The invention will now be illustrated by the following non-limiting Examples.

EXAMPLE 1

Identification of Dual Melanocortin-3 Agonists/Melanocortin-4 Antagonists

The following Example describes experiments that utilized a classical SAR strategy of double amino acid replacement. In these experiments, a novel tetrapeptide scaffold [Ac-Xaa$^1$-Arg-(pI)DPhe-Xaa$^4$-NH$_2$ (SEQ ID NO:110)] is reported. Specifically, 48 compound library of doubly-substituted tetrapeptides were designed based on this scaffold and characterized at the mouse melanocortin-1, -3, -4, and -5 receptors. This resulted in the identification of a first-in-class pharmacological profile for a tetrapeptide ligand at the central MC3 and MC4 receptor subtypes. Nine ligands with mixed pharmacology, MC3R agonist and MC4R antagonist, were discovered. Results indicated these compounds to be MC3R agonists ($EC_{50}$<1,000 nM) and MC4R antagonists (5.7>$pA_2$>7.8). The three most potent MC3R agonists, SKY4-48-18 [Ac-Arg-Arg-(pI)DPhe-Tic-$NH_2$ (SEQ ID NO:20)] ($EC_{50}$=16 nM), SKY6-24-2[Ac-His-Arg-(pI) DPhe-Tic-$NH_2$ (SEQ ID NO:3)] ($EC_{50}$=40 nM), and SKY4-48-42[Ac-Arg-Arg-(pI)DPhe-DNal (2')-$NH_2$ (SEQ ID NO:43)] ($EC_{50}$=57 nM) were more potent than melanocortin tetrapeptide Ac-His-DPhe-Arg-Trp-$NH_2$(SEQ ID NO:2) ($EC_{50}$=73 nM). This novel template contains an "Arg-Phe" sequence that is in reverse order with respect to the classical "His-Phe-Arg-Trp" melanocortin signaling motif, and this modification results in a pharmacological profile that is unique for the centrally located melanocortin receptors.

The melanocortin receptors are a family of class A, rhodopsin-like, G protein-coupled receptors (GPCRs) (Chhajlani, et al., *FEBS Lett.* 1992, 309 (3), 417-20; Mountjoy, et al., *Science* 1992, 257 (5074), 1248-1251; Roselli-Rehfuss, et al., *Proc. Natl. Acad. Sci. U.S.A.* 1993, 90 (19), 8856-60; Mountjoy, et al., *Mol. Endocrinol.* 1994, 8 (10), 1298-308; Gantz et al., *J. Biol. Chem.* 1993, 268 (11), 8246-50; Gantz, et al., *J. Biol. Chem.* 1993, 268 (20), 15174-15179; Gantz, et al., *Biochem. Biophys. Res. Commun.* 1994, 200 (3), 1214-20). They signal primarily through the $G_{s\alpha}$ subunit which results in the accumulation of the secondary messenger cyclic adenosine monophosphate (cAMP) (Haynes, R. C., Jr., *J. Biol. Chem.* 1958, 233 (5), 1220-2). There have been five melanocortin receptor (MCRs) subtypes cloned to date, labeled MC1R through MC5R, which mediate a myriad of functions. The MC1R is found primarily in the skin and is involved in the regulation of pigmentation. The MC2R is involved in steroidogenesis and is activated only by the adrenocorticotropic hormone (ACTH) (Schioth, et al., *Life Sci.* 1996, 59 (10), 797-801). Both the MC3R and MC4R are located in the brain and are integral in maintaining energy homoeostasis and body weight regulation. Furthermore, the MC4R has been investigated as an obesity drug target due to the identification of numerous single nucleotide polymorphisms in the MC4R of obese individuals, making this receptor the largest monogenic determinant of severe childhood-onset obesity (Farooqi, et al., *N. Engl. J. Med.* 2003, 348 (12), 1085-95). The MC5R has been identified to affect the exocrine gland function of mice, yet the function of this receptor in humans is relatively unknown (Chen, et al., *Cell* 1997, 91 (6), 789-798).

Stimulation of all five of the melanocortin receptors is mediated through pro-opiomelanocortin (POMC) peptide-derived products with additional reports indicating they can signal through other pathways including $G_{i/o}$, MAPK, and the Kir7.1 channel (Nakanishi, et al., *Nature* 1979, 278 (5703), 423-427; Büch, et al., *J. Biol. Chem.* 2009, 284 (39), 26411-26420; Mo, et al., *Biochim. Biophys. Acta.* 2013, 1832 (12), 1939-48; Ghamari-Langroudi, et al., *Nature* 2015, 520 (7545), 94-98). These peptide ligands include α-, β-, and γ-melanocyte stimulating hormones (MSH) which stimulate the MC1, MC3, MC4, and MC5 receptors, and the ACTH ligand which stimulates all five of the receptor subtypes (Cone, R. D., *The melanocortin receptors*. Humana Press: Totowa, N.J., 2000; p 551; Irani, et al., *Current Pharmaceutical Design* 2004, 10 (28), 3443-3479). Extensive structure-activity relationship (SAR) studies have determined the conserved His-Phe-Arg-Trp motif found in all of the endogenous melanocortin agonists to be the minimum sequence necessary for receptor activation and has been described as the core melanocortin signaling sequence (Hruby, et al., *J. Med. Chem.* 1987, 30 (11), 2126-30; Otsuka, H.; Inouye, K., *Bull. Chem. Soc. Jpn.* 1964, 37 (10), 1465-1471. Receptor stimulation is inhibited at the melanocortin-1, -3, and -4 receptors by two endogenous antagonists: agouti-signaling protein (ASIP) and agouti-related protein (AGRP) (Bultman, Cell 1992, 71 (7), 1195-1204; Miller, *Genes. Dev.* 1993, 7 (3), 454-67; Ollmann, *Science* 1997, 278 (5335), 135-138). SAR studies on the 132 amino acid sequence of Human AGRP have determined an Arg-Phe-Phe tripeptide sequence, AGRP (111-113), to be essential for antagonist activity (Ollmann, et al., *Science* 1997, 278 (5335), 135-138; Tota, *Biochemistry* 1999, 38 (3), 897-904; Wilczynski, *J. Med. Chem.* 2004, 47 (9), 2194-2207; Joseph, *J. Med. Chem.* 2004, 47 (27), 6702-6710). In vivo mouse studies have demonstrated that the synthetic melanocortin agonists can decrease food intake while the MC3R/MC4R melanocortin antagonists can promote food intake (Fan, et al., *Nature* 1997, 385 (6612), 165-168; Irani, et al., *Eur. J Pharmacol.* 2011, 660 (1), 80-87). These results support the hypothesis that the MC3R and MC4R may be viable drug targets for the treatment of metabolic diseases.

Animal knockout models indicate the two receptors have non-redundant roles in energy homeostasis. Mouse knockout models for each of the receptors results in an increase in fat tissue, yet there are some phenotypic differences, including the MC4R knockout mice are generally larger in size and the MC3R knockout mice are smaller in size; however, they have a fat to lean tissue ratio which is greater than their wild-type counterparts (Atalayer et al., *Am. J. Physiol. Regul. Integr. Comp. Physiol.* 2010, 298 (6), R1667-74). In addition, combined knockout results in an extreme obese phenotype. The phenotypic differences in the single knockout mice, as well as the extreme obese phenotype of the double knockout, suggests the receptors have non-redundant roles and they may work together via a synergistic mechanism. Studies with patients in the clinic with selective MC4R and non-selective melanocortin agonists have indicated targeting the MC3R may prove to be better than the MC4R in terms of an anti-obesity therapy (Ni, et al., *J. Hypertens.* 2006, 24 (11), 2239-2246; Wessells, et al., *J. Urol.* 1998, 160 (2), 389-93; Hadley, M. E., *Peptides* 2005, 26 (10), 1687-1689; Van der Ploeg, et al., *Proc. Natl. Acad. Sci. U.S.A.* 2002, 99 (17), 11381-6).

Side effects observed when treating obesity with MC4R drugs in humans include increasing blood pressure and inducing erectile function. The hypertensive cardiovascular effects associated with central administration of the POMC derived peptides α- and $γ_2$-MSH were demonstrated in a rodent model to potentially be MC3R-independent and MC4R-dependent processes. Although, these results may not correlate with humans since it was later reported $γ_2$-MSH has activity at both the mouse MC3R and mouse MC5R. This finding should be taken into consideration when interpreting in vivo results since the MC5R is found, among other places, in heart tissue (Joseph, et al., *Peptides* 2010, 31 (12), 2304-2313). Reports on MC3R selective compounds have been primarily limited to analogs of α-MSH and γ-MSH (Carotenuto, et al., *J. Med. Chem.* 2015, 58 (24), 9773-9778; Grieco, et al., *J. Med. Chem.* 2000, 43 (26), 4998-5002; Kavarana, et al., *J Med. Chem.* 2002, 45 (12), 2644-2650; Grieco, et al., *Peptides* 2007, 28 (6), 1191-1196; Grieco, et al., *J. Med. Chem.* 2002, 45 (24), 5287-5294; Ballet, et al., *Bioorg. Med. Chem. Lett.* 2007, 17 (9), 2492-2498). The identification of selective MC3R compounds with more drug like properties, such as a lower molecular weight (MW<1,000), may result in the development of a valuable therapeutic strategy for the current obesity epidemic, as compared to a therapeutic targeting the activation the MC4R which has several undesirable side effects.

The identification of a series of dual MC3R agonist/MC4R antagonist compounds are reported herein, which to the best of the inventors' knowledge, are first-in-class for melanocortin ligands. It is postulated that the observed effect on energy homeostasis and body weight regulation from these compounds could be greater than the sum of stimulating/blocking each receptor alone. That is to say, the MC3R and MC4R could be working in synergy and the expected decrease in food intake with the central administration of an agonist at the MC3R could be allosterically modulated via the central administration of an antagonist at the MC4R (Irani, et al., *Eur. J. Pharmacol.* 2011, 660 (1), 80-87). Thus, the administration of these dual agonist/antagonist compounds may yield an amplified weight-loss benefit from stimulating the MC3R in addition to inducing a decrease in blood pressure from antagonizing the MC4R, which is a noted difference in patients with MC4R-defficent mutations (Greenfield, et al., *New Engl J Med* 2009, 360 (1), 44-52). Recent developments in this area illustrate the power of receptor synergy in relationship to weight-loss. For example, a unimolecular co-agonist targeting both the glucagon-like peptide-1 (GLP-1) and glucose-dependent insulinotropic polypeptide (GIP) receptors has been reported as a potential therapeutic for the treatment of so called diabesity, in addition to, a tri-agonist targeting the GLP-1, GIP, and glucagon receptors (Day, et al., *Nat Chem Biol* 2009, 5 (10), 749-757; Finan, B. et al., *Science Translational Medicine* 2013, 5 (209), 209ra151-209ra151; Finan, B. et al., at. *Med.* 2015, 21 (1), 27-36).

The discovery of the reported dual agonist/antagonist compounds described herein utilized a combination of different peptide methodologies.

Classical peptide structure-activity relationship (SAR) approaches, such as truncation studies and single residue replacement scans (example in chapter 3), have yielded a variety of ligands with differing potencies and selectivity profiles at the receptor subtypes (Hruby, et al., *J. Med. Chem.* 1987, 30 (11), 2126-30; Haskell-Luevano, et al., *Peptides* 1996, 17 (6), 995-1002; Grieco, et al., *J. Med. Chem.* 2000, 43 (26), 4998-5002; Sawyer, et al., *Proc. Natl. Acad. Sci. U.S.A.* 1980, 77 (10), 5754-8). These studies build upon preexisting knowledge and have been valuable in the development of potent, selective ligands. While useful, this approach has not generated a low molecule weight (M.W.<1, 000) MC3R selective ligand. An unbiased approach, such as mixture-based positional scanning libraries, may be used in order to generate new scaffolds with the desired pharmacological profile (Haslach, et al., *J. Med. Chem.* 2014, 57 (11), 4615-4628). Herein, a lead compound chemotype was selected from the minimal deconvolution of a mixture-based positional scanning library campaign. This lead compound was then followed up with a double residue replacement scan to yield a series of compounds with a central MC3R agonist MC4R antagonist dual pharmacological profile.

Mixture-based positional scanning libraries have been extensively reviewed (Houghten, et al., *J. Med. Chem.* 1999, 42 (19), 3743-3778; Houghten, *J. Comb. Chem.* 2008, 10 (1), 3-19; Pinilla, et al., *Nat. Med.* 2003, 9 (1), 118-122), and have been previously validated for studying the melanocortin receptors wherein tetrapeptides were identified that rescued the function of selected human MC4R single nucleotide polymorphisms (SNPs) (Haslach, et al., *J. Med. Chem.* 2014, 57 (11), 4615-4628). Compounds sharing a common scaffold are assayed in mixtures where each compound within the mixture shares a common side chain at a particular position. There is a propensity for large mixtures containing only a few potent compounds to nonetheless demonstrate an overall moderate activity, since the activity of a particular mixture is the harmonic mean of the constituents (Santos, *ACS Comb. Sci.* 2011, 13 (3), 337-344). These active mixtures are then identified as "hits," and combinations of "hits" can be synthesized and assayed as individual compounds. This technology allows for the rapid screening of millions of compounds/peptides, the development of an extensive SAR, and the prioritization of individual compounds that could be studied as part of the deconvolution process. The ability to efficiently screen millions of compounds/peptides enables a larger area of chemical space to be explored in an unbiased and efficient manner. Thus, novel scaffolds can be identified that are not based upon any previously performed SAR studies, and may generate ligands with novel potency and selectivity profiles.

Herein, the identification of a new synthetic tetrapeptide sequence is described, compound SKY6-24-2, Ac-His-Arg-(pI)DPhe-Tic-NH$_2$(SEQ ID NO:3). A key feature of this compound is an apparent structure reversal in the melanocortin signaling sequence residues of arginine and phenylalanine compared to the conserved His-Phe-Arg-Trp motif. Based on this template, it was hypothesized that substituting the first and fourth positions with several aromatic sidechains, could result in the discovery of new mMC3R scaffolds with novel pharmacology that could be used as molecular tools to probe the mechanism between the MC3 and MC4 receptors in vitro and in vivo (Holder, et al., *J. Med. Chem.* 2002, 45 (13), 2801-2810; Holder, et al., *J. Med. Chem.* 2002, 45 (26), 5736-5744).

Results

Identification of the Lead Compound SKY 6-24-2, Ac-His-Arg-(pI)DPhe-Tic-NH$_2$(SEQ ID NO:3)

The mixture-based positional scanning library TPI924 consists of 60 individual building blocks of D-amino acids, L-amino acids, and unnatural amino acids resulting in 240 mixtures each containing 216,000 compounds with an overall library representing 12,960,000 compounds. Each member of the combinatorial library share a common Ac-tetrapeptide-NH$_2$ scaffold, and within each mixture a single residue was held constant at a specific position. For example, all peptides in the first mixture shared the structure Ac-Ala-X-X-X-NH2 (SEQ ID NO:117), where X indicates a mixture of all 60 building blocks and therefore resulting in 216,000 (1×60×60×60) compounds within the mixture. The positional scanning library was constructed using the standard solid-phase synthesis N-α-tert-butyloxycarbonyl (Boc) protecting scheme, and the mixtures of compounds were synthesized using the previously reported teabag method (Houghten, R. A., *Proc. Natl. Acad. Sci. U.S.A.* 1985, 82 (15), 5131-5135).

The library was screened using a 96-well cAMP based colorimetric β-galactosidase assay using HEK293 cells stably expressing the cloned mMC3R (Chen, et al., *Anal. Biochem.* 1995, 226 (2), 349-354). The primary screen assessed for mixture activity at a stimulatory concentration of 100 µg/mL. The data were normalized to both protein content and the responses of the potent synthetic agonist NDP-MSH and forskolin (a melanocortin receptor independent activator of adenylate cyclase). Inspection of the screening data resulted in the hypothesis that the putative tetrapeptide Ac-His-Arg-(pI)DPhe-Tic-NH2 (SEQ ID NO:3) could serve as an unexplored MC3R chemotype that could be used to develop receptor selectivity profiles versus the MC4R. This can be considered a minimal version of the more typical deconvolution experiment wherein a set of individual compounds is produced based on a combination of the most active samples from each position of the mixture-based positional scanning library (Houghten, et al., *J. Med. Chem.* 1999, 42 (19), 3743-3778; Houghten et al., *J. Comb. Chem.* 2008, 10 (1), 3-19; Dooley, et al., *J. Biol. Chem.* 1998, 273 (30), 18848-18856). This lead tetrapeptide sequence was prioritized for study since the sequence contained a sequence similar to that of an apparent structure reversal in the melanocortin signaling sequence residues of arginine and phenylalanine compared to the conserved His-Phe-Arg-Trp (SEQ ID NO:113) motif found in the endogenous POMC melanocortin ligands. This "Arg-(pI)DPhe" motif was reminiscent of the postulated Arg-Phe-Phe pharmacophore found in ASIP and AGRP which has been extensively studied (Tota et al., *Biochemistry* 1999, 38 (3), 897-904; Wilczynski, et al., *J. Med. Chem.* 2004, 47 (9), 2194-2207; Kiefer, et al., *Biochemistry* 1998, 37 (4), 991-997. Ericson, et al., *J. Med. Chem.* 2015, 58 (11), 4638-4647. Haskell-Luevano, et al., *Biochemistry* 2001, 40 (20), 6164-6179).

The lead compound Ac-His-Arg-(pI)DPhe-Tic-NH$_2$(SEQ ID NO:3), SKY6-24-2, was synthesized using standard microwave assisted solid-phase N-α-fluorenylmethyloxycarbonyl (Fmoc) chemistry (Tala, et al., *Bioorg. Med. Chem. Lett.* 2015, 25 (24), 5708-5711; Stewart, et al., *Solid phase peptide synthesis*. 2nd ed.; Pierce Chemical Co.: Rockford, Ill., 1984; p xvi, 176 p). The compound was assessed for functional activity by the measurement of intracellular cAMP accumulation using the whole cell Amplified Luminescent Proximity Homogeneous Assay Screen (AlphaScreen®, Perkin-Elmer) in the same stably transfected HEK293 cells as the initial screen in a 384-well format (Tala, et al., *Bioorg. Med. Chem. Lett.* 2015, 25 (24), 5708-5711; Ericson, et al., *Bioorg. Med. Chem. Lett.* 2015, 25 (22), 5306-5308; Singh, et al., *A.C.S. Med. Chem. Lett.* 2015, 6 (5), 568-72). Preliminary results indicated the compound was equipotent, within the 3-fold inherent error associated with this assay, to the previously reported melanocortin tetrapeptide, SKY4-48-1, Ac-His-DPhe-Arg-Trp-NH$_2$ (SEQ ID NO:2) (40 vs 73 nM) at the mMC3R (Holder, et al., *J. Med. Chem.* 2002, 45 (13), 2801-2810; Holder, et al., *J. Med. Chem.* 2002, 45 (26), 5736-5744; Holder, et al., *Med. Chem.* 2002, 45 (14), 3073-3081; Holder, et al., *Peptides* 2003, 24 (1), 73-82; Haskell-Luevano, et al., *J. Med. Chem.* 2001, 44 (13), 2247-2252). In addition, minimal agonist activity was observed at a concentration of 100 μM for the mMC4R and subsequent antagonist experiments indicated the compound demonstrated antagonist activity at the mMC4R (pA$_2$=7.0, K$_i$=100 nM). To the best of the inventors' knowledge, this compound with agonist activity at the mMC3R and antagonist activity at the mMC4R is a pharmacological profile that is first-in-class and can serve the unmet need which currently exists in the field. This scaffold was termed the Tetrapeptide Agonist Compound (TACO) scaffold, due to the propensity for this tetrapeptide to stimulate the MC3R.

Double Substitution Library Design, Synthesis, and Evaluation

Based upon the initial experiments, the first and fourth positions were selected for further investigations as part of a double-substitution library. It was hypothesized that the second and third positions would be held constant [(Ac-Xaa$^1$-Arg-(pI)DPhe-Xaa$^4$-NH$_2$ (SEQ ID NO:110)], since previous studies on the linear truncated tetra- and pentapeptide analogs of α-MSH, Ac-His-DPhe-Arg-Trp-NH$_2$ (SEQ ID NO:2) and Bu-His-DPhe-Arg-Trp-Gly-NH$_2$ (SEQ ID NO:112), indicated alterations at these positions within the His-Phe-Arg-Trp (SEQ ID NO:113) signaling motif were generally detrimental to the activity at all of the receptors (Holder, et al., *Med. Chem.* 2002, 45 (14), 3073-3081; Holder, et al., *Peptides* 2003, 24 (1), 73-82; Danho, et al., *Bioorg. Med. Chem. Lett.* 2003, 13 (4), 649-652; Cheung, et al., *Bioorg. Med. Chem. Lett.* 2002, 12 (17), 2407-2410; Joseph, et al., *The journal of peptide research official journal of the American Peptide Society* 2005, 66 (5), 297-307). The substitutions selected for the library contain both natural and unnatural amino acids which have been previously shown to alter either the selectivity and/or the potency at the selected melanocortin receptor subtypes in the aforementioned linear, Ac-His-DPhe-Arg-Trp-NH$_2$ (SEQ ID NO:2) based, peptides (FIG. 1) (Holder, et al., *J. Med. Chem.* 2002, 45 (13), 2801-2810; Holder, et al., *J. Med. Chem.* 2002, 45 (26), 5736-5744; Danho, et al., *Bioorg. Med. Chem. Lett.* 2003, 13 (4), 649-652). For the first position of the tetrapeptide, arginine (Arg), histidine (His), biphenylalanine (Bip), β-(3-benzothienyl)-alanine (3Bal), 1,2,3,4-tetrahydroisoquinoline-3-carboxylic acid (Tic), phenylalanine (Phe), D/L 2-napthylalanine [DNal(2') and LNal(2')] were selected (FIG. 1) (Holder, et al., *J. Med. Chem.* 2002, 45 (13), 2801-2810). At the fourth position, Bip, 3Bal, Tic, Phe, DNal(2'), and LNal(2') were selected (Holder, et al., *J. Med. Chem.* 2002, 45 (26), 5736-5744). The library resulted in a total of 48 (8×1×1×6) analogs which included the resynthesis of the lead peptide SKY6-24-2 for a control; in addition, Ac-His-DPhe-Arg-Trp-NH$_2$ (SEQ ID NO:2) and NDP-MSH were also included for reference and comparison purposes. All peptides were synthesized manually in a microwave in parallel using standard Fmoc solid phase peptide synthesis (Tala, et al., *Bioorg. Med. Chem. Lett.* 2015, 25 (24), 5708-5711; Stewart, et al., *Solid phase peptide synthesis*. 2nd ed.; Pierce Chemical Co.: Rockford, Ill., 1984; p xvi, 176 p).

Figure 2A:
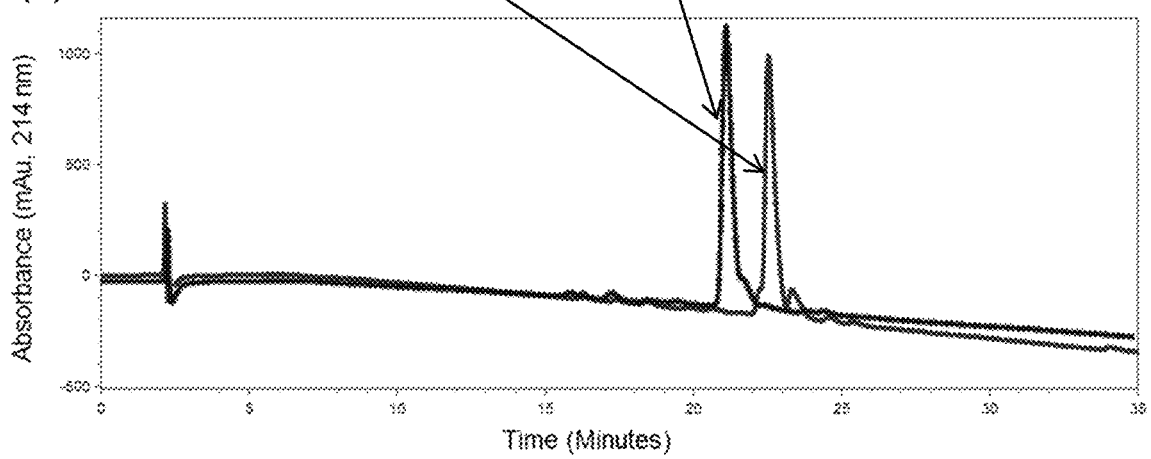
FIGS. 2A-B. Parallel Purification Method Used in this Study. Illustration of the RP-HPLC traces observed while implementing the parallel purification method used in this study. Crude peptides were selected for parallel purification when (A) overlays of the crude analytical traces (10% to 90% acetonitrile gradient in 0.1% trifluoroacetic acid in water over 35 minutes at 1.5 mL/min using an analytical 10 micron C18, 4.6×250 mm, Vydac Cat #218TP104) had the desired peptides within 5 minutes of each other and did not introduce impurities into the other peptide. The semipreparative parallel purification (B) could be achieved with a 15 minute separation method (typically 40% to 50% acetonitrile gradient in 0.1% trifluoroacetic acid in water over 15 minutes at 5 mL/min using a semipreparative 10 micron C18, 10×250 mm, Vydac Cat #218TP1010).
Figure 2B:
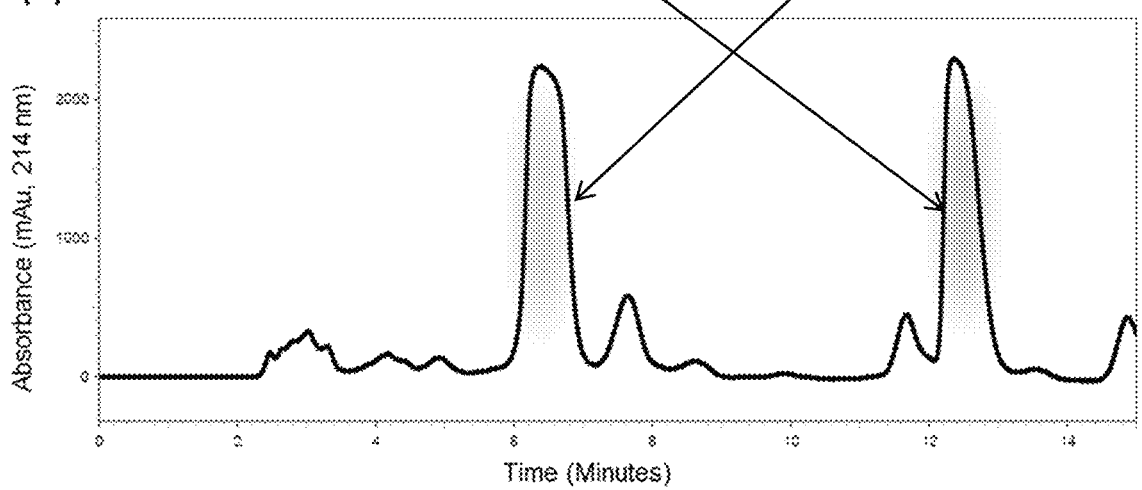

The compounds were purified by reverse phase high pressure liquid chromatography (RP-HPLC) on a semi-preparative scale, and the purification was done, whenever possible, as a mixture of two crude peptides to reduce instrument time and solvent usage by nearly half. Typically, in order to isolate 5 to 10 mg of a pure (>95% by UV absorption at λ=214 nm) tetrapeptide for a single compound, 40 mg of crude peptide would be dissolved and injected onto a semipreparative Vydac C18 column (10 micron, 10×250 mm, Vydac Cat #218TP1010) over the course of 25 injections with a flow rate 5 mL/min in a mixture of 0.1% trifluoroacetic acid in water and acetonitrile. A typical RP-HPLC method would consist of a 10 minute run, followed by a 10 minute column flush, and then a 10 minute column equilibration for a total of 30 minutes per injection. Over the course of the purification of a single peptide, the RP-HPLC would be in use for 12.5 hours and 1.9 liters of acetonitrile (approximately, 50% of the total RP-HPLC solvent). The selection process in pairing crude peptides for purification consisted of first running an analytical of each crude peptide on a standard 10% to 90% acetonitrile gradient in 0.1% TFA in water over 35 minutes at a rate of 1.5 mL/min using an analytical Vydac C18 column (10 micron, 4.6×250 mm, Vydac Cat #218TP104). Pairs of RP-HPLC traces wherein the desired peptide peaks came off within 5 minutes of each other without the introduction of impurities were paired up and then the peptides were combined for purification (FIG. 2A). With a modest 5 minute increase in the semipreparative RP-HPLC method, parallel purification of two crude peptides could be achieved (FIG. 2B). It was estimated this effort reduced the amount of RP-HPLC time by approximately 210 hours, or 8.75 days, in addition it reduced the amount of total solvent by 62.5 liters, of which approximately 50% was acetonitrile. Compounds were confirmed by matrix-assisted laser desorption ionization time of flight (MALDI-TOF) mass spectrometry at the University of Minnesota Mass Spectrometry Laboratory. They were assessed for purity by analytical RP-HPLC analysis using two different solvent systems (Table 4). Analytical characterization of the compounds indicated their purity >95% as indicated by UV absorbance at λ=214 nm (Table 4).

The double-substitution library was screened for in vitro agonist activity using the 384-well cAMP based AlphaScreen technology at concentrations ranging from $10^{-4}$ M to $10^{-10}$ M in duplicate replicates with three independent experiments at the mMC1R, mMC3R, mMC4R, and the mMC5R. Since the MC2R is only stimulated by ACTH, it was excluded from this study (Schioth, et al., *Life Sci.* 1996, 59 (10), 797-801). The data were normalized to NDP-MSH, and the response observed for NDP-MSH at $10^{-6}$ M was defined as 100% response. Additional positive (forskolin) and negative (assay buffer) controls were included in the screening. Compounds which failed to produce full dose-response curves at the mMC3R or the mMC4R were further assessed for antagonist activity via a Schild analysis and $pA_2$ values were determined (Schild, et al., *Br. J. Pharmacol.* 1947, 2 (3), 189-206). In a typical antagonist experiment, cells were co-treated with NDP-MSH (full dose-response, $10^{-6}$ to $10^{-12}$ M) and the compound of interest (10,000 nM, 5,000 nM, 1,000 nM, and 500 nM) and the apparent shift in NDP-MSH response was quantified. NDP-MSH was selected over =-MSH since it is a more potent analog (Sawyer, et al., *Proc. Natl. Acad. Sci. U.S.A.* 1980, 77 (10), 5754-8), and NDP-MSH proved to give a more consistent result in the AlphaScreen over the other commonly used potent cyclic MSH analog, MTII. The apparent shifts in NDP-MSH's agonist activity ($EC_{50}$ values) were recorded and a Schild analysis was performed to yield a $pA_2$ value [$pA_2$=-Log($K_i$)] (Schild, et al., *Br. J. Pharmacol.* 1947, 2 (3), 189-206). These experiments were also performed with duplicate well replicates and three independent experiments.

The nine mMC3R agonists with $EC_{50}$'s less than 1,000 nM were selected for radiolabeled $^{125}$I-NDP-MSH binding evaluation at both the mMC3R and mMC4R. It was hypothesized that the results from this experiment would reveal additional insight into the novel pharmacological dual mMC3R agonist/mMC4R antagonist profile that was observed. A typical experiment utilized a 12-well format. The compounds were assayed from 10-4 M to 10-10 M with a constant 100,000 cpm/well of monoiodinated $^{125}$I-NDP-MSH. The data were normalized to the specific binding by a saturating concentration of unlabeled NDP-MSH that was defined as 100%. The $IC_{50}$ value for control peptide (Ac-His-DPhe-Arg-Trp-NH2 (SEQ ID NO:2)) at the mMC3R was fitted by constraining the top and bottom, complete receptor saturation and complete radiolabel displacement, nonlinear regression parameters to those which were determined for NDP-MSH within the same experiment. This allowed for an estimation of the $IC_{50}$ which was needed in order to numerically compare, in terms of fold difference, the observed changes in 1050 potencies within the receptor subtype. The calculated $IC_{50}$ value was 50 μM at the mMC3R, and in agreement with the previously reported 1050 value at the human MC3R ($IC_{50}$>10 μM) which has high receptor sequence homology to the mMC3R (Irani, et al., *Curr. Pharm. Des.* 2004, 10 (28), 3443-3479; Haskell-Luevano, et al., *J. Med. Chem.* 1997, 40 (14), 2133-2139).

Figure 3:
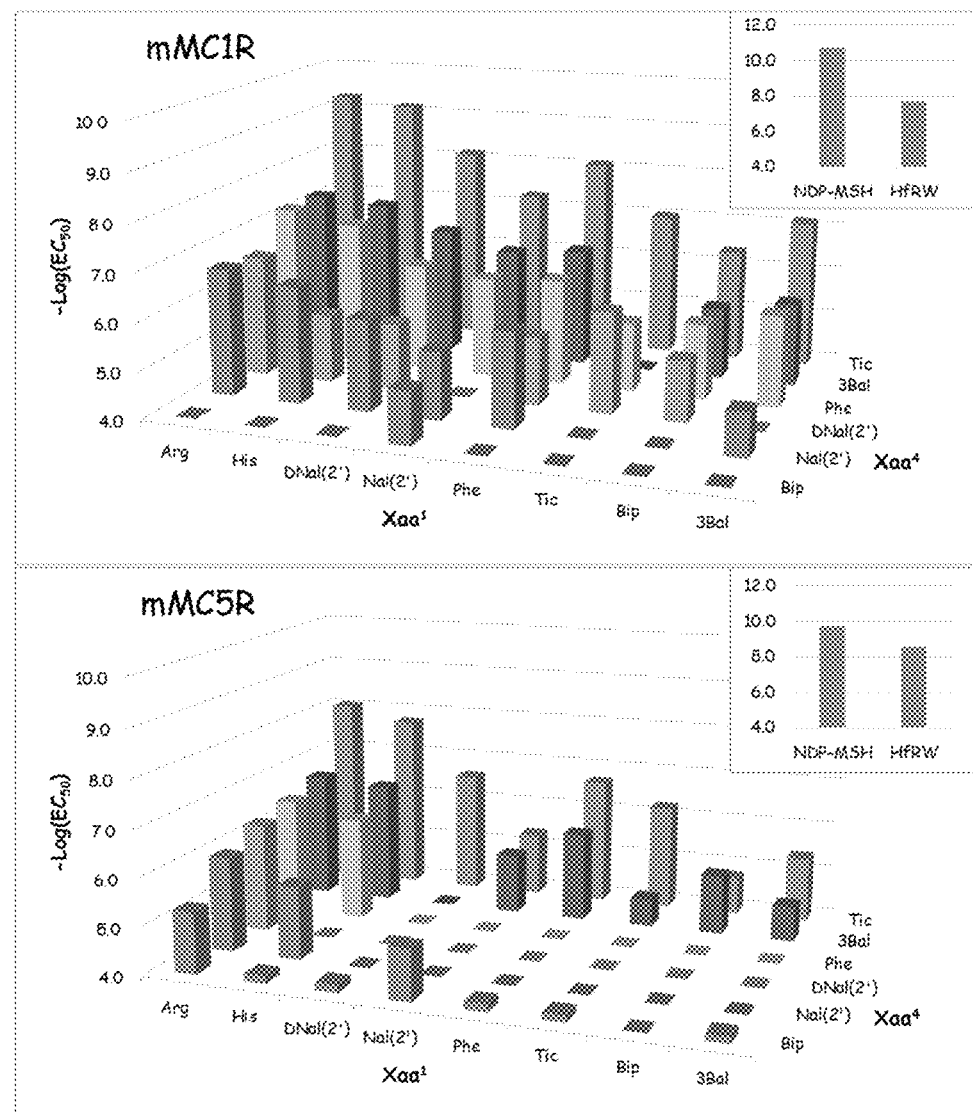
FIG. 3. Summary of agonist activity, $-Log(EC_{50})$, as a function of the first and fourth sidechain substitutions at the mouse melanocortin-1 and -5 receptors for the scaffold Ac-Xaa$^1$-(pI)DPhe-Arg-Xaa$^4$-NH$_2$ (SEQ ID NO:109).
Figure 4:
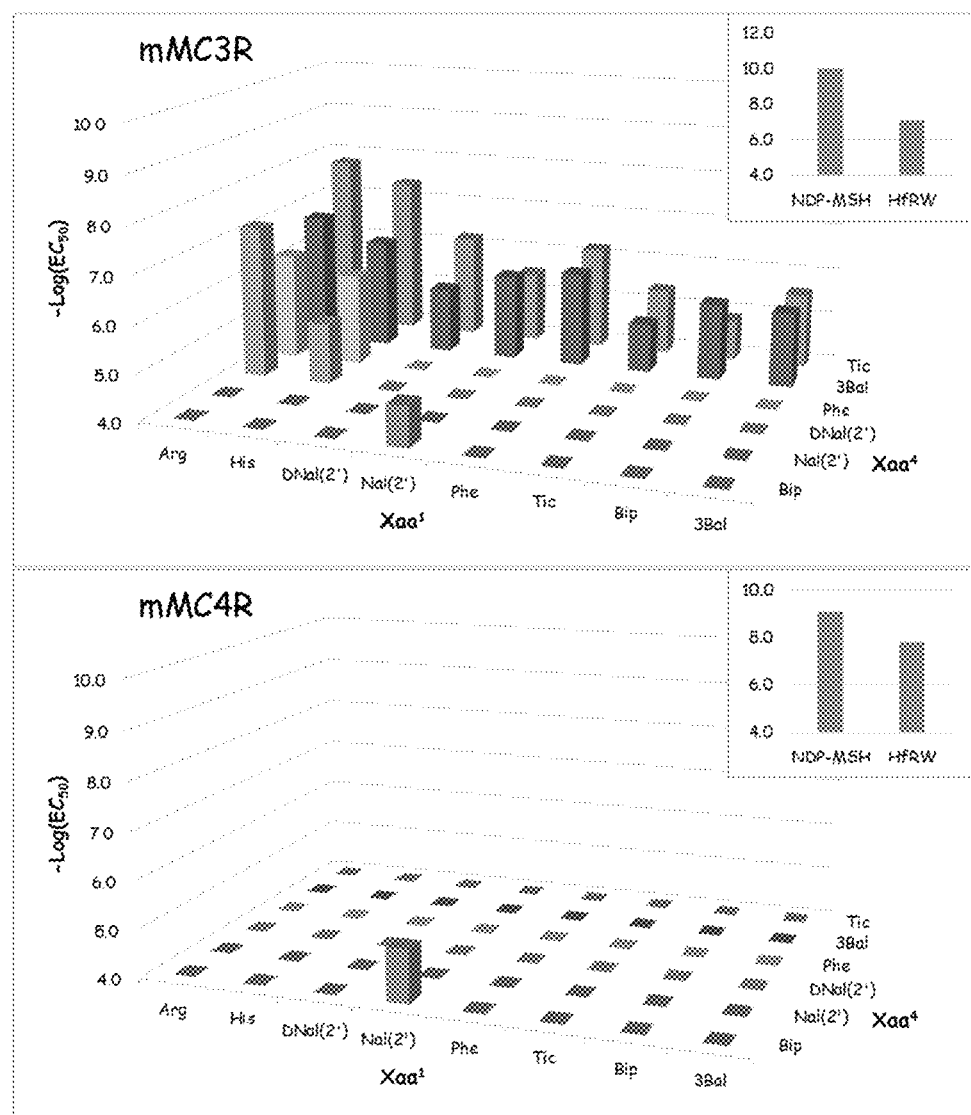
FIG. 4. Summary of agonist activity, $-Log(EC_{50})$, as a function of the first and fourth sidechain substitutions at the mouse melanocortin-3 and -4 receptors for the scaffold Ac-Xaa$^1$-(pI)DPhe-Arg-Xaa$^4$-NH$_2$(SEQ ID NO:109).
Figure 5:
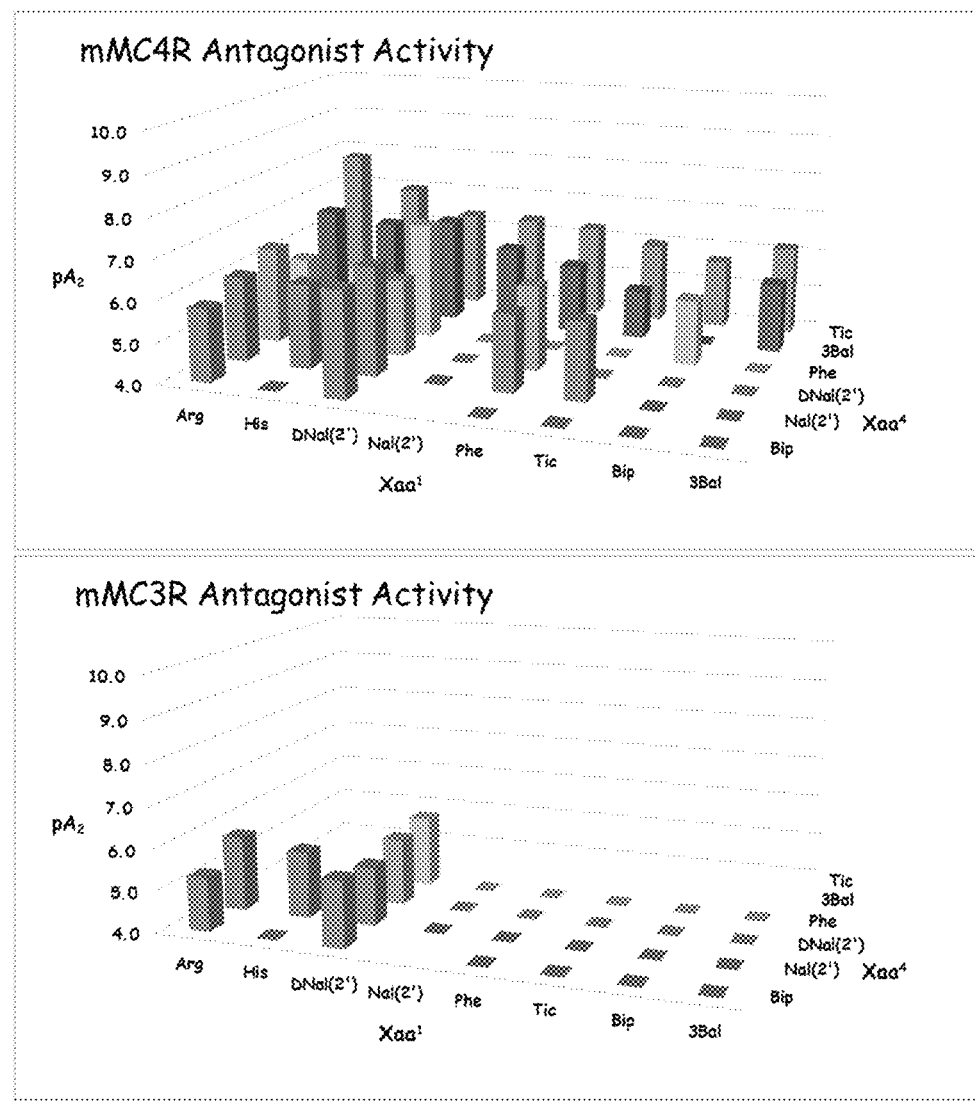
FIG. 5. Summary of antagonist activity, $pA_2$, as a function of the first and fourth sidechain substitutions at the mouse melanocortin-3 and -4 receptors for the scaffold Ac-Xaa$^1$-(pI)DPhe-Arg-Xaa$^4$-NH$_2$(SEQ ID NO:109).

Overview of the SAR Results at the Mouse Melanocortin-1, -3, -4, and -5 Receptors The double-substitution library produced a varied SAR between the receptors at the four selected subtypes which ranged from potent agonists to potent antagonists. Given the large volume of data, they are separated by receptor subtypes with the mMC1R/mMC5R together and mMC3R/mMC4R together. The combined agonist and antagonist results for the mMC3R and mMC4R are tabulated in Table 1 and the agonist results for the mMC1R and mMC5R are tabulated in Table 2. Additional figures illustrate a summary of the agonist and antagonist activity as a function of both substitutions at the first and fourth positions of the TACO scaffold (FIG. 3 for the mMC1R/mMC5R agonist, FIG. 4 for the mMC3R/mMC4R agonist, and FIG. 5 for the mMC3R/mMC4R antagonist data). The most potent agonist activity was observed at the mMC1R, followed by similar agonist activities at the mMC3R and mMC5R, while little to no agonist activity was observed at the mMC4R. As already discussed, compounds demonstrating little to no agonist activity at the mMC3R or the mMC4R were selected for antagonist activity via a Schild analysis (Schild, et al., *Br. J. Pharmacol.* 1947, 2 (3), 189-206). Compounds with antagonist activity at the mMC3R was generally observed to be weak, $pA_2$<6, ($k_i$>1,000 nM) whereas seventeen compounds evaluated at the mMC4R possessed $pA_2$>6 ($K_i$<1,000 nM). Notably lead compound SKY6-24-2 and the closely related compound SKY4-48-18 were observed to be antagonists at the mMC4R with a $pA_2$ greater than 7.0 ($K_i$<100 nM) and potent nanomolar agonists at the mMC3R ($EC_{50}$=40 and 16 nM, respectively). Lastly, compound SKY4-48-42 was observed to be a potent nanomolar agonist at the mMC3R ($EC_{50}$=57 nM) which was 5-fold selective over the mMC1R and 9-fold selective over the mMC5R. In addition, this compound was a 400 nM antagonist at the mMC4R ($pA_2$=6.4).

Discussion

Mixture-Based Positional Scanning Library Deconvolution and Template Selection

A typical study using mixture-based positional scanning libraries begins with a scaffold selection where around 100 scaffolds containing mixtures ranging in number from 10 s of thousands to approximately 750,000 compounds are tested. The most active mixture scaffold is then chosen for deconvolution using the method of mixture-based positional scanning. Herein, we omitted the scaffold ranking and selected a tetrapeptide scaffold since the minimally active sequence of all the POMC derived melanocortin agonists is His-Phe-Arg-Trp (SEQ ID NO:113) and previous studies about this scaffold have demonstrated a variety of SAR can be achieved (Hruby, et al., *J. Med. Chem.* 1987, 30 (11), 2126-2130; Holder et al., *J. Med. Chem.* 2002, 45 (13), 2801-2810; Holder, et al., *J. Med. Chem.* 2002, 45 (26), 5736-5744; 22, 60-61, Holder, et al., *J. Med. Chem.* 2002, 45 (14), 3073-3081; Holder, et al., *Peptides* 2003, 24 (1), 73-82). A positional scanning tetrapeptide library is comprised of a set of systematically arranged sub-libraries representing each position in the scaffold, with fixed amino acids at that position and mixtures at the other three. Thus, there will be four sets of mixtures that enable each of the four positions to be screened to identify the most active functionalities at each of the four positions. Once this has been accomplished, the most active 2-3 different amino acid functionalities, at each of the four positions are then used to make individual tetrapeptides. Reported is what would be considered the minimalist version of the more typical deconvolution experiment.

The peptide sequence, Ac-His-Arg-(pI)DPhe-Tic-NH$_2$ (SEQ ID NO:3), was the sequence corresponding to the highest activity in each position. Out of the total of 60 amino acid building blocks that were incorporated in each of the four positions of the tetrapeptide library, six of those building blocks were used in the first position and four of them were used in the fourth position of the reported TACO template. A comparative analysis of the results obtained from the mixture-based positional scanning library and individual analogues reported herein yield insight into the effectiveness of the high throughput method selected. Analysis of the 24 (6×4) mixtures from the library and corresponding analogues revealed that the most potent MC3R agonists, 2 compounds, would have been identified with the traditional deconvolution of the library results. Furthermore, the individual peptide activity generally corresponded to the library results with the exception of a single outlier, compound Ac-Arg-Arg-(pI)DPhe-DNal(2')-NH2 (SEQ ID NO:43). It is also possible an Arg substitution is favored over the His at the first position. Last, out of the 21 compounds which possessed full agonist activity at the mMC3R, potencies ranging from 16 nM to 14 µM, a total of 10 would have been identified using traditional deconvolution methods while the remaining 11 compounds would not have been part of a traditional deconvolution.

SAR for Agonist Activity

Figure 6A:
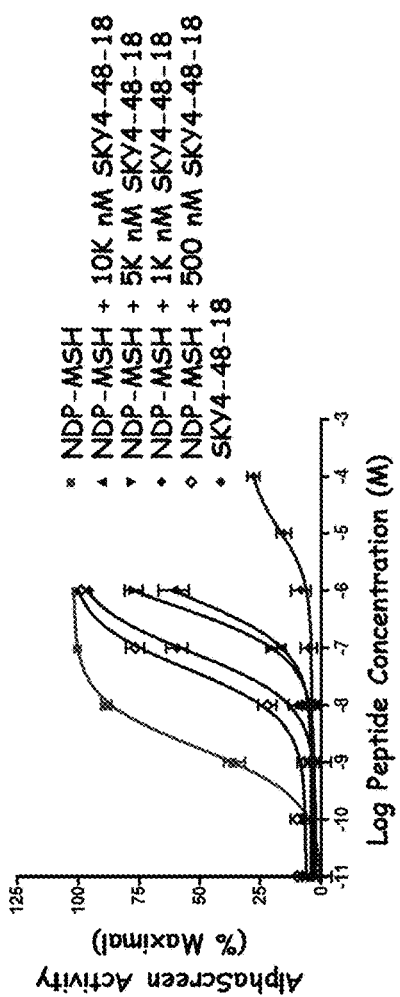
FIGS. 6A-B. Illustration of the pharmacological profile observed for SKY4-48-18 at the selected mouse melanocortin receptors. Compound SKY4-48-18 had a unique pharmacological profile. The compound displayed potent nanomolar agonist activity at the mouse melanocortin-1, -3, and -5 receptor subtypes ($EC_{50}$<20 nM) and strong antagonist activity at the mouse melanocortin-4 receptor subtype ($pA_{2=7.8}$). This compound had the most potent activity out of all of the compounds produced within this study. A total of nine compounds produced moderate to potent agonist activity ($EC_{50}$<1,000 nM) at the mMC3R in addition to producing antagonist activity at the mMC4R (7.8<$pA_2$<5.7).
Figure 6A:
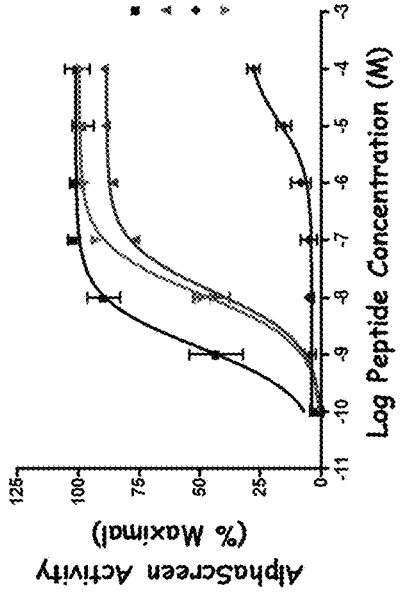

Compounds were most active at the mMC1R, followed by similar activities at the mMC3R and mMC5R, with minimal agonist activity at the mMC4R (FIG. 6A). Results from substitutions at the first position indicate the mMC1R had a preference for a basic side chain (Arg$^1$ and His$^1$), followed by small aromatic sidechains in addition to some intermediate sized aromatics [Phe$^1$, Tic$^1$, DNal(2')$^1$], and last, the remaining intermediately sized aromatics and the bulky aromatics [Nal(2')$^1$, Bip$^1$, 3Bal$^1$] were detrimental to the SAR. This corresponded well to the original positional scanning data, which demonstrated substantially more activity for the Ac-His-X-X-X-NH2 (SEQ ID NO:118) and Ac-Arg-X-X-X-NH2 (SEQ ID NO:119) samples than those corresponding to the other substitutions present in the positional scanning library. Activity at the mMC3R and mMC5R were dependent upon having a basic sidechain at the first position to produce a compound with a potency greater than 100 nM. An aromatic sidechain was tolerable with the addition of either a 3Bal$^4$ or Tic$^4$ substitution at the fourth position and resulted in a moderate (>100 nM) to weak micromolar compound. Interestingly, with the 3Bal$^4$ or Tic$^4$ the trends that were observed with the mMC1R at the first position are consistent with the mMC3R and mMC5R, suggesting the amino acid replacements about this scaffold at the first and fourth position may be additive to the overall activity of the peptide since a step-wise increase in activity was observed when a more favorable substitution was incorporated. This would be compared to observing dramatic increases, several orders of magnitude, upon the incorporation of specific pairs of amino acid substitutions.

The amino acid substitutions at the fourth position produced comparable results for agonist activities at the mMC1, mMC3, and mMC5 receptors. The rank order of the amino acid replacements as a function of their resulting potencies were similar for the three receptor subtypes (Tic$^4$>3Bal$^4$>Phe$^4$=Nal(2')$^4$=DNal(2')$^4$>>Bip$^4$). The constrained Tic$^4$ substitution resulted in the most potent analogs at each of the three receptor subtypes with potencies in the sub- to low-nanomolar ranges (EC$_{50}$<10 nM). Again, this corresponded well to the data from the original positional scanning library screening, where Ac-X-X-X-Tic-NH2 (SEQ ID NO:120) was substantially more active than other samples corresponding to the other substitutions present in the positional scanning library. Compounds containing the sulfur analog of tryptophan, 3Bal$^4$, tended to mirror the potencies observed for the Tic$^4$ analogs, albeit none of these analogs reached sub-nanomolar potencies. Fourth position substitutions that resulted in compounds that fell within an intermediate potency range, high nanomolar to micromolar (EC$_{50}$>500 nM), were the Phe$^4$, Nal(2')$^4$, and DNal(2')$^4$. With these particular substitutions, either an Arg$^1$ or His$^1$ replacement at the first position was required for the analogs to have activity at the mMC3R and mMC5R. Lastly, compounds containing the bulky Bip$^4$ amino acid resulted in the weakest activities with most analogs unable to produce any agonist activity at concentrations up to 100 micromolar.

SAR for Antagonist Activity

The double substitution library resulted in wide-ranging antagonist activity at the mMC4R. When the same compound was assayed for antagonist activity at both the central mMC3 and mMC4 receptors, antagonist activity at the mMC4R tended to be on average 8-fold more potent than the observed potency at the mMC3R, a trend observed for other melanocortin antagonists (Doering, et al., *C.S. Med. Chem. Lett.* 2015, 6 (2), 123-7; Hruby, et al., *J. Med. Chem.* 1995, 38 (18), 3454-3461). Similar to the SAR for the agonist activity at the mMC1, mMC3, and mMC5 receptors, the most active compounds contained a Tic$^4$ substitution, up to pA$_2$=7.8 (K$_i$=16 nM) for SKY4-48-18. The 3Bal$^4$ replacement also decreased antagonist activity with respect to the Tic$^4$ replacement, similar to the observed trend for agonist activity at the MC1R, MC3R and MC5R. For the Phe$^4$, Nal(2')$^4$, and DNal(2')$^4$ substitutions. Either a basic Arg$^1$ or His$^1$ or, interestingly, a DNal(2')$^1$ replacement was needed to achieve maximal antagonist activity (up to pA$_2$=6.9 or K$_i$=126 nM for the DNal(2')$^1$/Phe$^4$ analog SKY4-48-33). The Bip$^4$ substitution was generally detrimental for mMC4R antagonist activity, with only two of those analogs, SKY4-48-2 and SKY5-146-2, able to produce detectable activity (pA$_2$=5.8 and 6.6, respectively). In addition, SKY4-48-8 was the only compound which resulted in agonist activity at the mMC4R for the whole library and possessed weak micromolar potency (EC$_{50}$=7,900 nM).

The most potent mMC4R antagonist, SKY4-48-18, had an Arg$^1$/Tic$^4$ substitution which resulted a pA$_2$ of 7.8 (K$_i$=15 nM); in addition, this compound resulted in nanomolar agonist activity at the mMC3R (EC$_{50}$=16 nM). The antagonist activity at the mMC4R was unexpected since studies on the linear tetrapeptide Ac-His-DPhe-Arg-Trp-NH$_2$ (SEQ ID NO:2) indicate antagonist activity can be conferred through substitutions such as DNal(2') and (pI)DPhe at the second position whereas most substitutions at the first position result in agonist activity (Holder, et al., *J. Med. Chem.* 2002, 45 (13), 2801-2810; Holder, et al., *Med. Chem.* 2002, 45 (14), 3073-3081). A Tic$^1$ replacement at the first position yielded weak antagonists (pA$_2$<6, K$_i$>1,000 nM). This is in contrast to the closely related peptide Tic-(pI)DPhe-Arg-Trp-NH$_2$ which has been reported to strongly bind to both the human MC3R and MC4R (75 and 0.30 nM, respectively), and displays potent antagonist activity at the hMC4R (pA$_2$=9.10, K$_i$=0.79 nM, >35% agonist activation with respect to maximal response) (Ye, et al., *Peptides* 2005, 26 (10), 2017-2025). In addition, a Tic substitution on a SHU9119 analog at the same relative position also resulted in potent antagonist activity (Grieco, et al, *J. Med. Chem.* 2002, 45 (24), 5287-5294). All of this suggests the reported TACO scaffold is not only structurally different from compounds based on the endogenous peptides but also elicits different pharmacology when the same residues are replaced.

$^{125}$I-NDP-MSH Competitive Binding

Reported are the results from the radiolabel competition binding experiments at the mMC3R and mMC4R (Table 3). The selection criteria included the nine mMC3R agonists with potencies less than 1,000 nM (SKY6-24-2, SKY4-48-10, SKY4-48-11, SKY4-48-15, SKY4-48-18, SKY4-48-23, SKY6-24-3, SKY4-48-26, and SKY4-48-42). Table 3 summarizes the results of two independent experiments each containing two replicates per experiment. The results are tabulated as the mean and standard error of the mean for each compound at the mMC3R and mMC4R. Also included in the table is the calculated fold difference in $IC_{50}$ potency based on the value observed for SKY4-48-1; Ac-His-DPhe-Arg-Trp-NH$_2$(SEQ ID NO:2). The $IC_{50}$ value for SKY4-48-1 at the mMC3R was fitted by constraining the top and bottom, complete receptor saturation and complete radiolabel displacement, nonlinear regression parameters to those which were determined for NDP-MSH within the same experiment. This allowed for an estimation of the $IC_{50}$ which was needed in order to numerically compare, in terms of fold difference, the observed changes in $IC_{50}$ potencies within the receptor subtype. The calculated $IC_{50}$ value for SKY4-48-1 is 50 µM at the mMC3R, and this result is in agreement with the previously reported $IC_{50}$ value at the human MC3R ($IC_{50}$>10 µM) which has high receptor sequence homology to the mMC$_3$R (Haskell-Luevano, et al., *J. Med. Chem.* 1997, 40 (14), 2133-9; Irani, et al., *Current Pharmaceutical Design* 2004, 10 (28), 3443-3479).

Figure 6B:
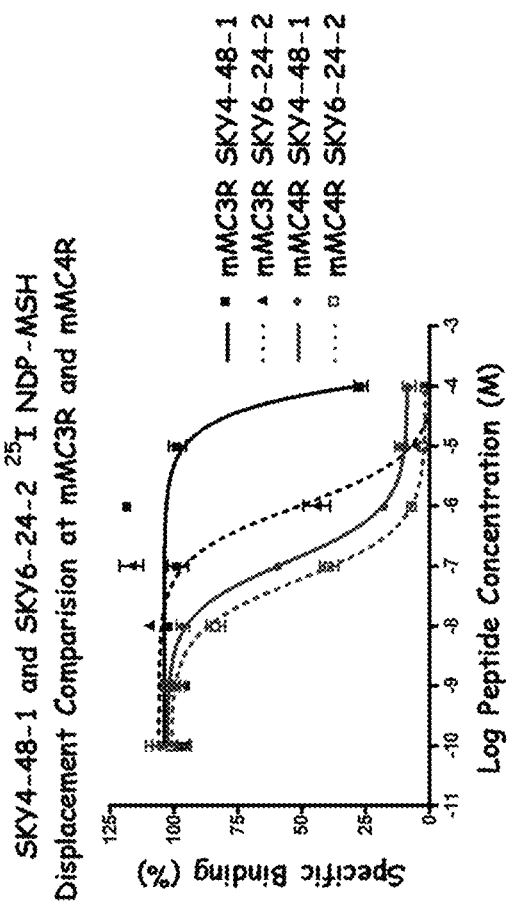
Figure 6B:
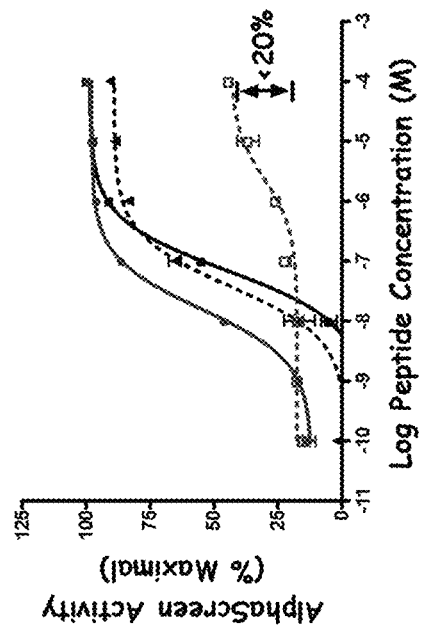

The 9 ligands with $EC_{50}$'s less than 1,000 nM at the mMC3R had binding $IC_{50}$'s less than 5,500 nM. Compared to SKY4-48-1, Ac-His-DPhe-Arg-Trp-NH$_2$(SEQ ID NO:2), the fold decrease in $IC_{50}$ ranged from 9-fold for SKY4-48-15 to 120-fold for SKY6-24-3 ($IC_{50}$=5,350 and 440 nM, respectively). When compared to the mMC3R agonist function data, the binding data generally complement those observed results. That is to say, compounds which possessed nanomolar agonist function activity tended to possess similar results for $IC_{50}$ binding values. All of the compounds were greater binders at the mMC4R over the mMC3R. This result is consistent with the other melanocortin ligands, NDP-MSH and Ac-His-DPhe-Arg-Trp-NH$_2$ (SEQ ID NO:2) (SKY4-48-1) which were included in this study. The binding activity for the selected mMC3R TACOs at the mMC4R tended to be equipotent, $IC_{50}$<3-fold difference, compared to SKY4-48-1 ($IC_{50}$=121 nM). In addition, relative to the greater than 100-fold increases in binding potencies at the mMC3R, the most potent binder at the mMC4R, SKY4-48-18, possessed just a 9-fold increase ($IC_{50}$=13 nM) in binding relative to the tetrapeptide SKY4-48-1. Perhaps the agonist selectivity and nanomolar potencies which were achieved at the mMC3R may be rationalized by the 9- to more than 100-fold increase in binding $IC_{50}$ which was observed relative to the control peptide SKY4-48-1, Ac-His-DPhe-Arg-Trp-NH$_2$ (SEQ ID NO:2) (Table 3, FIG. 6B).

Comparison of the Library to Ac-His-DPhe-Arg-Trp-NH$_2$ (SEQ ID NO:2)

Seven compounds were equipotent to more potent than the tetrapeptide Ac-His-DPhe-Arg-Trp-NH$_2$ (SEQ ID NO:2) at the mMC1R, compared to four at the mMC3R, one at the mMC5R, and none at the mMC4R. In fact, only one compound, SKY4-48-8, was able to produce a maximal response ($EC_{50}$=7,900 nM) at the mMC4R whereas all of the remaining compounds were unable to produce full activity with respect to the full agonists used in this study, NDP-MSH and SKY4-48-1 (Ac-His-DPhe-Arg-Trp-NH$_2$ (SEQ ID NO:2)), at concentrations up to 100 µM. In contrast, 17 members of this library were found to have antagonist activity with pA$_2$ values greater than 6.0 (K$_i$<1,000 nM) at the mMC4R. A prominent outcome for this library was the presence of an mMC3R agonist/mMC4R antagonist pharmacological profile as illustrated with the most potent mMC3R agonist compound SKY4-48-18 (FIG. 6A). A total of 9 compounds produced moderate to potent agonist activity ($EC_{50}$<1,000 nM) at the mMC3R, in addition to producing antagonist activity at the mMC4R (7.8<pA$_2$<5.7). This is in contrast to previous reports on melanocortin tetrapeptides in which the SAR tends to favor MC4R potency over the MC3R (Holder, et al., *J. Med. Chem.* 2002, 45 (13), 2801-2810; Holder, et al., *J. Med. Chem.* 2002, 45 (26), 5736-5744; Holder, et al., *Med. Chem.* 2002, 45 (14), 3073-3081; Holder, et al., *Peptides* 2003, 24 (1), 73-82; Joseph, et al., *The journal of peptide research: official journal of the American Peptide Society* 2005, 66 (5), 297-307; Proneth, et al., *J. Med. Chem.* 2008, 51 (18), 5585-5593; Boeglin, et al., *Chem. Biol. Drug Des.* 2006, 67 (4), 275-83; Todorovic, et al., *J. Med. Chem.* 2005, 48 (9), 3328-3336; Todorovic, et al., *The journal of peptide research: official journal of the American Peptide Society* 2004, 63 (3), 270-8; Holder, et al., *Bioorg. Med. Chem. Lett.* 2003, 13 (24), 4505-4509; Ye, et al., *Peptides* 2005, 26 (10), 2017-2025; Koikov, et al., *Bioorg. Med. Chem. Lett.* 2003, 13 (16), 2647-50).

Is the Ac-Xaa$^1$-Arg-(pI)DPhe-Xaa$^4$-NH$_2$(SEQ ID NO: 110) Scaffold a chimeric AgRP/MC sequence?

The SAR of the new TACO scaffold, Ac-Xaa$^1$-Arg-(pI)DPhe-Xaa$^4$-NH$_2$ (SEQ ID NO:110), relative to the highly conserved endogenous "His-Phe-Arg-Trp (SEQ ID NO:113)" agonist motif has been discussed herein (Hruby, et al., *J. Med. Chem.* 1987, 30 (11), 2126-30). It appears peptides based on the TACO scaffold share few SAR features with melanocortin compounds which are based on the endogenous agonist peptides, and some of the observed pharmacology may be attributed to the unusual reversed Arg-Phe template. However, the possibility cannot be omitted the reported TACO scaffold is a hybrid combination of the AgRP/AISP signaling sequence "Arg-Phe-Phe" and the core melanocortin signaling sequence "His-Phe-Arg-Trp," and this could help rationalize additional aspects of the observed SAR. A chimeric NDP-MSH/AGRP peptide, Ac-Ser-Tyr-Ser-Nle-Glu-His-Arg-Phe-Phe-Gly-Lys-Pro-Val-NH$_2$ (SEQ ID NO:114), is a more potent stimulator for the mMC3R over the mMC4R (480 nM vs 930 nM) (Joseph, et al., *Peptides* 2003, 24 (12), 1899-1908). Moreover, a series of disulfide cyclized chimeric α-MSH/ASIP analogs, template Ac-c[Cys-Arg-(X)Phe-Cys]-(X)Trp-NH$_2$ (SEQ ID NO:115) where X is D or L stereochemistry, are reported to possess hMC3R-selective non-competitive binding (Mayorov, et al., *Peptides* 2010, 31 (10), 1894-1905). The unusual sequence of the TACO scaffold with respect to the endogenous "His-Phe-Arg-Trp (SEQ ID NO:113)" and "Arg-Phe-Phe" sequences gives additional insights into the requirements for receptor recognition and selectivity for the melanocortin subtypes.

Although the TACO scaffold appears to produce a pharmacology that is distinct from the profiles that have been observed for compounds based on the known endogenous ligands, both the mMC3R and mMC4R respond in a similar manner to this scaffold. In other words, substitutions about the scaffold which are beneficial to activity, either agonist or antagonist potencies, for one receptor are beneficial to the other one. The observation is illustrated by plotting the values for each ligand studied as a function of the activities observed at the mMC4R versus the mMC3R (i.e., the absolute magnitude, either agonist EC50 or antagonist Ki values on a log scale, and pharmacological profile as a function of the activities observed at the mMC4R versus the mMC3R). The majority of compounds (39%) possessed pharmacological profiles wherein there was observed agonist activity at the mMC3R and antagonist activity at the mMC4R. This was followed by compounds (33%) that were neither active at the mMC3R nor mMC4R. The remaining compounds had a variety of pharmacology at the two receptor subtypes. If this scaffold tended to favor activity for the mMC4R, one would expect compounds to group in the upper-left quadrant where potencies would be high for the mMC4R and low for the mMC3R. Similar reasoning could be used for the southeast quadrant and compounds that would favor the mMC3R; however, the majority of the compounds fall within the upper-right and lower-left quadrants where either the potencies are both low or both high for the mMC3R and mMC4R.

Conclusions

Herein, a double-substitution library of compounds which were pharmacologically characterized at the mouse melanocortin 1, 3, 4, and 5 receptors is reported. Notably, nine compounds demonstrated agonist activity $EC_{50}$<1,000 nM at the mMC3R, all of which were observed to be competitive antagonists at the mMC4R. These compounds could be used as molecular probes to explore the mechanism with how the melanocortin-3 and -4 receptors synergistically work together to maintain energy homeostasis. Furthermore, this newly discovered TACO scaffold, Ac-Xaa$^1$-Arg-(pI)DPhe-Xaa$^4$-NH$_2$(SEQ ID NO:110) is distinct from the classic His-Phe-Arg-Trp (SEQ ID NO:113) melanocortin template sequence. The unique combination of switching residues and sidechain replacements are required to produce the reported scaffold from the classic signaling sequence.

Experimental Section

Mixture-Based Positional Scanning Library

TPI924 was synthesized as previously described using an optimized solid-phase simultaneous multi peptide synthesis approach on p-methylbenzhydrylamine (MBHA) polystyrene resin (Houghten, et al., *Proc. Natl. Acad. Sci. U.S.A.* 1985, 82 (15), 5131-5135; Ostresh et al., *Biopolymers* 1994, 34 (12), 1681-1689; Tam, et al., *J. Am. Chem. Soc.* 1983, 105 (21), 6442-6455; Houghten, et al., *Int. J. Pept. Protein Res.* 1986, 27 (6), 673-678). The library was constructed using 60 different L-, D-, and unnatural amino acids, which resulted in 240 acetylated tetrapeptide mixtures, each containing 216,000 acetylated tetrapeptides, with a total diversity of 12,960,000 acetylated tetrapeptides. The 60 different amino acids are Ala, Asp, Glu, Phe, Gly, His, Ile, Lys, Leu, Met, Asn, Pro, Gln, Arg, Ser, Thr, Val, Trp, Tyr, DAla, DAsp, DGlu, DPhe, DHis, DIle, DLys, DLeu, DMet, DAsn, DPro, DGln, DArg, DSer, DThr, DVal, DTrp, DTyr, Nle, DNle, Cha, DCha, PyrAla, DPyrAla, ThiAla, DThiAla, Tic, DTic, (pCl)Phe, (pCl)DPhe, (pI)Phe, (pI)DPhe, (pNO$_2$)Phe, (pNO$_2$)DPhe, 2-Nal, 2-DNal, β-Ala, ε-Aminocaproic acid, Met[O$_2$], dehydPro, and (3I)Tyr (Pinilla, et al., *BioTechniques* 1992, 13 (6), 901-905; Dooley, et al., *Life Sci.* 1993, 52 (18), 1509-1517). The compound mixtures were tested without further purification.

Single Tetrapeptide Set of Analogs

The single tetrapeptides described herein were synthesized manually using a combination of microwave-assisted and standard room temperature N-α-Fluorenylmethyloxycarbonyl (Fmoc) solid-phase peptide synthesis on Rink-amide MBHA resin (Peptides International, 0.35 meq/g) (Tala, et al., *Bioorg. Med. Chem. Lett.* 2015, 25 (24), 5708-5711; Stewart, et al., *Solid phase peptide synthesis*. 2nd ed.; Pierce Chemical Co.: Rockford, Ill., 1984; p xvi, 176 p). The peptides were synthesized in parallel in groups of eight compounds. The resin (0.5 mmol scale) was initially swelled in dichloromethane (DCM) for 1 hr. This was followed by resin activation with 15 mL of 20% piperidine in N,N-dimethylformamide (DMF). The reaction was mixed via bubbling the mixture with nitrogen gas for 2 min at room temperature. The reaction vessel was drained, additional 15 mL of 20% piperidine in DMF was added, and the reaction vessel was heated to 75° C. in a microwave (Discover SPS, CEM Corporation) with 30 W power for 4 min. The reaction was allowed to cool and then washed with DMF (3×15 mL). Following a positive ninhydrin test (Stewart, et al., *Solid phase peptide synthesis*. 2nd ed.; Pierce Chemical Co.: Rockford, Ill., 1984; p xvi, 176 p), the Fmoc protected amino acid (3.1 eq), N,N,N',N'-Tetramethyl-O-(1H-benzotriazol-1-yl)uronium hexafluorophosphate (HBTU, Peptides International) (3 eq), and diisopropylethylamine (DIEA, Sigma-Aldrich) (5 eq) were dissolved in DMF and added to the reaction vessel. The vessel was heated to 75° C. in a microwave with 30 W power for 5 min. The amino acid building blocks used in this study were: Fmoc-Arg(Pbf)-OH (Peptides International), Fmoc-3Bal-OH (Bachem), Fmoc-Bip-OH (Synthe Tech), Fmoc-Glu(OtBu)-OH (Peptides International), Fmoc-Gly-OH (Peptides International), Fmoc-His(Trt)-OH (Peptides International), Fmoc-Lys (Boc)-OH (Peptides International), Fmoc-Nle-OH (Peptides International), Fmoc-D-4-I-Phe-OH (AnaSpec), Fmoc-Phe-OH (Peptides International), Fmoc-D-Phe-OH (Peptides International), Fmoc-Pro-OH (Peptides International), Fmoc-Nal(2')-OH (Synthe Tech), Fmoc-D-Nal(2')-OH (Peptides International), Fmoc-Ser(tBu)-OH (Peptides International), Fmoc-Tic-OH (Synthe Tech), Fmoc-Trp(Boc)-OH (Peptides International), Fmoc-Tyr(tBu)-OH (Peptides International), and Fmoc-Val-OH (Peptides International). For coupling Arg the equivalents of the reagents were increased Arg (5 eq), HBTU (5.1 eq), and DIEA (7 eq) as was the microwave coupling time (10 min). For coupling His the microwave temperature was decreased to 50° C. After coupling in the microwave the reaction was allowed to cool and was washed in DMF (3×15 mL).

Following a negative ninhydrin test for primary amines, or a chloranil test for secondary amines, the entire deprotection and coupling procedure was repeated for the remaining residues (Stewart, et al., *Solid phase peptide synthesis*. 2nd ed.; Pierce Chemical Co.: Rockford, Ill., 1984; p xvi, 176 p). After coupling the third amino acid residue, the resin was dried and then divided into eight separate reaction wells. Using a semi-automatic synthesizer (LabTech 1, Advanced ChemTech), the eight resins were swelled in DCM (10 mL, 1 hr, 350 RPM) and then washed in DMF (3×10 mL, 1 min, 350 RPM). The resins were deprotected with 20% piperidine in DMF (10 mL for 2 min, and 10 mL for 18 min). The remaining residue was coupled using the same equivalents as above. The reactions were allowed to couple at RT for 1 hour. Following a negative ninhydrin test for primary amines, or a chloranil test for secondary amines (Stewart, et al., *Solid phase peptide synthesis*. 2nd ed.; Pierce Chemical Co.: Rockford, Ill., 1984; p xvi, 176 p), the resins were deprotected with 20% piperidine in DMF (10 mL 2 min, and 10 mL 18 min at RT), and subsequently acetylated with a 10 mL solution of acetic anhydride and pyridine (3:1) for 30 min at RT. The resin was then washed in DMF (3×10 mL) then again in methanol (1×10 mL) and dried overnight.

The peptides were cleaved from the resin and globally deprotected in parallel. A 10 mL mixture of trifluoroacetic acid (Sigma-Aldrich), thioanisole (Fluka), triisopropylsilane (Aldrich), and water (91:3:3:3) was added to each well and allowed to stir for 1 hour at RT at 350 RPMs. The mixture was drained and collected into 50 mL Falcon tubes. Upon the addition of cold 0° C. diethyl ether a precipitant was formed. The white precipitant was pelleted using a Sorvall Legend XTR centrifuge with a swinging bucket rotor (4,000 RPM, 4° C., 4 min). The pellet was washed with additional diethyl ether and pelleted (3×). The pellet was allowed to dry in a desiccator overnight.

The crude peptides were purified by RP-HPLC with a photodiode array detector (Shimadzu Corp.) on a semi-preparative scale with a flow rate of 5 mL/min on a RP-HPLC C18 bonded column (Vydac 218TP1010, 1 cm×25 cm) in pairs. Mixtures of crude peptides were combined and purified together in order to decrease instrument time and solvent usage. The collected fractions were concentrated on a rotary evaporator and subsequently lyophilized to a fine white powder. The pure compounds were analytically characterized by RP-HPLC using two different solvent systems. The analytical method was either acetonitrile or methanol in a 10% to 90% gradient in 0.1% TFA in water over 35 minutes at a rate of 1.5 mL/min using an analytical Vydac C18 column (Vydac 218TP104, 4.6 mm×25 cm) and purity was monitored by integrating the area under the curve at $\lambda$=214 nm. The mass was confirmed using a matrix-assisted laser desorption/ionization-time of flight mass spectrometer (MALDI-TOF MS) analysis using an $\alpha$-cyano-4-hydroxy-cinnamic acid matrix (AB-Sciex 5800, University of Minnesota Department of Chemistry Mass Spectrometry Laboratory). The control peptides Ac-His-DPhe-Arg-Trp-NH$_2$ (SEQ ID NO:2) and NDP-MSH were synthesized individually using the microwave method described above. These compounds were also purified individually using the same RP-HLPC instruments.

β-Galactosidase Bioassay

This bioassay was implemented for the primary mixture-based positional scanning library TPI924. The ligands described in this study were assayed in HEK293 cells stably expressing the mouse melanocortin-1, -3, -4, and -5 receptor subtypes which were cloned into the cells using a pCDNA3 vector which has been previously described (Doering, et al., *ACS Med.Chem. Lett.* 2015, 6 (2), 123-127). Stably transfected HEK293 cells were plated with media (Dulbecco's Modified Eagle Medium [DMEM] supplemented with 10% Bovine Serum and 1% Penicillin Streptomycin) into a 10 cm dish such that, 24 hours later the cells reached approximately 40% confluency. Twenty-four hours post plating, the cells were transiently transfected with 4 µg CRE-PBKS per 10 cm plate of cells using the calcium phosphate method (Chen, et al., *BioTechniques* 1988, 6 (7), 632-638). Twenty-four hours post transfection, the cells were plated onto collagen treated Nunclon Delta Surface 96-well plates (Thermo Fischer Scientific) and incubated at 37° C. with 5% CO$_2$. Forty-eight hours post transfection, the plates were stimulated with the compound mixtures. The compound mixtures were dissolved in DMF up to a concentration of 1,000 µg/mL and stored at −20° C. until use. The cell media was aspirated and to each well 40 µL of the peptide mixture from TPI924 (100 µg/mL and 50 µg/mL) in assay media (1.0 mL 1% bovine serum albumin [BSA] in phosphate buffered saline [PBS] and 1.0 mL 100× isobutylmethylxanthine in 98.0 mL DMEM). Controls included NDP-MSH (10-6 to 10-12 M), forskolin (10 µM), and plain assay media. The plates were incubated at 37° C. with 5% CO$_2$ for six hours. Post stimulation, the media was aspirated and 50 µL of lysis buffer (250 mM Tris-HCl pH=8.0, 740 mL DD H2O, 10 mL 10% Triton X-100 in water) was added. The plates were stored at −80° C. for up to two weeks.

The plates were thawed, assessed for protein content, and substrate was added to develop the plates. Protein content was assessed by adding, 10 µL of cell lysate was added to 200 µL of BioRad dye solution (1:4 dilution with water) in another 96 well plate, and the absorbance was read using a 96 well plate reader (Molecular Devices) at $\lambda$=595 nm. To the remaining 40 µL of cell lysate, 40 µL of, 37° C., 0.5% BSA in PBS was added in addition to 150 µL of the β-galactosidase substrate (60 mM Na$_2$HPO$_4$, 1 mM MgCl$_2$, 10 mM KCl, 50 mM 2-mercaptoethanol, and 660 µM 2-nitrophenyl β-D-galactopyranoside). The plates were incubated at 37° C. and periodically read on the 96 well plate reader until the absorbance at $\lambda$=405 nm reached approximately 1.0 relative absorbance units for the positive controls. The β-galactosidase activity was normalized to both protein content and maximal response of the positive controls.

AlphaScreen Bioassay

This bioassay was used to produce the dose-response curves and subsequent EC$_{50}$ determination for the reported TACO library. The ligands described in this study were assayed in HEK293 cells stably expressing the mouse melanocortin-1, -3, -4, and -5 receptor subtypes, which were cloned into the cells using a pCDNA3 vector which has been previously described (Haslach, et al., *J. Med. Chem.* 2014, 57 (11), 4615-28). The cAMP signaling was directly measured using the AlphaScreen (Perkin-Elmer, Cat #6760635M) assay protocol as described by manufacturer as previously reported (Tala, et al., *Bioorg. Med. Chem. Lett.* 2015, 25 (24), 5708-5711; Ericson, et al., *Bioorg. Med. Chem. Lett.* 2015, 25 (22), 5306-5308; Singh, et al., *A.C.S. Med. Chem. Lett.* 2015, 6 (5), 568-72). Cells were grown in an incubator at 37° C. with 5% CO$_2$ in cell media [Dulbecco's modified Eagle's medium (DMEM) containing 10% newborn calf serum (NCS) and 1% penicillin/streptomycin] in 10 cm plates to 70-95% confluency the day of the assay.

Cells were disassociated with 1 mL 37° C. Versene solution (Gibco), re-suspended in 5 mL 37° C. cell media, and pelleted by centrifugation at 800 RPM for 5 min at room temperature (Sorvall Legend XTR centrifuge, swinging bucket rotor). The supernatant was subsequently aspirated and the cell pellet was re-suspended in 37° C. Dulbecco's phosphate buffered saline solution (DPBS 1× without CaCl$_2$ or MgCl$_2$, Gibco). The cells were manually counted using a hemocytometer (10 µL cell mixture added to 10 µL of Trypan blue BioRad dye). The cells were again centrifuged (800 RPM, 5 min, RT) and the supernatant was aspirated. The cell pellet was then re-suspended in a solution of freshly made stimulation buffer [Hank's Balanced Salt Solution (HBSS 10× without NaHCO3 or phenol red, Gibco), 0.5 mM isobutylmethylxanthine (IBMX), 5 mM HEPES buffer solution (1 M, Gibco), 0.1% bovine serum albumin (BSA) in Milli-Q water, pH=7.4] to a final concentration of 10,000 cells/µL.

A solution of cells and anti-cAMP acceptor beads in stimulation buffer was then prepared (1,000 cells/µL and 0.5 µg/µL AlphaScreen anti-cAMP acceptor beads in stimulation buffer). The 10 µL of the cell/acceptor bead solution was then added each well in a 384-well microplate (OptiPlate-384, Perkin-Elmer). To each well an additional 5 μL of ligand was added and the concentration of the ligand was adjusted such that the final concentration in the well reflected the desired concentration. The plate was then sealed and incubated at room temperature in the dark for two hours. Compounds included on each plate were NDP-MSH ($10^{-6}$ to $10^{-12}$ M), forskolin ($10^{-4}$ M), and stimulation buffer alone (blank control). The compounds described in this study were initially assayed from $10^{-4}$ to $10^{-10}$ M and the range was adjusted accordingly in later experiments.

The light sensitive biotinylated cAMP/streptavidin coated donor bead mixture in lysis buffer was prepared, 30 min prior to the end of the initial two hour plate incubation, under green light (0.5 μg/μL AlphaScreen donor beads and 0.62 μM AlphaScreen cAMP biotinylated tracer in a solution of 10% Tween-20, 5 mM HEPES, and 0.1% BSA in Milli-Q water, pH=7.4). Post the initial plate incubation, 10 μL of the biotinylated cAMP/streptavidin donor bead lysis buffer was added to each well under green light. The plate was resealed, covered with aluminum foil, and incubated for a second two hour incubation in the dark. After incubation, the plate was read via an EnSpire Alpha Plate Reader (Perkin-Elmer) using a protocol preset by the manufacturer. The data were fitted with dose-response curves and $EC_{50}$ values were calculated by a nonlinear regression using GraphPad Prism (v4.0) software.

$^{125}$I-NDP-MSH Preparation and Purification

NDP-MSH was monoradioiodinated for the use in competition binding assays. The peptide was radioiodinated with Na$^{125}$I using the previously described chloramine T procedure (Hunter, et al., *Nature* 1962, 194 (4827), 495-496). The monoradioiodinated peptide was resolved from the uniodinated and diradioiodinated peptide via RP-HPLC using a C18 reverse phase column eluted isocratically with an acetonitrile:trimethylamine phosphate (pH 3.0) mobile phase. The column eluate containing the monoradioiodinated peptide was diluted in a solvent mixture (2 parts 24% acetonitrile: 76% triethylamine phosphate, pH 3.0:1 part milliQ water) containing a 2 mg/mL bovine albumin stabilizer. The resulting yield (lot number: 150326A) was 1.9 mL contining 1126 pfi of monoiodinated NDP-MSH with a theoretical specific activity of 2175 Ci/mmol. The radioligand was stored at −80° C. in a lead pig until use.

$^{125}$I-NDP-MSH Competitive Binding Assay

This bioassay was used to produce the dose-response curves and subsequent $IC_{50}$ determination for selected compounds from the reported TACO library (the 10 most potent $EC_{50}$ values at the mMC3R) at the mMC3R and mMC4R. The HEK293 cells stably transfected with the selected mouse melanocortin receptors, as described above, were used in this assay. Cells were plated into 12-well treated polystyrene plates (Corning Life Sciences, Cat. #353043) 48-hours prior to the binding experiment such that each well reached greater than 90% confluency the day of the assay. On the day of the assay, media was aspirated and a 500 μL solution of 0.1% BSA in DMEM containing the experimental compound ($10^{-4}$ to $10^{-10}$ M) and a constant 100,000 cpm/well $^{125}$I NDP-MSH were added to each well. The plates were incubated at 37° C. with 5% $CO_2$ for 1 hour. Post incubation, the media was aspirated, each well was washed with 500 μL assay media, and cells were lysed with 500 μL of 0.1 M NaOH and 500 μL of 1% Triton x-100.

Following a 10-15 minute room temperature incubation, the cell lysate mixture was transferred to 12×75 mm polystyrene tubes and the radioactivity was quantified using a WIZARD$^2$ Automatic Gamma Counter (Perkin-Elmer). The specific binding for each well was determined by subtracting the counts obtained from the cell lysate which was incubated with the non-radioactive $10^{-6}$ M NDP-MSH. Each experiment included the experimental determination of the specific binding for NDP-MSH as a positive control. The specific binding for each compound was normalized to 100% relative to the specific binding determined for non-radiolabeled NDP-MSH. The data were analyzed using GraphPad Prism (v4.0; GraphPad, Inc), and dose-response curves in addition to the corresponding $IC_{50}$ values were calculated by a non-linear regression method. Each reported value represents the mean and standard error of the mean (SEM) of, at least, two independent experiments each containing two experimental replicates.

EXAMPLE 2

Retro Inversion of a Potent Melanocortin Tetrapeptide Agonist Compound (TACO) Produces a Selective (Greater Than 100-Fold) Melanocortin-3 Receptor Antagonist As discussed herein, there is an unmet need in the field to identify more drug-like melanocortin ligands that are selective for the MC3R over the MC4R. Concisely, the rationale for this is to develop compounds that could fully elucidate the function of the MC3R in an in vivo system where everything is present. These compounds could potentially be utilized as therapeutics addressing weight management and overall energy homeostasis, which are devoid of the side effects, such as hypertension, that are observed with the administration of MC4R selective compounds (Greenfield, et al., *New Engl J Med* 2009, 360 (1), 44-52).

Example 1 discussed the identification of a first-in-class melanocortin tetrapeptide ligand, wherein the results from an in vitro whole cell intracellular cAMP accumulation assay indicated the tetrapeptide SKY6-24-2, Ac-His-Arg-(pI)DPhe-Tic-NH$_2$(SEQ ID NO:3), was an agonist at the mMC3R and an antagonist at the mMC4R ($EC_{50}$=40 nM and pA$_2$=7.0, respectively). Using the TACO template, Ac-Xaa$^1$-Arg-(pI)DPhe-Xaa$^4$-NH$_2$ (SEQ ID NO:110), a double substitution library was constructed. Eight amino acid substitutions at the first position and six amino acid substitutions at the fourth position resulted in 48 (8×6) individual compounds. The general result observed from the intracellular cAMP accumulation and the $^{125}$I-NDP-MSH radiolabel binding assays indicated the potency at both the mMC3R and the mMC4R could be tuned; however, attempts to achieve selectivity for either the mMC3R or the mMC4R proved futile. Even so, nanomolar activity at both receptor subtypes was observed. Since the desired potency had been achieved, albeit without receptor subtype selectivity, a chemotopographical study on the TACO scaffold was performed to better understand the requirements for each of the receptor subtypes with the hope that selectivity could be developed at each of the receptors.

The TACO scaffold contained a key structural difference from the conserved melanocortin signaling sequence His-Phe-Arg-Trp wherein the Phe and Arg residues were in a reversed order. It was postulated by studying the Arg-Phe structural motif, both the sequence order and chemical topology of the sidechains, ligands specifically targeting the mMC3R and having diminished activity at the mMC4R could be identified. Reported in this Example is the identification of a selective MC3R antagonist with no detectable agonist/antagonist activity at the MC4R.

Library Design

Based upon the observed SAR profile for the TACO scaffold and the lead tetrapeptide SKY6-24-2, Ac-His-Arg-(pI)DPhe-Tic-NH$_2$(SEQ ID NO:3), it was hypothesized that the resultant activity may be due to the amino acid positions which were held constant among all members of the compound library. These were the Arg$^2$ and (pI)DPhe$^3$ substitutions along the tetrapeptide sequence. Relative to the endogenous melanocortin signaling sequence "His-Phe-Arg-Trp," the arginine and substituted phenylalanine residues were in the reversed order. It was speculated that the Arg-(pI)DPhe dipeptide sequence was a new melanocortin pharmacophore.

Thus, two separate but related compound libraries were designed to probe the importance of the side chain positions (sequence) in addition to the relative orientation (D vs. L) of the side chains. It was postulated these chemotopographical studies would produce different molecular requirements for each of the receptor subtypes, and ultimately, the desired selectivity could be achieved without sacrificing ligand potency.

The first library consisted of α-MSH and NDP-MSH analogs in addition to two melanocortin tetrapeptide ligands, sequence Ac-His-(X)DPhe-Arg-Trp-NH$_2$ (SEQ ID NO:116) where X is an hydrogen or iodine replacement. The analogs reversed the sequence of the (D or L)Phe$^7$ and Arg$^8$ (using α-MSH numbering) residues. This made for a total of eight compounds. It was hypothesized that a loss of activity would indicate the TACO scaffold is a unique pharmacophore, different from the core melanocortin signaling motif and could be exploited in the generation of receptor selective ligands.

Figure 7:
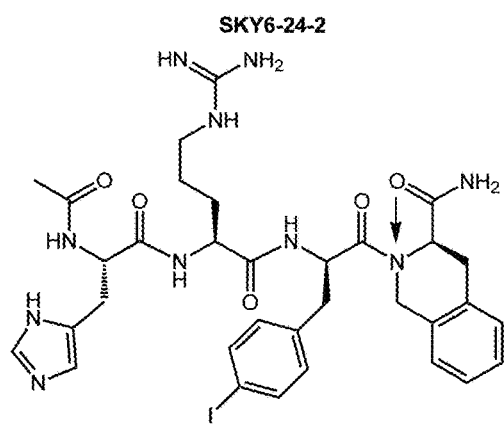
FIG. 7. SKY6-24-2 and the Retro-Inverso Isomers. Illustration of how SKY6-24-2 and the corresponding retro-inverso isomers possess similar spatial orientation of the residue sidechains when SKY6-24-2 is drawn with the backbone going from the N termini to C termini and the retro-inverso isomer analogs are drawn with their backbone in the opposite C termini to N termini orientation.
Figure 7:
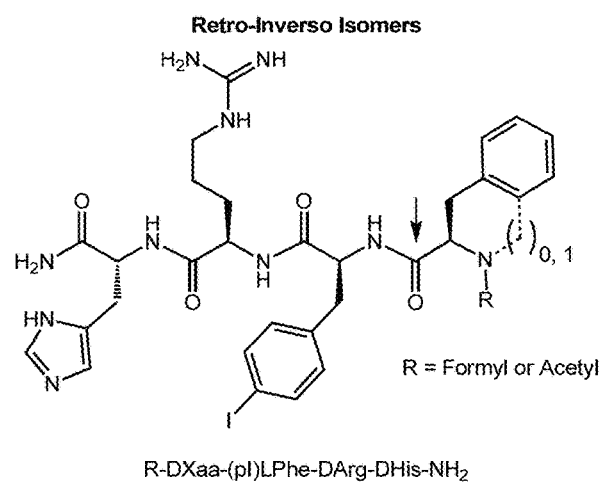

The second library consisted of retro-inverso analogs of the lead TACO peptide SKY6-24-2. With this library the relative three dimensional orientation of the Arg and Phe sidechains would be conserved. However, the amide backbone would be presented in the reversed orientation (FIG. 7). By definition, a retro-inverso isomer is a peptide where the direction of the sequence is reversed and the chirality of each of the sidechain stereocenters are switched (Goodman, et al., *Acc. Chem. Res.* 1979, 12 (1), 1-7). Relative to the parent peptide, a retro-inverso isomer has a similar three dimensional orientation of the sidechains, with exception of the end groups, and the amide backbone is reversed. It has been postulated this type of peptide modification increases enzymatic stability and therefore prolongs the action of a peptide with minimal disturbance to the orientation of the sidechain functionalities; however, in practice, this type of modification often results in peptides which are enzymatically stable but ligand potency is catastrophically sacrificed (Goodman, et al., *Acc. Chem. Res.* 1979, 12 (1), 1-7; Chorev, et al., *Acc. Chem. Res.* 1993, 26 (5), 266-273; Chorev, et al., *Science* 1979, 204 (4398), 1210-1212). Yet, the retro-inversion of the TACO scaffold would resemble, in sequence, the endogenous melanocortin signaling motif.

Studies on the melanocortin ligands indicate the receptors are able to accommodate retro-inverso isomers in addition to other closely related isomers including the all D-pentapeptide of α-MSH(5-9) and the complete retro-inverso analog of α-MSH (Weeden, et al., *J. Pept. Sci.* 2011, 17 (1), 47-55; Hano, et al., *Biochimica et Biophysica Acta (BBA)-General Subjects* 1964, 90 (1), 201-204). However, additional reports indicate some melanocortin scaffolds are sensitive to backbone modification. A series of naphthalene and indole containing peptides with reduced amide backbone was reported to possess modest micromolar binding affinities (Mutulis, et al., *Bioorg. Med. Chem. Lett.* 2002, 12 (7), 1035-1038). In addition, a polyamine, fully reduced, melanocortin peptide with the sequence Phe-DPhe-Arg-Trp-NH$_2$, which was a weak antagonist at both the mMC3R and mMC4R, has previously been reported (Todorovic, et al., *The journal of peptide research: official journal of the American Peptide Society* 2004, 63 (3), 270-8). Furthermore, a study on a library of fully reduced peptides with sequences derived from a mixture-based positional scan deconvolution is being conducted and preliminary results indicating micromolar intracellular cAMP accumulation at the mMC3R and mMC4R. Taking all of these results, it was postulated that the retro-inverso isomer of the tetrapeptide Ac-His-Arg-(pI) DPhe-Tic-NH$_2$ (SEQ ID NO:3) would retain activity since it would contain a Phe and Arg sequence similar to the core melanocortin signaling motif, "His-Phe-Arg-Trp" (FIG. 7). In addition, if the Phe and Arg dipeptide sequence presented itself similar to the melanocortin peptides, which contain the core signaling motif, then the amide bond backbone would have the same orientation as those active ligands.

Relative to the parent compound, Ac-His-Arg-(pI)DPhe-Tic-NH$_2$(SEQ ID NO:3), the retro-inverso isomer, Ac-DTic-(pI)LPhe-DArg-DHis-NH$_2$(SEQ ID NO:61), contains several spatial imperfections that do not allow for the isomers to perfectly superimpose over each other, and some of these potential issues were addressed in the library design (FIG. 7). The first design consideration in the library is the end group problem wherein the N terminal acetyl group and the C terminal amide are not palindromic with respect to each other. To produce a mimetic for the C terminal amide, the N terminal of the retro-inverso compounds were synthesized to contain either an N terminal acetyl or less bulky formyl groups (FIG. 7). The second design consideration addressed in the construction of the retro-inverso library was the spatial imperfection introduced by the backbone constrained Tic side chain. Since the nitrogen atom within the 1,2,3,4-tetrahydroisoquinoline heterocycle is part of the peptide backbone, the Tic residue on the retro-inverso isomer has moved by one bond relative to the parent isomer (FIG. 7). This issue was addressed by synthesizing the retro-isomer containing the correct DTic$^1$ substitution, in addition to an analog containing a DTic$^1$ to DPhe$^1$ replacement which could allow for the aromatic functionality of the DPhe residue to adopt a confirmation mimicking the orientation of the Tic$^4$ residue on the parent compound Ac-His-Arg-(pI) DPhe-Tic-NH$_2$(SEQ ID NO:3).

Results and Discussion
Library Synthesis

All compounds were synthesized by microwave assisted standard Nα-fluorenylmethyloxycarbonyl (Fmoc) solid phase peptide synthesis (SPPS) on Rink amide MBHA resin using N,N,N',N'-tetramethyl-O-(1H-benzotriazol-1-yl)uronium hexafluorophosphate (HBTU) and diisopropylethylamine (DIEA) coupling conditions (Stewart, et al., *Solid phase peptide synthesis*. 2nd ed.; Pierce Chemical Co.: Rockford, Ill., 1984; p xvi, 176 p; Fields, et al., *Int. J. Pept. Protein Res.* 1990, 35 (3), 161-214). Resin (0.1 mmol scale) was swelled in dichloromethane (DCM) and activated in a 20% solution of piperidine in N,N-dimethylformamide (DMF). An Nα-Fmoc amino acid possessing a trifluoroacetic acid labile sidechain (3.1 eq), HBTU (3 eq), and DIEA (5 eq) dissolved in DMF were added to the activated resin and coupled with microwave assistance (75° C., 30 W, 5 min). Completion of the reaction was qualitatively monitored by a Kaiser test for the presence of a primary amine, and the chloranil test was utilized for the presence of a secondary amine (Stewart, et al., *Solid phase peptide synthesis*. 2nd ed.; Pierce Chemical Co.: Rockford, Ill., 1984; p xvi, 176 p). After reaction completion, the Na-Fmoc was removed with 20% solution of piperidine in DMF. The reaction was stirred with nitrogen bubbles for 2 min at room temperature and drained. Additional Fmoc deprotection solution was added to the reaction vessel and was reacted using microwave assistance (75° C., 30 W, 4 min). The coupling and deprotection cycles were repeated in an iterative manner until the peptide was completed. The peptide was either acetylated by a 1:3 mixture of pyridine and acetic anhydride or formylated by a 1:1 mixture of formic acid and acetic anhydride which in situ formed the mixed anhydride and then preferentially formylated the free amine (30 min, room temperature). Note, the addition of formic acid to acetic anhydride is exceedingly exothermic and the formation of the mixed anhydride should be performed at 0° C. Following the final capping, either formylation or acetylation, the resin was washed in DMF, DCM, and MeOH. The final wash in MeOH shrinks the resin and produces a less clumpy resin after drying so it is easier to mass.

The completed peptides were globally deprotected and cleaved from the resin using a cleavage solution of TFA: thioanisole:water:triisopropylsilane (91:3:3:3) stirred, via nitrogen bubbles, for two hours at room temperature. The peptide/cleavage mixture was collected and precipitated upon the addition of 0° C. diethyl ether. The precipitant was pelleted and supernatant was discarded (Sorvall, swinging bucket rotor, 4° C., 4K RPM, 4 min). The pellet was washed in additional ether and pelleted three times, and the pellet was dried overnight under a vacuum in a desiccator.

The compounds were purified by reverse phase high pressure liquid chromatography (RP-HPLC) on a semi-preparative scale (Vydac 218TP1010, 1 cm×25 cm) to a purity greater than 95% (absorbance at $\lambda$=214 nm). The purified compounds were lyophilized to a fine white powder and analytically characterized. They were assessed for purity by analytical (10 micron, 4.6×250 mm, Vydac) RP-HPLC using two solvent systems. Additionally, the mass of the compounds were confirmed by matrix-assisted laser desorption/ionization-time of flight (MALDI-TOF) mass spectrometry (University of Minnesota Spectrometry Laboratory). A summary of the collected analytical data is available in Table 7.

AlphaScreen Assay

Figure 8:
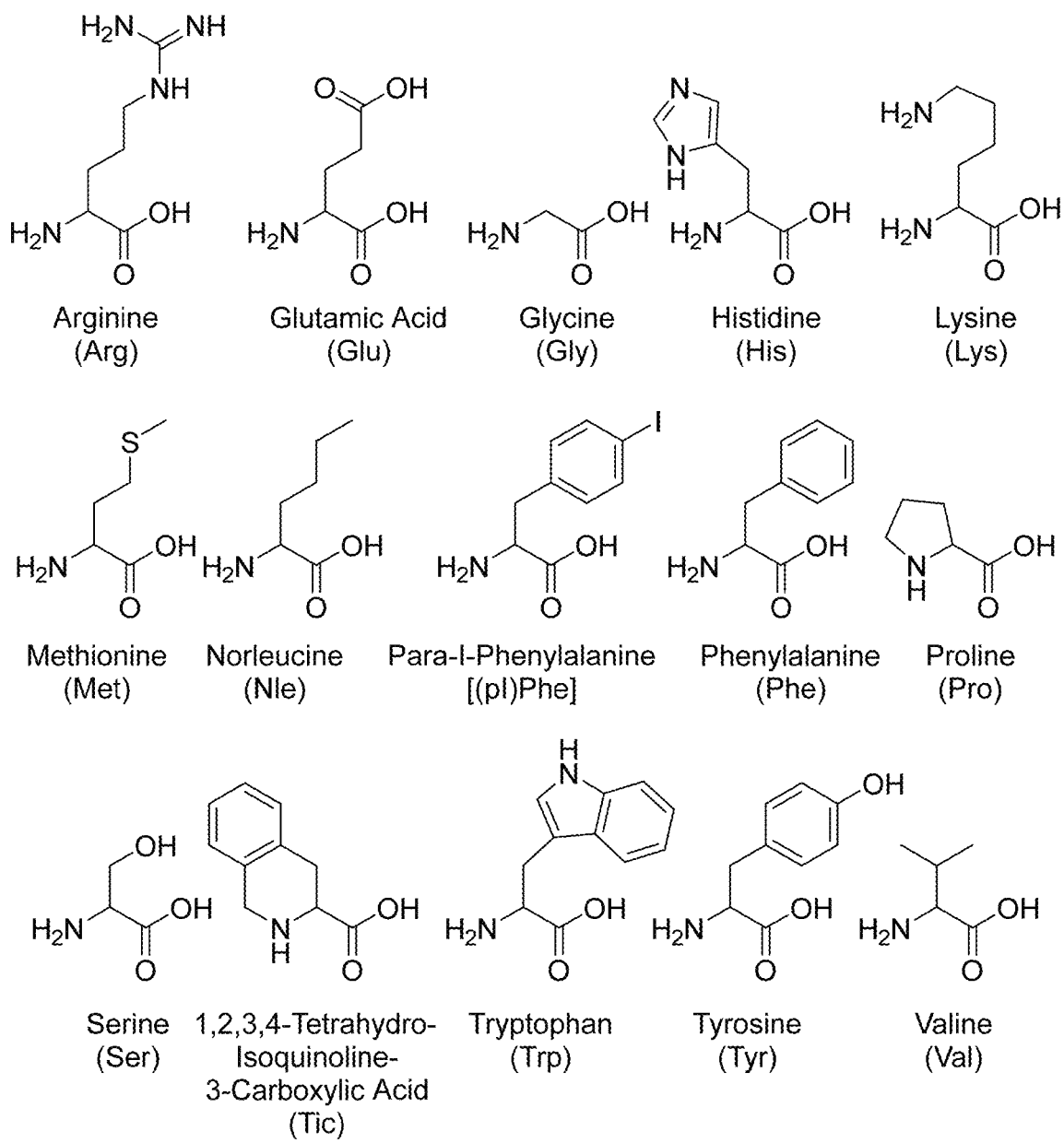
FIG. 8. Amino Acid Building blocks.

All of the analogs were assessed for agonist activity through direct measurement of cAMP intracellular accumulation via the AlphaScreen cAMP assay (Perkin-Elmer) at concentrations up to 100 μM in HEK293 cells stably expressing the mouse MC1, 3, 4, and 5 cloned receptors. Briefly, the cells were stably transfected with a plasmid containing the clone receptor, a pcDNA$_3$ vector, and G418 selection. In a 384-well format, cells, AlphaScreen acceptor beads with anti-cAMP antibodies, and compound were mixed and incubated. Post incubation, light sensitive AlphaScreen cANIP coated donor beads and lysis buffer solution was added to each well and incubated. The response was read using an Enspire (Perkin-Elmer) plate reader using the manufactures' preset protocol. The presence of intracellular cAMP caused a dissociation of the acceptor/donor bead complex, loss of energy transfer via a high energy singlet oxygen species, and the subsequent loss of signal was observed. Each plate contained NDP-MSH, forskolin, and basal controls. The complete experimental details are described below (experimental section). If compounds failed to achieve a full dose-response at the mMC3R or mMC4R, they were assessed for antagonist activity where compounds were co-dosed with the potent melanocortin analog NDP-MSH, and any apparent shifts in EC$_{50}$ for NDP-MSH were recorded and a Schild analysis was performed to produce a pA$_2$ value [pA$_2$=−Log(K$_i$)] (Schild, et al., *Br. J. Pharmacol.* 1947, 2 (3), 189-206). The results from this study are tabulated in Table 5; in addition, the amino acid building blocks used in this study are illustrated in FIG. 8. The complete experimental protocol is available in Example 1.

$^{125}$I-NDP-MSH Radiolabel Binding Assay

The retro-inverso compounds SKY5-122-1 and SKY5-122-2 were selected for radiolabel binding experiments at the mMC3R and mMC4R. In addition, NDP-MSH and SKY4-48-1, Ac-His-DPhe-Arg-Trp-NH$_2$ (SEQ ID NO:2), were included for assay controls and reference purposes. The compounds were assessed for their ability to competitively displace radiolabeled $^{125}$I-NDP-MSH. Briefly, cells stably expressing the cloned receptor subtypes were plated in a 12-well format, and the experimental compounds were assayed from 10$^{-4}$ to 10$^{-10}$ M in the presence of a constant 100,000 cpm/well $^{125}$I-NDP-MSH. Upon washing and cell lysis, the radioactivity for each well was determined using a WIZARD2 Automatic Gamma Counter (Perkin-Elmer). From these data, the specific binding was experimentally determined and a corresponding IC$_{50}$ value was calculated. Note each reported value represents the mean and standard error of the mean (SEM) of at least two independent experiments containing two experimental replicates. The complete experimental details for this assay are in Example 1. The results from the experiments are tabulated in Table 6 and illustrations of the specific binding curves are in FIG. 10.

Reversing the Phe Arg Pharmacophore (Scaffold 1)

At the mMC3R, α-MSH had an EC$_{50}$ value of 0.13 nM while the corresponding (Arg$^7$, Phe$^8$) α-MSH reverse analog yielded 45,000-fold decreased potency (5,800 nM). A similar decrease in potency was observed for NDP-MSH and the corresponding (Arg$^7$, DPhe$^8$) NDP-MSH reverse analog (0.05 nM and 1,800 nM, respectively). There were similar results, ranging from 21,000- to 45,000-fold decreased potency, observed for α-MSH, NDP-MSH, and their Arg-Phe reversed analogs at the mMC1, mMC4, and mMC5 receptors; however, switching the DPhe-Arg residues in the tetrapeptide Ac-His-DPhe-Arg-Trp-NH$_2$(SEQ ID NO:2) to Ac-His-Arg-DPhe-Trp-NH$_2$ (SEQ ID NO:55) was not as detrimental to the potency at some of the receptors.

The well-studied CHL-tetrapeptide Ac-His-DPhe-Arg-Trp-NH$_2$ (SEQ ID NO:2) is a potent agonist at all four of the selected melanocortin receptor subtypes (20, 73, 16, and 3.0 nM, for the mMC1, 3, 4, and 5 receptors, respectively) and the corresponding reverse analog SKY5-146-6, Ac-His-Arg-DPhe-Trp-NH$_2$(SEQ ID NO:55), yielded micromolar agonists at the mMC1, mMC3, and mMC5 receptors and no agonist activity up to concentrations of 100 μM at the mMC4R. The closely related halogenated tetrapeptide Ac-His-(pI)DPhe-Arg-Trp-NH$_2$(SEQ ID NO:57), CJL-1-20, and the reverse analog SKY5-146-7 yielded a similar pharmacological pattern.

The reverse analog of Ac-His-(pI)DPhe-Arg-Trp-NH$_2$ (SEQ ID NO:57), SKY5-146-7, and the lead compound SKY6-24-2 differ by a Trp$^4$ to Tic$^4$ substitution, and this Trp$^4$ to Tic$^4$ replacement resulted in a 380-fold increase in potency at the mMC1R, a 12-fold increase in potency at the mMC3R, a complete elimination of agonist potency at the mMC4R, and a 40-fold increase in potency at the mMC5R. This suggests for tetrapeptides the reverse in the Phe and Arg may be detrimental to activity, yet agonist activity at the mMC1, 3, and 5 receptors can be rescued with an amino acid replacement at the fourth position which results in centrally selective MC3R agonists. It can be envisioned the double substitution library reported above is simply a combination phenylalanine/arginine reversal and fourth position replacement of the previously reported melanocortin ligands. This modification could be used to produce additional MC3R agonists from previously reported melanocortin tetrapeptides and pentapeptides.

Retro-Inversion of TACO Tetrapeptides (Scaffold 2)

The four retro-inverso analogs (SKY5-122-1, SKY5-122-2, SKY5-142-A, and SKY5-148) of Ac-His-DPhe-Arg-Trp-NH$_2$ (SEQ ID NO:2) (SKY4-48-1), with sidechains arranged in a similar chemical topology to the parent compound but with reversed amide bond backbone, produced little to no measureable agonist activity up to concentrations of 100 µM at all four of the selected receptor subtypes (Table 5). These results are consistent with a previous report (Weeden, et al., *J. Pept. Sci.* 2011, 17 (1), 47-55). The small library of retro-inverso compounds of the lead peptide SKY6-24-2, Ac-His-Arg-(pI)DPhe-Tic-NH$_2$(SEQ ID NO:3), which investigated different terminal modifications and backbone constrained amino acids and their effects on retro-inverso analogs, produced no little to no agonist activity at the mMC3, mMC4, and mMC5 receptors yet were relatively potent inverse agonists at the mMC1R, although, additional experiments would be required at the mMC1R to confirm the observed activity (Table 5). Subsequent antagonist analysis for the compounds at the mMC3R/mMC4R subtypes, in addition to, the specific binding determination for two of the retro-inverso compounds, SKY5-122-1 and SKY5-122-2, yielded exciting results.

Figure 9:
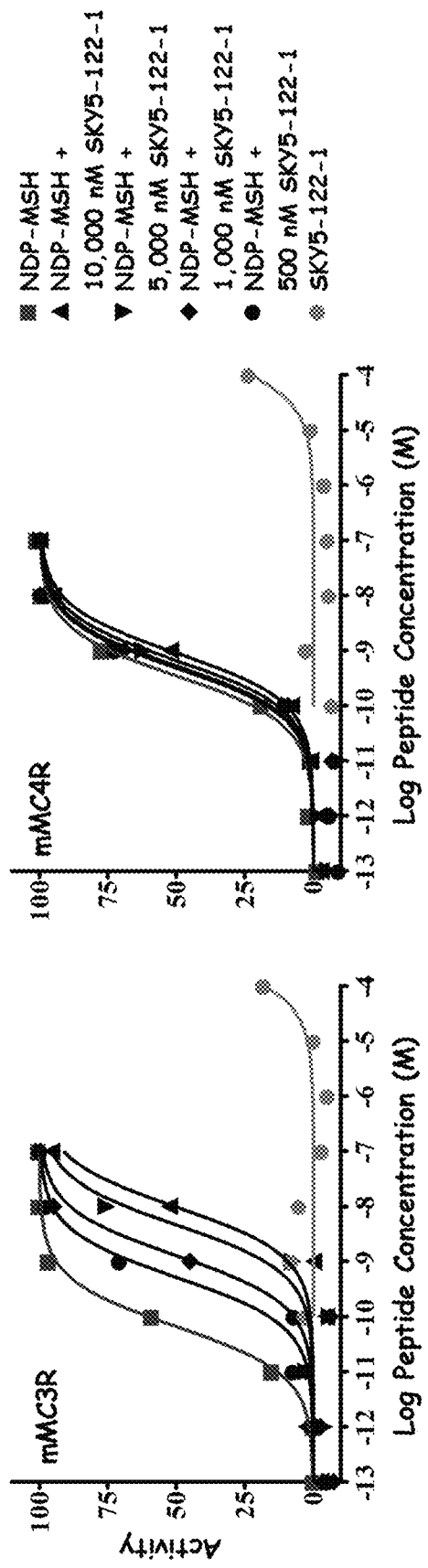
FIG. 9. Illustration of Antagonist Plots for the Most Potent Retro-Inverso Compound SKY5-122-1.

The retro-inversion of the TACO scaffold yielded a series of potent antagonists that were selective for the mMC3R over the mMC4R. The potencies for the four retro-inverso compounds ranged from a pA$_2$ of 7.2 to 6.4 (K$_i$=63 and 398 nm, respectively) at the mMC3R, and the antagonist activity observed at the mMC4R was at or below the limit of quantitation for the assay (pA$_2$<5.5 or K$_i$>3,100 nM). FIG. 9 illustrates the antagonist pharmacology for SKY5-122-1, the most potent mMC3R antagonist, at both the mMC3R and mMC4R. At the mMC3R, log shifts in potency can be observed for NDP-MSH with increasing concentrations of SKY5-122-1, whereas no shifts were observed at the mMC4R. FIG. 9 also illustrates the pharmacology for the peptide when it is assayed alone and the limited agonist activity at concentrations up to 100 µM for both receptor subtypes. Similar but less potent results were observed for SKY5-122-2, which had the DPhe[1] substitution in addition to the corresponding formylated N terminal analogs SKY5-142-A and SKY5-148. In addition to the antagonist activity at the mMC3R and no activity at the mMC4R, there was no activity observed at the mMC5R (EC$_{50}$>100 µM) and some inverse activity at the mMC1R. Further experiments would be required to fully characterize the observed inverse agonism at the mMC1R and to assess if the observed result has any relevance in vivo.

Figure 10:
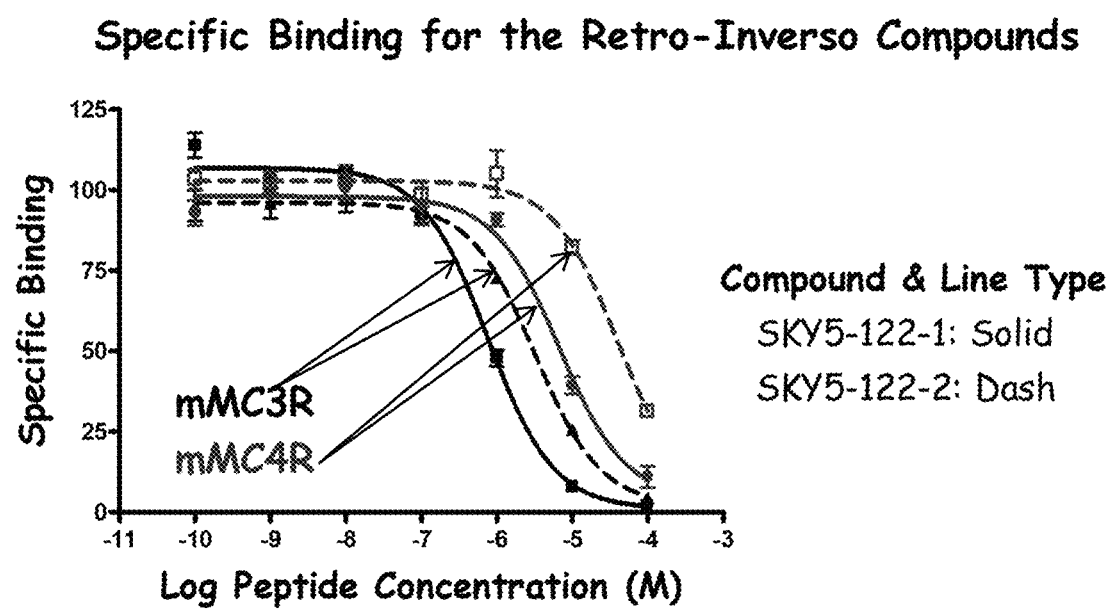
FIG. 10. Observed Dose-Response Curves for the Competitive Displacement of $^{125}$I-NDP-MSH for the Reported Retro-Inverso Compounds.'

The specific binding for SKY5-122-1 and SKY5-122-2 reflected a similar trend selectivity trend for the mMC3R over the mMC4R (Table 6 and FIG. 10). Both compounds were approximately 10-fold more potent at the mMC3R over the mMC4R (800 and 3,500 nM vs 6,700 and 39,500 nM, respectively). Compared to SKY4-48-1, Ac-His-DPhe-Arg-Trp-NH$_2$ (SEQ ID NO:2), SKY5-122-1 and SKY5-122-2 were better binders at the mMC3R (14- to 64-fold increase in IC$_{50}$) and possessed decreased binding affinity at the mMC4R (55- to 326-fold decrease in IC$_{50}$). Most, if not all, reports on MC3R selective compounds have been primarily limited to analogs of α-MSH and γ-MSH (Grieco, et al., *J. Med. Chem.* 2000, 43 (26), 4998-5002; Grieco, et al, *J. Med. Chem.* 2002, 45 (24), 5287-5294; Carotenuto, et al., *J. Med. Chem.* 2015, 58 (24), 9773-9778; Kavarana, et al., *J. Med. Chem.* 2002, 45 (12), 2644-2650; Grieco, et al., *Peptides* 2007, 28 (6), 1191-1196; Ballet, et al., *Bioorg. Med. Chem. Lett.* 2007, 17 (9), 2492-2498). However, there is one common feature between the tetrapeptides reported herein and the longer analogs.

The replacement of the sixth position on α-MSH analogs with bulky yet sterically constrained substitutions yields ligands that are selective MC3R antagonists (Ballet, et al., *Bioorg. Med. Chem. Lett.* 2007, 17 (9), 2492-2498). Consistent to the previous report, the substitution of a sterically constrained aromatic residue at the sixth position (using α-MSH numbering) appears to achieve selective antagonist activity at the MC3R over the MC4R (Ballet, et al., *Bioorg. Med. Chem. Lett.* 2007, 17 (9), 2492-2498). Herein is, to the best of our knowledge, the first report of a selective MC3R antagonist consisting of a tetrapeptide sequence.

Conclusions

All of these results, when taken together, suggest the reversal of the Arg and Phe residues did not result in the observed increase in selectivity of the previously reported TACO scaffold for the MC3R over the MC4R. Reversing the sequence in known melanocortin ligands was disastrous for activity at all of the tested receptor subtypes, indicating the "reversed" Arg-Phe di-peptide sequence was not a general strategy for increasing mMC3R selectivity over all melanocortin ligand scaffold systems The retro-inverso TACO peptides resulted in selective antagonist activity at the mMC3R over the mMC4R. The sequence of these peptides was similar to the endogenous melanocortin signaling sequence, when the sequences were aligned from their N to C termini yet most of the chiral centers were scrambled. The retro-inverso TACO peptide stereocenters were D-L-D-D whereas the stereocenters for the core signaling motif in α-MSH were L-L-L-L and L-D-L-L for NDP-MSH. Taking these two aspects of the TACO motif together, it may be concluded that the "reversed" TACO scaffold is indeed a novel pharmacophore distinctly different from the endogenous "His-Phe-Arg-Trp" motif.

In summary, the importance of the backbone direction and chemical topology of the previously reported TACO scaffold (Example 1), which was an agonist at the MC3R and an antagonist at the MC4R, was explored. It was postulated that the reversed "Arg-Phe" sequence, relative to the conserved "His-Phe-Arg-Trp" motif, was a new melanocortin pharmacophore, and by studying the requirements for each receptor subtype, selectivity for one of the receptor subtypes could be achieved while maintaining potency. A series of MSH analogs were constructed, which focused on the importance of side chain position, in addition to a series of retro-inverso tetrapepetide analogs. It was discovered that the mMC3 and mMC4 receptor subtypes have different molecular requirements which allowed for the identification of a selective mMC3R antagonist compound.

Experimental Section

The peptide library described above was synthesized and purified using identical chemistry and reagents as reported in Example 1. The solid phase synthesis method was modified while synthesizing the "reversed" MSH analogs. The common C terminal fragments for α-MSH and NDP-MSH, in addition to their corresponding "reversed" analogs, were synthesized together. Upon coupling the Trp[9] residue, the resin was then split into four equal aliquots and then the remaining residues for each of the analogs were coupled. After completing the synthesis of the four peptides, they were cleaved and purified in parallel as previously described. The AlphaScreen cAMP bioassay, $^{125}$I-NDP- MSH preparation and purification, and $^{125}$I-NDP-MSH competitive binding assay all used identical protocols described in Example 1.

EXAMPLE 3

In Vivo Murine Studies

The ability of the compounds of the invention to affect metabolic activity and/or food intake may be tested using in vivo feeding studies in mice. Specially developed mice (e.g., wild-type, melanocortin-3 receptor knockout, melanocortin-4 receptor knockout, and melanocortin-¾ receptor double knockout) may be injected with a compound of the invention and any possible effects on food intake and metabolic activity may be assessed.

EXAMPLE 4

In Vivo Feeding Study

A feeding study was conducted in a mouse model using SKY5-122-1, which has a sequence Ac-DTic-L(pI)Phe-DArg-DHis-NH$_2$ (SEQ ID NO:61) (also referred to as MDE7-29).

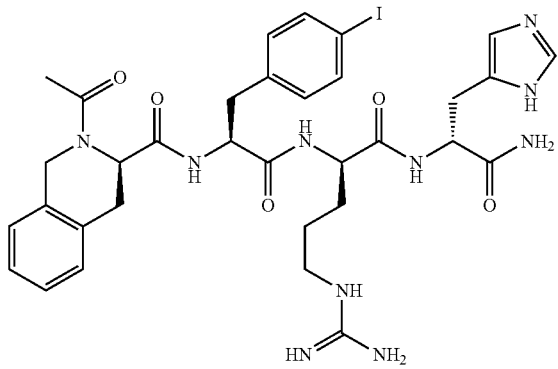

SKY5-122-1 (MDE7-29)

As an internal control the compound was resynthesized and the in vitro pharmacology was confirmed. The compound was administered in a dose-response manner with three different doses (10 nmol, 7.5 nmol, and 5 nmol) via intracerebroventricular (ICV) injection in wild-type mice housed in conventional cages. The mice (8 males and 9 females) were fasted for 22 hours prior to compound injection, and the parameters measured were the cumulative food intake and body weight. The results are compared to saline controls and the study used a Latin squares design.

Figure 11A:
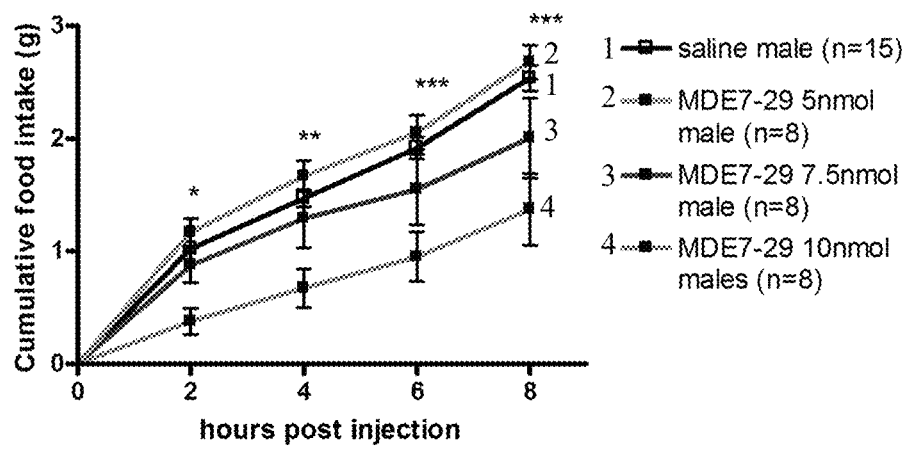
FIGS. 11A-B. Cumulative Food Intake Post-Injection for up to 8 Hours. (A) Dose response for cumulative food intake 8 hours post-injection in MC4R WT male mice receiving 5, 7.5 or 10 nmol of MDE7-29 in 3 μl of saline vs. 3 μl of saline via cannula after 22 hour fast. Data shown as mean±SEM. (Two way ANOVA showed treatment was significant, *P<0.05, P<0.01, *P<0.001). (B) Dose response for cumulative food intake 8 hours post-injection in MC4R WT female mice receiving 5, 7.5 or 10 nmol of MDE7-29 in 3 μl of saline vs. 3 μl of saline via cannula after 22 hour fast. Data shown as mean±SEM. (Two way ANOVA showed treatment was significant, P<0.0001. Bonferroni was used to compare individual time points *P<0.05, **P<0.01).
Figure 12A:
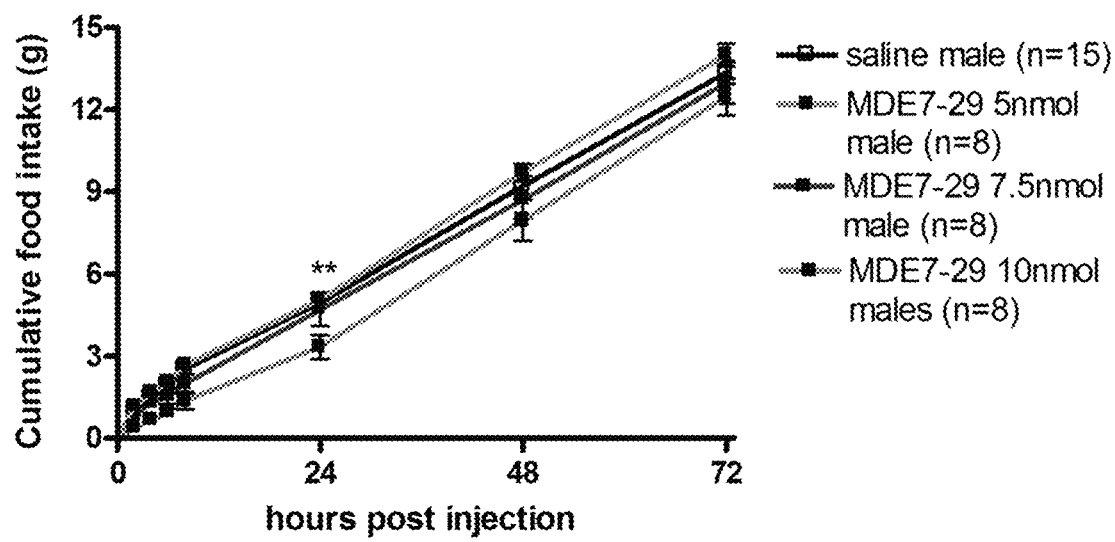
FIGS. 12A-B. Cumulative Food Intake Post-Injection for up to 72 Hours. (A) Food consumed up to 72 hours post-injection in male MC4R WT mice receiving 5 nmol, 7.5 nmol or 10 nmol of MDE7-29 in 3 μl of saline vs. 3 μl of saline via cannula. Mice were fasted 22 hours prior to injections. (Two way ANOVA showed treatment was significant, P<0.0001. Bonferroni was used to compare individual time points P<0.01). At 72 hours, MDE7-29 5 nmol had the highest food intake, followed by saline, MDE7-29 7.5 nmol and MDE7-29 10 nmol. (B) Food consumed up to 72 hours post-injection in female MC4R WT mice receiving 5 nmol, 7.5 nmol or 10 nmol of MDE7-29 in 3 μl of saline vs. 3 μl of saline via cannula. Mice were fasted 22 hours prior to injections. (Two way ANOVA showed treatment was significant, P<0.0001. Bonferroni was used to compare individual time points P<0.01). At 72 hours, MDE7-29 7.5 nmol had the highest food intake, followed by saline, MDE7-29 10 nmol and MDE7-29 5 nmol.
Figure 13A:
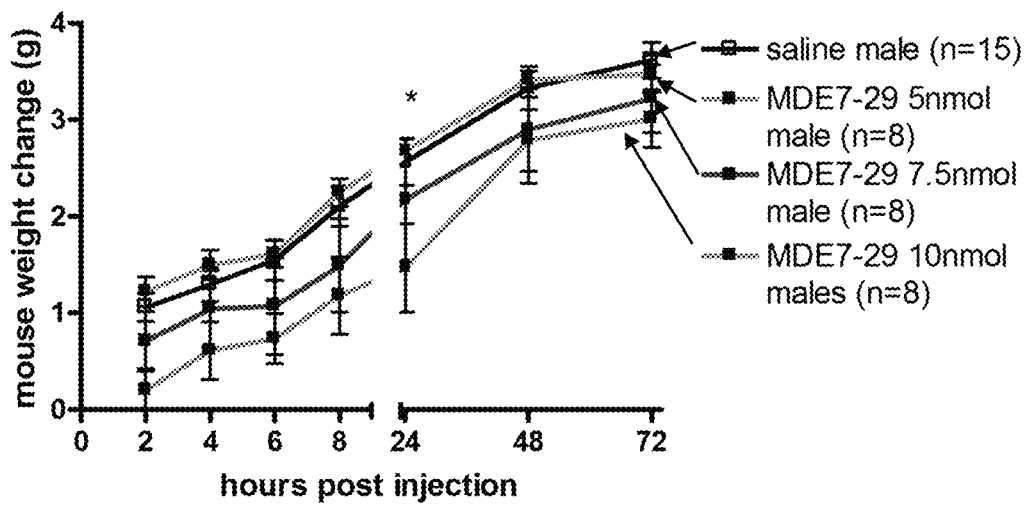
FIGS. 13A-B. Changes in Body Weight Post-Injection for up to 72 Hours. (A) Mouse weights up to 72 hours post-injection in male MC4R WT mice receiving 5 nmol, 7.5 nmol and 10 nmol MDE7-29 in 3 μl vs. 3 μl saline via cannula. Mice were fasted 22 hours prior to injections. (Two way ANOVA showed treatment was significant, P<0.0001. Bonferroni was used to compare individual time points *P<0.05). (B) Mouse weights up to 72 hours post-injection in female MC4R WT mice receiving 5 nmol, 7.5 nmol and 10 nmol MDE7-29 in 3 μl vs. 3 μl saline via cannula. Mice were fasted 22 hours prior to injections. (Two way ANOVA showed treatment was significant, P<0.0001. Bonferroni was used to compare individual time points *P<0.05, **P<0.01).

The male mice did not respond to a 5 nmol dose; however, they tended to decrease food intake with the 7.5 nmol dose (FIG. 11A). With the 10 nmol dose there was a significant decrease observed in food intake at 2, 4, 6, and 8 hours post injection (FIG. 11A). This significant decrease in food intake was observed for up to 24 hours post injection (FIG. 12A). There was also a corresponding significant decrease in the body weight for male mice with the 10 nmol dose at 24 hours post injection (FIG. 13A).

Figure 11B:
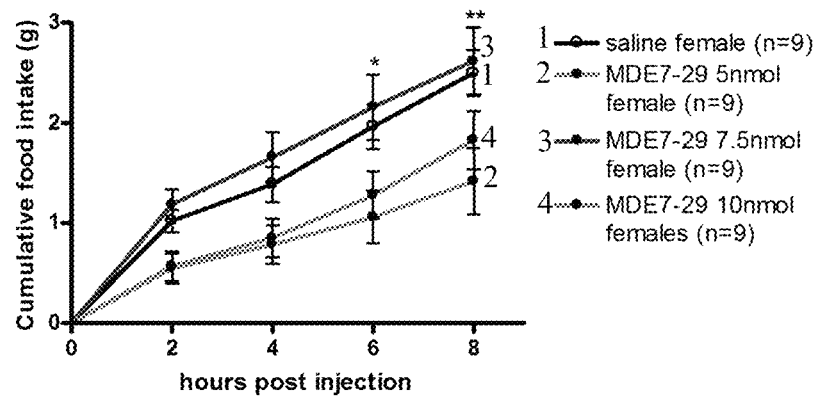
Figure 12B:
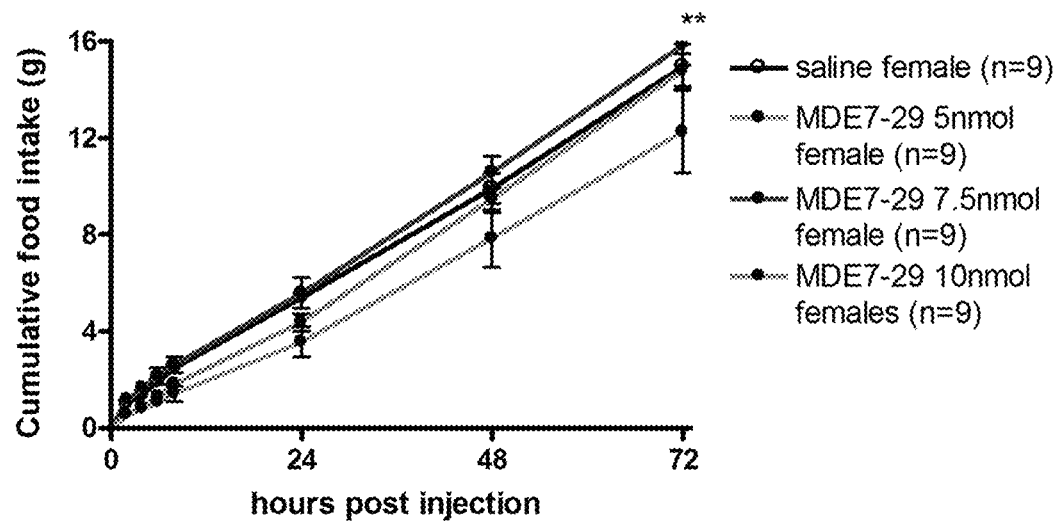
Figure 13B:
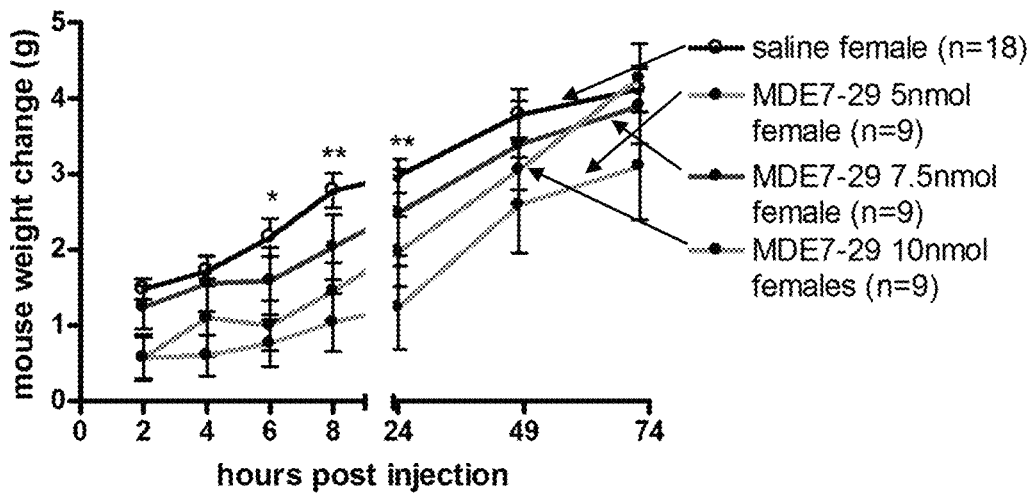

The female mice responded differently to the compound with respect to the male mice. There was a significant decrease in cumulative food intake with the 5 nmol dose 6 and 8 hours post injection, and for this dosage there was a significant difference at 72 hours post injected when compared to the saline controls (FIGS. 11B and 12B). There was also a significant decrease in mouse body weight at 6, 8, and 24 hours post injection for this dosage (FIG. 13B). There was no change in cumulative food intake or body weight at the 7.5 nmol dose; however, decreases were observed for the 10 nmol dose which were similar to the 5 nmol dose (FIGS. 11B, 12B and 13B). Sex-specific differences have previously been observed and reported (Lensing, ACS Chem. Neurosci., 2016, 1283-1291).

Tables

TABLE 1

Summary of agonist and antagonist data collected at the mMC3R and mMC4R

| | | mMC3R | | mMC4R | |
|---|---|---|---|---|---|
| ID | Sequence | Agonist EC$_{50}$ ± SEM (nM) | Antagonist pA$_2$ ± SEM | Agonist EC$_{50}$ ± SEM (nM) | Antagonist pA$_2$ ± SEM |
| NDP-MSH | Ac-Ser-Tyr-Ser-Nle-Glu-His-DPhe-Arg-Trp-Gly-Lys-Pro-Val-NH$_2$ (SEQ ID NO: 1) | 0.09 ± 0.01 | Full Agonist | 0.8 ± 0.1 | Full Agonist |
| SKY4-48-1 | Ac-His-DPhe-Arg-Trp-NH$_2$ (SEQ ID NO: 2) | 73 ± 10 | Full Agonist | 16 ± 3 | Full Agonist |
| SKY6-24-2 | Ac-His-Arg-(pI)DPhe-Tic-NH$_2$ (SEQ ID NO: 3) | 40 ± 7 | Full Agonist | >100,000 | 7.0 ± 0.2 |
| SKY4-48-2 | Ac-Arg-Arg-(pI)DPhe-Bip-NH$_2$ (SEQ ID NO: 4) | 45% @ 100 µM | 5.3 ± 0.1 | 32% @ 100 µM | 5.8 ± 0.1 |
| SKY4-48-3 | Ac-His-Arg-(pI)DPhe-Bip-NH$_2$ (SEQ ID NO: 5) | 53% @ 100 µM | No Activity | 43% @ 100 µM | No Activity |
| SKY4-48-4 | Ac-Bip-Arg-(pI)DPhe-Bip-NH$_2$ (SEQ ID NO: 6) | >100,000 | No Activity | 24% @ 100 µM | No Activity |
| SKY4-48-5 | Ac-3Bal-Arg-(pI)DPhe-Bip-NH$_2$ (SEQ ID NO: 7) | 51% @ 100 µM | No Activity | 35% @ 100 µM | No Activity |
| SKY4-146-1 | Ac-Tic-Arg-(pI)DPhe-Bip-NH$_2$ (SEQ ID NO: 8) | 100,000 | No Activity | >100,000 | No Activity |
| SKY4-48-7 | Ac-Phe-Arg-(pI)DPhe-Bip-NH$_2$ (SEQ ID NO: 9) | 30% @ 100 µM | No Activity | >100,000 | No Activity |
| SKY4-48-8 | Ac-Nal(2')-Arg-(pI)DPhe-Bip-NH$_2$ (SEQ ID NO: 10) | 14,000 ± 1,100 | Full Agonist | 7,900 ± 1,300 | Full Agonist |
| SKY5-146-2 | Ac-DNal(2')-Arg-(pI)DPhe-Bip-NH$_2$ (SEQ ID NO: 11) | 30% @ 100 µM | 5.6 ± 0.2 | 42% @ 100 µM | 6.6 ± 0.1 |
| SKY4-48-10 | Ac-Arg-Arg-(pI)DPhe-3Bal-NH$_2$ (SEQ ID NO: 12) | 160 ± 40 | Full Agonist | 24% @ 100 µM | 6.6 ± 0.1 |
| SKY4-48-11 | Ac-His-Arg-(pI)DPhe-3Bal-NH$_2$ (SEQ ID NO: 13) | 460 ± 50 | Full Agonist | 47% @ 100 µM | 6.4 ± 0.1 |
| SKY4-48-12 | Ac-Bip-Arg-(pI)DPhe-3Bal-NH$_2$ (SEQ ID NO: 14) | 2,300 ± 920 | Full Agonist | >100,000 | No Activity |
| SKY4-48-13 | Ac-3Bal-Arg-(pI)DPhe-3Bal-NH$_2$ (SEQ ID NO: 15) | 2,500 ± 770 | Full Agonist | >100,000 | 5.7 ± 0.3 |
| SKY4-48-14 | Ac-Tic-Arg-(pI)DPhe-3Bal-NH$_2$ (SEQ ID NO: 16) | 8,900 ± 2,400 | Full Agonist | >100,000 | 5.2 ± 0.1 |
| SKY4-48-15 | Ac-Phe-Arg-(pI)DPhe-3Bal-NH$_2$ (SEQ ID NO: 17) | 930 ± 520 | Full Agonist | >100,000 | 5.7 ± 0.1 |
| SKY4-48-16 | Ac-Nal(2')-Arg-(pI)DPhe-3Bal-NH$_2$ (SEQ ID NO: 18) | 1,500 ± 530 | Full Agonist | >100,000 | 6.0 ± 0.7 |
| SKY4-48-17 | Ac-DNal(2')-Arg-(pI)DPhe-3Bal-NH$_2$ (SEQ ID NO: 19) | 4,000 ± 1,300 | Full Agonist | 45% @ 100 µM | 6.6 ± 0.1 |
| SKY4-48-18 | Ac-Arg-Arg-(pI)DPhe-Tic-NH$_2$ (SEQ ID NO: 20) | 16 ± 3 | Full Agonist | >100,000 | 7.8 ± 0.3 |
| SKY4-48-20 | Ac-Bip-Arg-(pI)DPhe-Tic-NH$_2$ (SEQ ID NO: 21) | 13,000 ± 3,300 | Full Agonist | >100,000 | 5.7 ± 0.1 |

TABLE 1-continued

Summary of agonist and antagonist data collected at the mMC3R and mMC4R

| | | mMC3R | | | mMC4R | |
|---|---|---|---|---|---|---|
| ID | Sequence | Agonist EC$_{50}$ ± SEM (nM) | Antagonist pA$_2$ ± SEM | Agonist EC$_{50}$ ± SEM (nM) | Antagonist pA$_2$ ± SEM | |
| SKY4-48-21 | Ac-3Bal-Arg-(pI)DPhe-Tic-NH$_2$ (SEQ ID NO: 22) | 2,500 ± 190 | Full Agonist | 37% @ 100 µM | 6.2 ± 0.1 | |
| SKY6-24-1 | Ac-Tic-Arg-(pI)DPhe-Tic-NH$_2$ (SEQ ID NO: 23) | 3,900 ± 940 | Full Agonist | 36% @ 100 µM | 6.0 ± 0.2 | |
| SKY4-48-23 | Ac-Phe-Arg-(pI)DPhe-Tic-NH$_2$ (SEQ ID NO: 24) | 610 ± 200 | Full Agonist | >100,000 | 6.3 ± 0.1 | |
| SKY4-48-24 | Ac-Nal(2')-Arg-(pI)DPhe-Tic-NH$_2$ (SEQ ID NO: 25) | 3,000 ± 940 | Full Agonist | 33% @ 100 µM | 6.4 ± 0.1 | |
| SKY6-24-3 | Ac-DNal(2')-Arg-(pI)DPhe-Tic-NH$_2$ (SEQ ID NO: 26) | 600 ± 210 | Full Agonist | 32% @ 100 µM | 6.4 ± 0.1 | |
| SKY4-48-26 | Ac-Arg-Arg-(pI)DPhe-Phe-NH$_2$ (SEQ ID NO: 27) | 540 ± 190 | Full Agonist | >100,000 | 5.7 ± 0.1 | |
| SKY5-146-3 | Ac-His-Arg-(pI)DPhe-Phe-NH$_2$ (SEQ ID NO: 28) | 1,100 ± 240 | Full Agonist | >100,000 | 5.6 ± 0.1 | |
| SKY4-48-28 | Ac-Bip-Arg-(pI)DPhe-Phe-NH$_2$ (SEQ ID NO: 29) | 77% @ 100 µM | No Activity | >100,000 | 5.6 ± 0.1 | |
| SKY5-146-4 | Ac-3Bal-Arg-(pI)DPhe-Phe-NH$_2$ (SEQ ID NO: 30) | 37% @ 100 µM | No Activity | >100,000 | No Activity | |
| SKY4-48-30 | Ac-Tic-Arg-(pI)DPhe-Phe-NH$_2$ (SEQ ID NO: 31) | >100,000 | No Activity | >100,000 | No Activity | |
| SKY4-48-31 | Ac-Phe-Arg-(pI)DPhe-Phe-NH$_2$ (SEQ ID NO: 32) | 50% @ 100 µM | No Activity | >100,000 | No Activity | |
| SKY4-48-32 | Ac-Nal(2')-Arg-(pI)DPhe-Phe-NH$_2$ (SEQ ID NO: 33) | 42% @ 100 µM | No Activity | >100,000 | No Activity | |
| SKY4-48-33 | Ac-DNal(2')-Arg-(pI)DPhe-Phe-NH$_2$ (SEQ ID NO: 34) | >100,000 | 5.7 ± 0.1 | >100,000 | 6.9 ± 0.1 | |
| SKY4-48-34 | Ac-Arg-Arg-(pI)DPhe-Nal(2')-NH$_2$ (SEQ ID NO: 35) | 51% @ 100 µM | 5.8 ± 0.1 | >100,000 | 6.1 ± 0.1 | |
| SKY4-48-35 | Ac-His-Arg-(pI)DPhe-Nal(2')-NH$_2$ (SEQ ID NO: 36) | 57% @ 100 µM | 5.6 ± 0.1 | 35% @ 100 µM | 6.1 ± 0.2 | |
| SKY4-48-36 | Ac-Bip-Arg-(pI)DPhe-Nal(2')-NH$_2$ (SEQ ID NO: 37) | >100,000 | No Activity | >100,000 | No Activity | |
| SKY4-48-37 | Ac-3Bal-Arg-(pI)DPhe-Nal(2')-NH$_2$ (SEQ ID NO: 38) | 50% @ 100 µM | No Activity | >100,000 | No Activity | |
| SKY4-48-38 | Ac-Tic-Arg-(pI)DPhe-Nal(2')-NH$_2$ (SEQ ID NO: 39) | >100,000 | No Activity | >100,000 | 5.9 ± 0.1 | |
| SKY4-48-39 | Ac-Phe-Arg-(pI)DPhe-Nal(2')-NH$_2$ (SEQ ID NO: 40) | 44% @ 100 µM | No Activity | >100,000 | 5.9 ± 0.1 | |
| SKY4-48-40 | Ac-Nal(2')-Arg-(pI)DPhe-Nal(2')-NH$_2$ (SEQ ID NO: 41) | 39% @ 100 µM | No Activity | >100,000 | No Activity | |
| SKY5-146-5 | Ac-DNal(2')-Arg-(pI)DPhe-Nal(2')-NH$_2$ (SEQ ID NO: 42) | 43% @ 100 µM | 5.4 ± 0.1 | 39% @ 100 µM | 6.7 ± 0.1 | |
| SKY4-48-42 | Ac-Arg-Arg-(pI)DPhe-DNal(2')-NH$_2$ (SEQ ID NO: 43) | 57 ± 15 | Full Agonist | >100,000 | 6.4 ± 0.1 | |
| SKY4-48-43 | Ac-His-Arg-(pI)DPhe-DNal(2')-NH$_2$ (SEQ ID NO: 44) | 5,000 ± 2,100 | Full Agonist | 50% @ 100 µM | 5.5 ± 0.1 | |

TABLE 1-continued

Summary of agonist and antagonist data collected at the mMC3R and mMC4R

| | | mMC3R | | mMC4R | |
|---|---|---|---|---|---|
| ID | Sequence | Agonist EC$_{50}$ ± SEM (nM) | Antagonist pA$_2$ ± SEM | Agonist EC$_{50}$ ± SEM (nM) | Antagonist pA$_2$ ± SEM |
| SKY4-48-44 | Ac-Bip-Arg-(pI)DPhe-DNal(2')-NH$_2$ (SEQ ID NO: 45) | 32% @ 100 µM | No Activity | >100,000 | No Activity |
| SKY4-48-45 | Ac-3Bal-Arg-(pI)DPhe-DNal(2')-NH$_2$ (SEQ ID NO: 46) | 34% @ 100 µM | No Activity | 38% @ 100 µM | No Activity |
| SKY4-48-46 | Ac-Tic-Arg-(pI)DPhe-DNal(2')-NH$_2$ (SEQ ID NO: 47) | 42% @ 100 µM | No Activity | 33% @ 100 µM | No Activity |
| SKY4-48-47 | Ac-Phe-Arg-(pI)DPhe-DNal(2')-NH$_2$ (SEQ ID NO: 48) | 22% @ 100 µM | No Activity | >100,000 | 6.1 ± 0.4 |
| SKY4-48-48 | Ac-Nal(2')-Arg-(pI)DPhe-DNal(2')-NH$_2$ (SEQ ID NO: 49) | 31% @ 100 µM | No Activity | >100,000 | No Activity |
| SKY4-48-49 | Ac-DNal(2')-Arg-(pI)DPhe-DNal(2')-NH$_2$ (SEQ ID NO: 50) | 40% @ 100 µM | 5.6 ± 0.1 | 37% @ 100 µM | 5.9 ± 0.1 |

Table 1 is a summary of all the function data at the selected mMC3R and mMC4R using the AlphaScreen. NDP-MSH and Ac-His-DPhe-Arg-Trp-NH$_2$ (Ac-HFRW-NH$_2$) (SEQ ID NO: 2), in addition to assay media served as positive and negative controls, respectively. Forskolin served as an additional positive control due to the fact it activates adenylate cyclase independently of the melanocortin receptors. All of the compounds were assessed for agonist activity up to a concentration of 100 µM and values are represented as EC$_{50}$ in nM. Compounds which did not produce a full dose-response curve were tabulated as a percent of the NDP-MSH maximal positive control, and compounds with >20% activity were denoted as EC50 >100,000. These experiments were performed with duplicate replicates in three independent experiments. Compounds were assessed for antagonist activity if they did not produce a full dose-response. Antagonist activity was assessed by co-administering NDP-MSH and the compound at concentrations of 10,000 nM, 5,000 nM, 1,000 nM, and 500 nM and measuring the resulting shift in EC$_{50}$ and calculating a subsequent pA$_2$ value [-Log(K$_b$)] via a Schild analysis (Schild, et al., Br. J Pharmacol. 1947, 2 (3), 189-206). The antagonist experiment was performed in triplicate unless there was no shift in EC$_{50}$ activity was observed in which case it was tabulated as "no activity." Within each peptide, the stereochemistry for each amino acid was only specifically recited for "D" form amino acids; if nostereochemistry is specified, the amino acid used was an "L" form amino acid.

Table 1 is a summary of all the function data at the selected mMC3R using the AlphaScreen. NDP-MSH and Ac-His-DPhe-Arg-Trp-NH$_2$

TABLE 2

Summary of Agonist Data Collected at the mMC1R and mMC5R

| ID | Sequence | mMC1R EC$_{50}$ ± SEM (nM) | mMC1R EC$_{50}$ ± SEM (nM) |
|---|---|---|---|
| NDP-MSH | Ac-Ser-Tyr-Ser-Nle-Glu-His-DPhe-Arg-Trp-Gly-Lys-Pro-Val-NH$_2$ (SEQ ID NO: 1) | 0.02 ± 0.001 | 0.18 ± 0.02 |
| SKY4-48-1 | Ac-His-DPhe-Arg-Trp-NH$_2$ (SEQ ID NO: 2) | 20 ± 1 | 3.0 ± 0.5 |
| SKY6-24-2 | Ac-His-Arg-(pI)DPhe-Tic-NH$_2$ (SEQ ID NO: 3) | 0.71 ± 0.04 | 17 ± 3 |
| SKY4-48-2 | Ac-Arg-Arg-(pI)DPhe-Bip-NH$_2$ (SEQ ID NO: 4) | 44% @ 100 µM | 5,000 ± 1,600 |
| SKY4-48-3 | Ac-His-Arg-(pI)DPhe-Bip-NH$_2$ (SEQ ID NO: 5) | >100,000 | 69,000 ± 31,000 |
| SKY4-48-4 | Ac-Bip-Arg-(pI)DPhe-Bip-NH$_2$ (SEQ ID NO: 6) | >100,000 | >100,000 |
| SKY4-48-5 | Ac-3Bal-Arg-(pI)DPhe-Bip-NH$_2$ (SEQ ID NO: 7) | >100,000 | 72,000 ± 28,000 |
| SKY5-146-1 | Ac-Tic-Arg-(pI)DPhe-Bip-NH$_2$ (SEQ ID NO: 8) | 39% @ 100 µM | 71,000 ± 29,000 |
| SKY4-48-7 | Ac-Phe-Arg-(pI)DPhe-Bip-NH$_2$ (SEQ ID NO: 9) | 67% @ 100 µM | 68,000 ± 32,000 |
| SKY4-48-8 | Ac-Nal(2')-Arg-(pI)DPhe-Bip-NH$_2$ (SEQ ID NO: 10) | 7,600 ± 1,200 | 8,300 ± 1,600 |
| SKY5-146-2 | Ac-DNal(2')-Arg-(pI)DPhe-Bip-NH$_2$ (SEQ ID NO: 11) | >100,000 | 67,000 ± 33,000 |
| SKY4-48-10 | Ac-Arg-Arg-(pI)DPhe-3Bal-NH$_2$ (SEQ ID NO: 12) | 56 ± 20 | 210 ± 52 |
| SKY4-48-11 | Ac-His-Arg-(pI)DPhe-3Bal-NH$_2$ (SEQ ID NO: 13) | 70 ± 7 | 270 ± 67 |
| SKY4-48-12 | Ac-Bip-Arg-(pI)DPhe-3Bal-NH$_2$ (SEQ ID NO: 14) | 3,100 ± 490 | 5,500 ± 2,900 |
| SKY4-48-13 | Ac-3Bal-Arg-(pI)DPhe-3Bal-NH$_2$ (SEQ ID NO: 15) | 1,800 ± 590 | 18,000 ± 7,800 |
| SKY4-48-14 | Ac-Tic-Arg-(pI)DPhe-3Bal-NH$_2$ (SEQ ID NO: 16) | 38% @ 100 µM | 26,000 ± 7,200 |
| SKY4-48-15 | Ac-Phe-Arg-(pI)DPhe-3Bal-NH$_2$ (SEQ ID NO: 17) | 330 ± 180 | 1,300 ± 480 |
| SKY4-48-16 | Ac-Nal(2')-Arg-(pI)DPhe-3Bal-NH$_2$ (SEQ ID NO: 18) | 460 ± 210 | 5,400 ± 2,900 |
| SKY4-48-17 | Ac-DNal(2')-Arg-(pI)DPhe-3Bal-NH$_2$ (SEQ ID NO: 19) | 210 ± 50 | >100,000 |
| SKY4-48-18 | Ac-Arg-Arg-(pI)DPhe-Tic-NH$_2$ (SEQ ID NO: 20) | 0.51 ± 0.08 | 8.8 ± 0.7 |
| SKY4-48-20 | Ac-Bip-Arg-(pI)DPhe-Tic-NH$_2$ (SEQ ID NO: 21) | 440 ± 70 | 16,000 ± 8,000 |
| SKY4-48-21 | Ac-3Bal-Arg-(pI)DPhe-Tic-NH$_2$ (SEQ ID NO: 22) | 72 ± 26 | 4,100 ± 1,300 |
| SKY6-24-1 | Ac-Tic-Arg-(pI)DPhe-Tic-NH$_2$ (SEQ ID NO: 23) | 93 ± 26 | 570 ± 110 |
| SKY4-48-23 | Ac-Phe-Arg-(pI)DPhe-Tic-NH$_2$ (SEQ ID NO: 24) | 8 ± 3 | 200 ± 70 |
| SKY4-48-24 | Ac-Nal(2')-Arg-(pI)DPhe-Tic-NH$_2$ (SEQ ID NO: 25) | 54 ± 18 | 4,400 ± 2,700 |
| SKY6-24-3 | Ac-DNal(2')-Arg-(pI)DPhe-Tic-NH$_2$ (SEQ ID NO: 26) | 7 ± 2 | 250 ± 70 |
| SKY4-48-26 | Ac-Arg-Arg-(pI)DPhe-Phe-NH$_2$ (SEQ ID NO: 27) | 55 ± 9 | 340 ± 90 |
| SKY5-146-3 | Ac-His-Arg-(pI)DPhe-Phe-NH$_2$ (SEQ ID NO: 28) | 92 ± 19 | 680 ± 140 |
| SKY4-48-28 | Ac-Bip-Arg-(pI)DPhe-Phe-NH$_2$ (SEQ ID NO: 29) | 2,600 ± 1,600 | 69% @ 100 µM |
| SKY5-146-4 | Ac-3Bal-Arg-(pI)DPhe-Phe-NH$_2$ (SEQ ID NO: 30) | 1,200 ± 450 | 35% @ 100 µM |
| SKY4-48-30 | Ac-Tic-Arg-(pI)DPhe-Phe-NH$_2$ (SEQ ID NO: 31) | 3,500 ± 1,200 | 21% @ 100 µM |
| SKY4-48-31 | Ac-Phe-Arg-(pI)DPhe-Phe-NH$_2$ (SEQ ID NO: 32) | 600 ± 110 | 52% @ 100 µM |
| SKY4-48-32 | Ac-Nal(2')-Arg-(pI)DPhe-Phe-NH$_2$ (SEQ ID NO: 33) | 760 ± 600 | 49% @ 100 µM |
| SKY4-48-33 | Ac-DNal(2')-Arg-(pI)DPhe-Phe-NH$_2$ (SEQ ID NO: 34) | 540 ± 210 | >100,000 |
| SKY4-48-34 | Ac-Arg-Arg-(pI)DPhe-Nal(2')-NH$_2$ (SEQ ID NO: 35) | 210 ± 100 | 1,000 ± 350 |

TABLE 2-continued

Summary of Agonist Data Collected at the mMC1R and mMC5R

| ID | Sequence | mMC1R EC$_{50}$ ± SEM (nM) | mMC1R EC$_{50}$ ± SEM (nM) |
|---|---|---|---|
| SKY4-48-35 | Ac-His-Arg-(pI)DPhe-Nal(2')-NH$_2$ (SEQ ID NO: 36) | 350 ± 90 | 2,900 ± 1,100 |
| SKY4-48-36 | Ac-Bip-Arg-(pI)DPhe-Nal(2')-NH$_2$ (SEQ ID NO: 37) | 23% @ 100 μM | 21% @ 100 μM |
| SKY4-48-37 | Ac-3Bal-Arg-(pI)DPhe-Nal(2')-NH$_2$ (SEQ ID NO: 38) | 12,000 ± 4,000 | 50% @ 100 μM |
| SKY4-48-38 | Ac-Tic-Arg-(pI)DPhe-Nal(2')-NH$_2$ (SEQ ID NO: 39) | 66% @ 100 μM | 48% @ 100 μM |
| SKY4-48-39 | Ac-Phe-Arg-(pI)DPhe-Nal(2')-NH$_2$ (SEQ ID NO: 40) | 1,000 ± 750 | 61% @ 100 μM |
| SKY4-48-40 | Ac-Nal(2')-Arg-(pI)DPhe-Nal(2')-NH$_2$ (SEQ ID NO: 41) | 3,800 ± 2,200 | 45% @ 100 μM |
| SKY5-146-5 | Ac-DNal(2')-Arg-(pI)DPhe-Nal(2')-NH$_2$ (SEQ ID NO: 42) | 1,200 ± 390 | 40% @ 100 μM |
| SKY4-48-42 | Ac-Arg-Arg-(pI)DPhe-DNal(2')-NH$_2$ (SEQ ID NO: 43) | 280 ± 140 | 500 ± 100 |
| SKY4-48-43 | Ac-His-Arg-(pI)DPhe-DNal(2')-NH$_2$ (SEQ ID NO: 44) | 3,700 ± 2,400 | 47% @ 100 μM |
| SKY4-48-44 | Ac-Bip-Arg-(pI)DPhe-DNal(2')-NH$_2$ (SEQ ID NO: 45) | 5,300 ± 1,100 | 55% @ 100 μM |
| SKY4-48-45 | Ac-3Bal-Arg-(pI)DPhe-DNal(2')-NH$_2$ (SEQ ID NO: 46) | 36% @ 100 μM | 41% @ 100 μM |
| SKY4-48-46 | Ac-Tic-Arg-(pI)DPhe-DNal(2')-NH$_2$ (SEQ ID NO: 47) | 770 ± 90 | 74% @ 100 μM |
| SKY4-48-47 | Ac-Phe-Arg-(pI)DPhe-DNal(2')-NH$_2$ (SEQ ID NO: 48) | 3,800 ± 1,500 | 39% @ 100 μM |
| SKY4-48-48 | Ac-Nal(2')-Arg-(pI)DPhe-DNal(2')-NH$_2$ (SEQ ID NO: 49) | 53% @ 100 μM | 40% @ 100 μM |
| SKY4-48-49 | Ac-DNal(2')-Arg-(pI)DPhe-DNal(2')-NH$_2$ (SEQ ID NO: 50) | 4,000 ± 850 | 43% @ 100 μM |

Table 2 is a summary of all the function data at the selected mouse melanocortin receptors using the ALPHA screen. NDP-MSH and Ac-His-DPhe-Arg-Trp-NH$_2$ (SEQ ID NO: 2), in addition to assay media served as both positive and negative controls, respectively. Forskolin served as an additional positive control due to the fact it independently activates adenylate cyclase. All of the compounds were assessed for agonist activity up to a concentration of 100 μM and values are represented as EC$_{50}$ in nM. Compounds which did not produce a full dose-response curve were tabulated as a percent of the NDP-MSH maximal positive control, and compounds with <20% activity were denoted as EC$_{50}$ >100,000. These experiments were performed in triplicate. Within each peptide, the stereochemistry for each amino acid was only specifically recited for "D" form amino acids; if no stereochemistry is specified, the amino acid used was an "L" form amino acid

TABLE 3

Summary of $^{125}$I-NDP-MSH Binding Displacement of Selected TACOs at the mMC3R and mMC4R

| | | mMC3R (IC$_{50}$) | | mMC4R (IC$_{50}$) | |
|---|---|---|---|---|---|
| Compound | Sequence | Mean SEM | Fold Diff. | Mean SEM | Fold Diff. |
| NDP-MSH | Ac-Ser-Tyr-Ser-Nle-Glu-His-DPhe-Arg-Trp-Gly-Lys-Pro-Val-NH$_2$ (SEQ ID NO: 1) | 5.3 ± 0.7 | | 2.0 ± 0.2 | |
| SKY4-48-1 | Ac-His-DPhe-Arg-Trp-NH$_2$ (SEQ ID NO: 2) | 50500 ± 500 | 1.0 | 121 ± 39 | 1.0 |
| SKY6-24-2 | Ac-His-Arg-(pI)DPhe-Tic-NH$_2$ (SEQ ID NO: 3) | 975 ± 225 | -52 | 83 ± 13 | 1 |
| SKY4-48-10 | Ac-Arg-Arg-(pI)DPhe-3Bal-NH$_2$ (SEQ ID NO: 12) | 965 ± 135 | -52 | 93 ± 6 | 1 |
| SKY4-48-11 | Ac-His-Arg-(pI)DPhe-3Bal-NH$_2$ (SEQ ID NO: 13) | 3400 ± 300 | -15 | 275 ± 35 | 2 |
| SKY4-48-15 | Ac-Phe-Arg-(pI)DPhe-3Bal-NH$_2$ (SEQ ID NO: 17) | 5350 ± 250 | -9 | 850 ± 40 | 7 |
| SKY4-48-18 | Ac-Arg-Arg-(pI)DPhe-Tic-NH$_2$ (SEQ ID NO: 20) | 550 ± 120 | -92 | 13 ± 3 | -9 |

TABLE 3-continued

Summary of $^{125}$I-NDP-MSH Binding Displacement of Selected TACOs at the mMC3R and mMC4R

| Compound | Sequence | mMC3R (IC$_{50}$) Mean SEM | Fold Diff. | mMC4R (IC$_{50}$) Mean SEM | Fold Diff. |
|---|---|---|---|---|---|
| SKY4-48-23 | Ac-Phe-Arg-(pI)DPhe-Tic-NH$_2$ (SEQ ID NO: 24) | 2500 ± 600 | −20 | 135 ± 15 | 1 |
| SKY6-24-3 | Ac-DNal(2')-Arg-(pI)DPhe-Tic-NH$_2$ (SEQ ID NO: 26) | 420 ± 50 | −120 | 43 ± 7 | −3 |
| SKY4-48-26 | Ac-Arg-Arg-(pI)DPhe-Phe-NH$_2$ (SEQ ID NO: 27) | 6500 ± 600 | −8 | 455 ± 85 | 4 |
| SKY4-48-42 | Ac-Arg-Arg-(pI)DPhe-DNal(2')-NH$_2$ (SEQ ID NO: 43) | 440 ± 70 | −115 | 220 ± 10 | 2 |

Table 3 includes the 9 most potent TACOs at the mMC3R were selected for $^{125}$I NDP-MSH radiolabel competition binding experiments. The compounds were assayed at both the mMC3R and mMC4R, and the reported values are the mean and standard error of the mean of two independent experiments each consisting of duplicate replicates. In addition, NDP-MSH and SKY4-48-1, Ac-His-DPhe-Arg-Trp-NH$_2$ (SEQ ID NO: 2), are included for assay control and reference purposes. The fold difference (Fold Diff) is determined between the peptide as compared to the tetrapeptide Ac-His-DPhe-Arg-Trp-NH$_2$ (Ac-HfRW-NH$_2$) (SEQ ID NO: 2) control. A negative fold difference indicates the binding affinity of the peptide is more potent than the Ac-His DPhe-Arg-Trp-NH 2 (Ac-HfRW-NH$_2$) (SEQ ID NO: 2) control. Within each peptide, the stereochemistry for each amino acid was only specifically recited for "D" form amino acids; if no stereochemistry is specified, the amino acid used was an "L" form amino acid.

TABLE 4

Summary of the analytical information for the single tetrapeptides synthesized and characterized in this study. Purity for these compounds is >95%

| ID | k' Solvent 1 (Acetonitrile) | k' Solvent 2 (Methanol) | Purity (%) | Observed Mass [M + 1] | Calculated Exact Mass |
|---|---|---|---|---|---|
| NDP-MSH | 4.2 | 7.8 | 98.6 | *824.0 [M + 2] | 1645.84 |
| SKY4-48-1 | 4.4 | 6.6 | >99 | 686.3 | 685.34 |
| SKY6-24-2 | 6.0 | 10.7 | >99 | 785.3 | 784.23 |
| SKY4-48-2 | 8.3 | 12.7 | 99.1 | 868.3 | 867.30 |
| SKY4-48-3 | 8.3 | 12.8 | >99 | 849.3 | 848.26 |
| SKY4-48-4 | 11.4 | 16.0 | >99 | 935.3 | 934.30 |
| SKY4-48-5 | 10.6 | 15.4 | 97.1 | 915.3 | 914.24 |
| SKY5-146-1 | 9.8 | 15.3 | 99.8 | 871.3 | 870.27 |
| SKY4-48-7 | 9.9 | 14.8 | 95.2 | 859.3 | 858.27 |
| SKY4-48-8 | 10.8 | 15.6 | 97.5 | 909.3 | 908.28 |
| SKY5-146-2 | 10.2 | 15.5 | 99.9 | 909.3 | 908.28 |
| SKY4-48-10 | 7.5 | 11.8 | 97.3 | 846.3 | 847.24 |
| SKY4-48-11 | 7.5 | 12.0 | >99 | 829.3 | 828.20 |
| SKY4-48-12 | 10.9 | 15.6 | >99 | 915.2 | 914.24 |
| SKY4-48-13 | 12.5 | 15.0 | >99 | 895.2 | 894.18 |
| SKY4-48-14 | 14.7 | 14.1 | 98.4 | 851.3 | 850.21 |
| SKY4-48-15 | 9.7 | 14.3 | >99 | 839.2 | 838.21 |
| SKY4-48-16 | 10.7 | 15.1 | 97.8 | 889.2 | 888.22 |
| SKY4-48-17 | 10.1 | 14.6 | >99 | 889.3 | 888.22 |
| SKY4-48-18 | 7.0 | 10.7 | >99 | 804.2 | 803.27 |
| SKY4-48-20 | 10.6 | 15.0 | >99 | 871.3 | 870.27 |
| SKY4-48-21 | 9.7 | 14.2 | 99.3 | 851.2 | 850.21 |
| SKY6-24-1 | 7.9 | 13.0 | 95.2 | 807.3 | 806.24 |
| SKY4-48-23 | 9.0 | 13.0 | >99 | 795.3 | 794.24 |
| SKY4-48-24 | 9.7 | 14.3 | >99 | 845.2 | 844.25 |
| SKY6-24-3 | 8.7 | 13.5 | >99 | 845.3 | 844.25 |
| SKY4-48-26 | 6.5 | 10.7 | >99 | 792.3 | 791.27 |
| SKY5-146-3 | 6.2 | 10.8 | >99 | 773.2 | 772.23 |
| SKY4-48-28 | 10.1 | 15.0 | 96.8 | 859.3 | 858.27 |
| SKY5-146-4 | 9.0 | 14.6 | >99 | 839.2 | 838.21 |
| SKY4-48-30 | 8.6 | 13.2 | 96.0 | 795.2 | 794.24 |
| SKY4-48-31 | 8.8 | 13.1 | >99 | 783.2 | 782.24 |
| SKY4-48-32 | 6.1 | 14.3 | 98.6 | 833.1 | 832.25 |
| SKY4-48-33 | 9.1 | 13.6 | >99 | 833.3 | 832.25 |
| SKY4-48-34 | 7.6 | 11.8 | >99 | 842.4 | 841.28 |
| SKY4-48-35 | 9.5 | 12.0 | >99 | 823.1 | 822.24 |
| SKY4-48-36 | 11.0 | 15.6 | >99 | 909.2 | 908.28 |
| SKY4-48-37 | 10.0 | 14.9 | 97.2 | 889.2 | 888.22 |
| SKY4-48-38 | 9.4 | 14.2 | 96.8 | 845.3 | 844.25 |
| SKY4-48-39 | 9.3 | 14.2 | 96.3 | 833.3 | 832.25 |
| SKY4-48-40 | 10.2 | 15.0 | >99 | 883.3 | 882.26 |

TABLE 4-continued

Summary of the analytical information for the single tetrapeptides synthesized and characterized in this study. Purity for these compounds is >95%

| ID | k' Solvent 1 (Acetonitrile) | k' Solvent 2 (Methanol) | Purity (%) | Observed Mass [M + 1] | Calculated Exact Mass |
|---|---|---|---|---|---|
| SKY5-146-5 | 9.7 | 15.0 | >99 | 883.3 | 882.26 |
| SKY4-48-42 | 7.3 | 11.6 | >99 | 842.3 | 841.28 |
| SKY4-48-43 | 7.3 | 11.5 | 97.4 | 823.2 | 822.24 |
| SKY4-48-44 | 9.8 | 15.2 | >99 | 909.1 | 908.28 |
| SKY4-48-45 | 10.0 | 14.5 | >99 | 889.2 | 888.22 |
| SKY4-48-46 | 9.1 | 13.5 | >99 | 845.3 | 844.25 |
| SKY4-48-47 | 9.0 | 13.6 | 98.0 | 833.2 | 832.25 |
| SKY4-48-48 | 10.0 | 14.6 | >99 | 883.3 | 882.26 |
| SKY4-48-49 | 10.0 | 14.4 | >99 | 883.3 | 882.26 |

The k' is defined as [(Retention Time − Solvent Time)/Retention Time]. The compounds were assessed for purity using two different HPLC solvent systems. Solvent system 1 was a 10% to 90% acetonitrile gradient in 0.1% TFA in water over 35 minutes at a rate of 1.5 mL/min using an analytical Vydac C18 column (Vydac 218TP104). Solvent system 2 was a 10% to 90% methanol gradient in 0.1% TFA in water over 35 minutes using the same flow rate and column as solvent system 1. The purity was assessed by integrating the area under the curve at $\lambda$ = 214 nm. The mass was confirmed using a matrix-assisted laser desorption/ionization-time of flight mass spectrometer (MALDI-TOF MS) using a cyano-4-hydroxycinnamic acid matrix (AB-Sciex 5800, University of Minnesota Department of Chemistry Mass Spectrometry Laboratory).
*Note, the mass of NDP-MSH was confirmed using electrospray ionization-time of flight (ESI-TOF) spectrometer (Bruker BioTOF II, University of Minnesota Department of Chemistry Mass Spectrometry Laboratory). Within each peptide, the stereochemistry for each amino acid was only specifically recited for "D" form amino acids; if no stereochemistry is specified, the amino acid used was an "L" form amino acid.

TABLE 5

Selected melanocortin ligands and their "reverse analogs"

| Cmpd ID | Type | Sequence | mMC1R EC$_{50}$ ± SEM | mMC3R EC$_{50}$ ± SEM | mMC4R EC$_{50}$ ± SEM | mMC5R EC$_{50}$ ± SEM |
|---|---|---|---|---|---|---|
| SKY2-125-4 | α-MSH | Ac-Ser-Tyr-Ser-Met-Glu-His-Phe-Arg-Trp-Gly-Lys-Pro-Val-NH$_2$ (SEQ ID NO: 51) | 0.14 ± 0.03 | 0.13 ± 0.07 | 1.9 ± 0.6 | 0.07 ± 0.03 |
| SKY2-125-5 | (Arg$^7$, Phe$^8$) α-MSH | Ac-Ser-Tyr-Ser-Met-Glu-His-Arg-Phe-Trp-Gly-Lys-Pro-Val-NH$_2$ (SEQ ID NO:52) | 3,000 ± 900 | 5,800 ± ,200 | 44,000 ± 30,000 | 2,600 ± 930 |
| NDP-MSH | NDP-MSH | Ac-Ser-Tyr-Ser-Nle-Glu-His-DPhe-Arg-Trp-Gly-Lys-Pro-Val-NH$_2$ (SEQ ID NO: 53) | 0.02 ± 0.01 | 0.05 ± 0.01 | 0.3 ± 0.1 | 0.05 ± 0.01 |
| SKY2-125-3 | (Arg7, Phe8) NDP-MSH | Ac-Ser-Tyr-Ser-Nle-Glu-His-Arg-DPhe-Trp-Gly-Lys-Pro-Val-NH$_2$ (SEQ ID NO: 54) | 380 ± 70 | 1,800 ± 200 | 9,500 ± 3,000 | 1,600 ± 230 |
| SKY4-48-1 | Reference | Ac-His-DPhe-Arg-Trp-NH$_2$ (SEQ ID NO:2) | 20 ± 1 | 73 ± 10 | 16 ± 3 | 3.0 ± 0.5 |
| SKY5-146-6 | Rev. Tetra. | Ac-His-Arg-DPhe-Trp-NH$_2$ (SEQ ID NO: 55) | 1,300 ± 500 | 21,000 ± 7,000 Full Agonist | >100,000 pA$_2$ = No Activity | 21,000 ± 5,000 |
| SKY5-121 | Retro. Tetra. | Ac-DTrp-DArg-Phe-DHis-NH$_2$ (SEQ ID NO: 56) | >100,000 | >100,000 pA$_2$ = No Activity | >100,000 pA$_2$ = No Activity | 29% @ 100 μM |
| CJL-1-20 | CJL Data | Ac-His-(pI)DPhe-Arg-Trp-NH$_2$ (SEQ ID NO:57) | 12 ± 2 | 56% @ 100 μM pA$_2$ = 6.8 ± 0.1 | 44% @ 100 μM pA$_2$ = 8.6 ± 0.1 | 2.7 ± 1.1 |
| SKY5-146-7 | Rev. Tetra. | Ac-His-Arg-(pI)DPhe-Trp-NH$_2$ (SEQ ID NO:58) | 270 ± 130 | 500 ± 170 Full Agonist | 29% @ 100 μM pA$_2$ = 6.0 ± 0.1 | 690 ± 120 |

TABLE 5-continued

Selected melanocortin ligands and their "reverse analogs"

| Cmpd ID | Type | Sequence | mMC1R $EC_{50}$ ± SEM | mMC3R $EC_{50}$ ± SEM | mMC4R $EC_{50}$ ± SEM | mMC5R $EC_{50}$ ± SEM |
|---|---|---|---|---|---|---|
| SKY6-24-2 | Reference | Ac-His-Arg-(pI)DPhe-Tic-NH$_2$ (SEQ ID NO:3) | 0.71 ± 0.05 | 40 ± 7 Full Agonist | >100,000 $pA_2$ = 7.0 ± 0.2 | 17 ± 3 |
| SKY5-122-2 | Retro. Tetra. | Ac-DPhe-(pI)Phe-DArg-DHis-NH$_2$ (SEQ ID NO:59) | *720 ± 130 | >100,000 $pA_2$ = 6.4 ± 0.1 | 16% @ 100 µM = No Activity | >100,000 |
| SKY5-142-A | Retro. Tetra. | For-DPhe-(pI)Phe-DArg-DHis-NH$_2$ (SEQ ID NO:60) | *420 ± 99 | >100,000 $pA_2$ = 6.7 ± 0.1 | 47% @ 100 µM = No Activity | >100,000 |
| SKY5-122-1 | Retro. Tetra. | Ac-DTic-(pI)Phe-DArg-DHis-NH$_2$ (SEQ ID NO:61) | *22 ± 9 | >100,000 $pA_2$ = 7.2 ± 0.1 | 42% @ 100 µM $pA_2$ = 5.5 ± 0.1 | >100,000 |
| SKY5-148 | Retro. Tetra. | For-DTic-(pI)Phe-DArg-DHis-NH$_2$ (SEQ ID NO:62) | *40 ± 7 | >100,000 $pA_2$ = 6.8 ± 0.1 | 71% @ 100 µM $pA_2$ = 5.4 ± 0.1 | >100,000 |

*Inverse agonist activity observed

Table 5 is a summary of all the function data at the selected mouse melanocortin receptors using the AlphaScreen. NDP-MSH and assay media served as both positive and negative controls, respectively. Forskolin served as an additional positive control due to the fact it independently activates adenylate cyclase from the melanocortin receptors. All of the compounds were assessed for agonist activity up to a concentration of 100 µM and values are represented as $EC_{50}$ in nM. Compounds which did not produce a full dose-response curve were tabulated as a percent of the NDP-MSH maximal positive control, and compounds with <20% activity were denoted as $EC_{50}$ >100,000 nM. These experiments were performed in triplicate.
Compounds were assessed for antagonist activity at the mMC3R and mMC4R if they did not produce a full dose-response. Antagonist activity was assessed by co-administering NDP-MSH and the compound at concentrations of 10,000, 5,000, 1,000, and 500 nM and measuring the resulting shift in $EC_{50}$ and calculating a subsequent $pA_2$ value [-Log($K_B$)] via a Schild analysis (Schild, Br. I Pharmacol. 1947, 2 (3), 189-206). The antagonist experiment was performed in triplicate unless there was no shift in $EC_{50}$ activity was observed in which case it was tabulated as "no activity." Within each peptide, the stereochemistry for each amino acid was only specifically recited for "D" form amino acids; if no stereochemistry is specified, the amino acid used was an "L" form amino acid.

TABLE 6

Summary of the Binding Data for NDP-MSH, SKY4-48-1, SKY5-122-1, and SKY5-122-2

| Compound | Sequence | mMC3R Mean ± SEM | Fold Diff. | mMC4R Mean ± SEM | Fold Diff. |
|---|---|---|---|---|---|
| NDP-MSH | Ac-Ser-Tyr-Ser-Nle-Glu-His-DPhe-Arg-Trp-Gly-Lys-Pro-Val-NH$_2$ (SEQ ID NO: 1) | 5.3 ± 0.7 | | 2.0 ± 0.2 | |
| SKY4-48-1 | Ac-His-DPhe-Arg-Trp-NH$_2$ (SEQ ID NO: 2) | 50,500 ± 500 | 1.0 | 121 ± 39 | 1.0 |
| SKY5-122-1 | Ac-DTic-(pI)LPhe-DArg-DHis-NH$_2$ (SEQ ID NO: 61) | 800 ± 170 | 64 | 6,700 ± 400 | -55 |
| SKY5-122-2 | Ac-DPhe-(pI)LPhe-DArg-DHis-NH$_2$ (SEQ ID NO: 59) | 3,500 ± 1,300 | 14 | 39,500 ± 10,500 | -326 |

Table 6 is a summary of the specific binding data for two of the retro-invsero TACO analogues (SKY5-122-1 and SKY5-122-2). The peptides SKY4-48-1 in addition to NSP-MSH were used as control compounds. The numbers reported are the mean and corresponding standard error of the mean for, at least, two independent experiments each containing duplicate replicates for each concentration tested. Within each peptide, the stereochemistry for each amino acid was only specifically recited for "D" form amino acids; if no stereochemistry is specified, the amino acid used was an "L" form amino acid.

TABLE 7

Summary of Analytical Data for Retro-TACO and "Reversed" Melanocortin Analogs

| Cpmd ID | Type | Sequence | k' System 1 Acetonitrile | k' System 2 Methanol | Calculated Exact Mass | Observed MALDI-MS [M + 1] |
|---|---|---|---|---|---|---|
| SKY2-125-4 | α-MSH | Ac-Ser-Tyr-Ser-Met-Glu-His-Phe-Arg-Trp-Gly-Lys-Pro-Val-NH₂ (SEQ ID NO: 51) | 4.9 | 8.9 | 1664.9 | 833.3 (2+) |
| SKY2-125-5 | (Arg⁷, Phe⁸) α-MSH | Ac-Ser-Tyr-Ser-Met-Glu-His-Arg-Phe-Trp-Gly-Lys-Pro-Val-NH₂ (SEQ ID NO: 52) | 4.7 | 8.6 | 1664.9 | 833.3 (2+) |
| SKY2-125-2 | NDP-MSH | Ac-Ser-Tyr-Ser-Nle-Glu-His-Phe-Arg-Trp-Gly-Lys-Pro-Val-NH₂ (SEQ ID NO: 53) | 5.0 | 9.3 | 1646.9 | 824.3 (2+) |
| SKY2-125-3 | (Arg⁷, Phe⁸) NDP-MSH | Ac-Ser-Tyr-Ser-Nle-Glu-His-Arg-DPhe-Trp-Gly-Lys-Pro-Val-NH₂ (SEQ ID NO: 54) | 5.1 | 9.3 | 1646.9 | 824.8 (2+) |
| SKY5-146-6 | Rev. Tetra. | Ac-His-Arg-DPhe-Trp-NH₂ (SEQ ID NO: 55) | 6.3 | 9.4 | 685.3 | 686.3 |
| SKY5-121 | Retro. Tetra. | Ac-DTrp-DArg-Phe-DHis-NH₂ (SEQ ID NO: 56) | 5.3 | 8.2 | 685.3 | 686.2 |
| CJL-1-20 | CJL Data | Ac-His-(pI)DPhe-Arg-Trp-NH₂ (SEQ ID NO: 57) | 3.4 | 6.1 | 811.7 | 812.4* |
| SKY5-146-7 | Rev. Tetra. | Ac-His-Arg-(pI)DPhe-Trp-NH₂ (SEQ ID NO: 58) | 7.4 | 11.2 | 811.2 | 812.2 |
| SKY5-122-2 | Retro. Tetra. | Ac-DPhe-(pI)Phe-DArg-DHis-NH₂ (SEQ ID NO: 59) | 7.3 | 11.7 | 772.2 | 773.0 |
| SKY5-142-A | Retro. Tetra. | For-DPhe-(pI)Phe-DArg-DHis-NH₂ (SEQ ID NO: 60) | 7.2 | 11.7 | 758.2 | 759.1 |
| SKY5-122-1 | Retro. Tetra. | Ac-DTic-(pI)Phe-DArg-DHis-NH₂ (SEQ ID NO: 61) | 7.5 | 11.9 | 784.23 | 784.7 |
| SKY5-148 | Retro. Tetra. | For-DTic-(pI)Phe-DArg-DHis-NH₂ (SEQ ID NO: 62) | 7.4 | 11.7 | 770.2 | 771.0 |

The k' is defined as [(Retention Time) - Solvent Time)/Retention Time]. The compounds were assessed for purity using two different HPLC solvent systems. Solvent system 1 was a 10% to 90% acetonitrile gradient in 0.1% TFA in water over 35 minutes at a rate of 1.5 mL/min using an analytical Vydac C18 column (Vydac 218TP104). Solvent system 2 was a 10% to 90% methanol gradient in 0.1% TFA in water over 35 minutes using the same flow rate and column as solvent system 1. The purity was assessed by integrating the area under the curve at λ = 214 nm and is greater than 95%. The mass was confirmed using a matrix-assisted laser desorption/ionization-time of flight mass spectrometer (MALDI-TOF MS) using a cyano-4-hydroxycinnamic acid matrix (AB-Sciex 5800, University of Minnesota Department of Chemistry Mass Spectrometry Laboratory).
*Note,
the mass of CJL-1-20 was confirmed using electrospray ionization-time of flight (ESI-TOF) spectrometer (Bruker BioTOF II, University of Minnesota Department of Chemistry Mass Spectrometry Laboratory). Within each peptide, the stereochemistry for each amino acid was only specifically recited for "D" form amino acids; if no stereochemistry is specified, the amino acid used was an "L" form amino acid.

TABLE 8

Summary of Activity Data for Certain Compounds of Formula (I) and Formula (II)

| Compound ID | Amino Acid Sequence (N- to C- terminus) | Melanocortin-3 Receptor | | Melanocortin-4 Receptor | |
|---|---|---|---|---|---|
| | | Agonist Activity EC$_{50}$ (nM) | Antagonist Activity K (nM) | Agonist Activity EC$_{50}$ (nM) | Antagonist Activity K (nM) |
| SKY6-24-2 | Ac-LHis-LArg-D(pI)Phe-LTic-NH$_2$ (SEQ ID NO: 3) | 40 | — | >100,000 | 100 |
| SKY4-48-18 | Ac-LArg-LArg-D(pI)Phe-LTic-NH$_2$ (SEQ ID NO: 20) | 16 | — | >100,000 | 16 |
| SKY4-48-42 | Ac-LArg-LArg-D(pI)Phe-DNal(2')-NH$_2$ (SEQ ID NO: 43) | 57 | — | >100,000 | 400 |
| SKY5-122-1 | Ac-DTic-L(pI)Phe-DArg-DHis-NH$_2$ (SEQ ID NO: 61) | >100,000 | 63 | 42% @ 100 μM | Not detected |
| SKY5-122-2 | Ac-DPhe-L(pI)Phe-DArg-DHis-NH$_2$ (SEQ ID NO: 59) | >100,000 | 400 | 16% @ 100 μM | Not detected |

The following abbreviations were used: Histidine (His); Arginine (Arg); para-Iodo-Phenylalanine ((pI)Phe); 1,2,3,4-Tetrahydroisoquinoline-3-Carboxylic Acid (Tic); 2-Napthylalanine (Nal(2')); Phenylalanine (Phe); Acetylated N Terminus (Ac); Amidated C Terminus (NH$_2$). The D/L in front of each amino acid indicates the stereochemistry of that particular amino acid using the standard convention for amino acids. Each compound was tested using the in vitro cell assays described in Examples 1 and 2 in a minimum of three independent experiments. SKY6-24-2 is a 40 nM agonist at the melanocortin-3 receptor and antagonist activity was not measured since it fully activated the melanocortin-4 receptor. It does not stimulate the melanocortin-4 receptor (EC$_{50}$ >100,000 nM), but the compound does block stimulation of the melanocortin-4 receptor (K$_I$ = 100 nM). The observed trends for SKY4-48-18 and SKY4-48-42 are the similar to SKY6-24-2, albeit with slightly varying concentrations. It is concluded from these in vitro results the compounds SKY6-24-2, SKY4-48-18, and SKY4-48-42 are potent stimulators (agonists) of the melanocortin-3 receptor and effective blockers (antagonists) of the melanocortin-4 receptor. SKY5-122-1 does not stimulate the melanocortin-3 receptor (EC$_{50}$ >100,000 nM) but is able to effectively block activation of the receptor (K$_I$ = 63 nM). There is slight stimulation observed for the melanocortin-4 receptor (42% stimulation at 100 μM relative to maximum possible stimulation) which is negligible. For reference, the compound SKY6-24-2 is several thousand fold more potent at stimulating the melanocortin-3 receptor than the compound SKY5-122-1 is at stimulating the melanocortin-4 receptor. SKY5-122-1 does not block activation of the melanocortin-4 receptor. The observed trends for SKY5-122-2 are similar to SKY5-122-1, again with the caveat that the absolute values are slightly different. It is concluded from these in vitro results the compounds SKY5-122-1 and SKY5-122-2 are selective and potent blockers (antagonists) of the melanocortin-3 receptor and minimally interact with the MC4R. Both types of pharmacology described above are, to the best of the inventor's knowledge, the only examples of small, amino acid based, melanocortin ligands which display these types of pharmacology.

TABLE 9A

| P1 | P2 | P3 | P4 | |
|---|---|---|---|---|
| LHis | LArg | D(pI)Phe | LTic | |
| LArg | LGln | D(pCl)Phe | DTic | 5 |
| LVal | | | LCha | |
| | | | DPro | |

TABLE 9B

| Compound ID | Sequence |
|---|---|
| 1 | Ac-LHis-LArg-D(pI)Phe-LTic-NH$_2$ (SEQ ID NO: 3) |
| 2 | Ac-LHis-LArg-D(pI)Phe-DTic-NH$_2$ (SEQ ID NO: 63) |
| 3 | Ac-LHis-LArg-D(pI)Phe-LCha-NH$_2$ (SEQ ID NO: 64) |
| 4 | Ac-LHis-LArg-D(pI)Phe-DPro-NH$_2$ (SEQ ID NO: 65) |
| 5 | Ac-LHis-LArg-D(pCl)Phe-LTic-NH$_2$ (SEQ ID NO: 66) |
| 6 | Ac-LHis-LArg-D(pCl)Phe-DTic-NH$_2$ (SEQ ID NO: 67) |
| 7 | Ac-LHis-LArg-D(pCl)Phe-LCha-NH$_2$ (SEQ ID NO: 68) |
| 8 | Ac-LHis-LArg-D(pCl)Phe-DPro-NH$_2$ (SEQ ID NO: 69) |
| 9 | Ac-LHis-LGln-D(pI)Phe-LTic-NH$_2$ (SEQ ID NO: 70) |
| 10 | Ac-LHis-LGln-D(pI)Phe-DTic-NH$_2$ (SEQ ID NO: 71) |
| 11 | Ac-LHis-LGln-D(pI)Phe-LCha-NH$_2$ (SEQ ID NO: 72) |
| 12 | Ac-LHis-LGln-D(pI)Phe-DPro-NH$_2$ (SEQ ID NO: 73) |
| 13 | Ac-LHis-LGln-D(pCl)Phe-LTic-NH$_2$ (SEQ ID NO: 74) |
| 14 | Ac-LHis-LGln-D(pCl)Phe-DTic-NH$_2$ (SEQ ID NO: 75) |
| 15 | Ac-LHis-LGln-D(pCl)Phe-LCha-NH$_2$ (SEQ ID NO: 76) |
| 16 | Ac-LHis-LGln-D(pCl)Phe-DPro-NH$_2$ (SEQ ID NO: 77) |
| 17 | Ac-LArg-LArg-D(pI)Phe-LTic-NH$_2$ (SEQ ID NO: 20) |
| 18 | Ac-LArg-LArg-D(pI)Phe-DTic-NH$_2$ (SEQ ID NO: 78) |
| 19 | Ac-LArg-LArg-D(pI)Phe-LCha-NH$_2$ (SEQ ID NO: 79) |
| 20 | Ac-LArg-LArg-D(pI)Phe-DPro-NH$_2$ (SEQ ID NO: 80) |
| 21 | Ac-LArg-LArg-D(pCl)Phe-LTic-NH$_2$ (SEQ ID NO: 81) |
| 22 | Ac-LArg-LArg-D(pCl)Phe-DTic-NH$_2$ (SEQ ID NO: 82) |
| 23 | Ac-LArg-LArg-D(pCl)Phe-LCha-NH$_2$ (SEQ ID NO: 83) |
| 24 | Ac-LArg-LArg-D(pCl)Phe-DPro-NH$_2$ (SEQ ID NO: 84) |
| 25 | Ac-LArg-LGln-D(pI)Phe-LTic-NH$_2$ (SEQ ID NO: 85) |
| 26 | Ac-LArg-LGln-D(pI)Phe-DTic-NH$_2$ (SEQ ID NO: 86) |
| 27 | Ac-LArg-LGln-D(pI)Phe-LCha-NH$_2$ (SEQ ID NO: 87) |
| 28 | Ac-LArg-LGln-D(pI)Phe-DPro-NH$_2$ (SEQ ID NO: 88) |
| 29 | Ac-LArg-LGln-D(pCl)Phe-LTic-NH$_2$ (SEQ ID NO: 89) |
| 30 | Ac-LArg-LGln-D(pCl)Phe-DTic-NH$_2$ (SEQ ID NO: 90) |
| 31 | Ac-LArg-LGln-D(pCl)Phe-LCha-NH$_2$ (SEQ ID NO: 91) |
| 32 | Ac-LArg-LGln-D(pCl)Phe-DPro-NH$_2$ (SEQ ID NO: 92) |
| 33 | Ac-LVal-LArg-D(pI)Phe-LTic-NH$_2$ (SEQ ID NO: 93) |

TABLE 9B-continued

| Compound ID | Sequence |
|---|---|
| 34 | Ac-LVal-LArg-D(pI)Phe-DTic-NH$_2$ (SEQ ID NO: 94) |
| 35 | Ac-LVal-LArg-D(pI)Phe-LCha-NH$_2$ (SEQ ID NO: 95) |
| 36 | Ac-LVal-LArg-D(pI)Phe-DPro-NH$_2$ (SEQ ID NO: 96) |
| 37 | Ac-LVal-LArg-D(pCl)Phe-LTic-NH$_2$ (SEQ ID NO: 97) |
| 38 | Ac-LVal-LArg-D(pCl)Phe-DTic-NH$_2$ (SEQ ID NO: 98) |
| 39 | Ac-LVal-LArg-D(pCl)Phe-LCha-NH$_2$ (SEQ ID NO: 99) |
| 40 | Ac-LVal-LArg-D(pCl)Phe-DPro-NH$_2$ (SEQ ID NO: 100) |
| 41 | Ac-LVal-LGln-D(pI)Phe-LTic-NH$_2$ (SEQ ID NO: 101) |
| 42 | Ac-LVal-LGln-D(pI)Phe-DTic-NH$_2$ (SEQ ID NO: 102) |
| 43 | Ac-LVal-LGln-D(pI)Phe-LCha-NH$_2$ (SEQ ID NO: 103) |
| 44 | Ac-LVal-LGln-D(pI)Phe-DPro-NH$_2$ (SEQ ID NO: 104) |
| 45 | Ac-LVal-LGln-D(pCl)Phe-LTic-NH$_2$ (SEQ ID NO: 105) |
| 46 | Ac-LVal-LGln-D(pCl)Phe-DTic-NH$_2$ (SEQ ID NO: 106) |
| 47 | Ac-LVal-LGln-D(pCl)Phe-LCha-NH$_2$ (SEQ ID NO: 107) |
| 48 | Ac-LVal-LGln-D(pCl)Phe-DPro-NH$_2$ (SEQ ID NO: 108) |

Tables 9A-B. Deconvolution for mMC3R. Table 9A shows the possible amino acids that were used at each position (P1, P2, P3 and P4) to generate the compounds shown in Table 9B. The amino acid positions are numbered in order, starting with P1 at the N-terminus.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

---

What is claimed is:

1. A compound of formula (I):

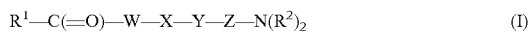

wherein
- $R^1$ is H, ($C_1$-$C_6$)cycloalkyl or ($C_1$-$C_4$)alkyl, optionally substituted with cycloalkyl;
- each $R^2$ is independently H or ($C_1$-$C_6$)alkyl;
- W is an amino acid;
- X is L-arginine or L-glutamine and Y is D-phenylalanine, wherein the phenyl ring is substituted with one or more halo groups and the phenyl ring is further optionally substituted with one or more ($C_1$-$C_4$) alkyl, —O($C_1$-$C_4$)alkyl, ($C_1$-$C_4$)haloalkyl, or —O($C_1$-$C_4$)haloalkyl; or X is L-phenylalanine, wherein the phenyl ring is substituted with one or more halo groups and the phenyl ring is further optionally substituted with one or more ($C_1$-$C_4$) alkyl, —O($C_1$-$C_4$)alkyl, ($C_1$-$C_4$)haloalkyl, or —O($C_1$-$C_4$)haloalkyl, and Y is D-arginine or D-glutamine; and
- Z is an amino acid;

or a salt thereof.

2. A compound of claim 1, which is a compound of formula (Ia):

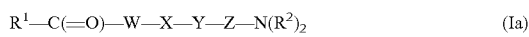

wherein X is L-arginine or L-glutamine and Y is D-phenylalanine, wherein the phenyl ring is substituted with one or more halo groups and the phenyl ring is further optionally substituted with one or more ($C_1$-$C_4$)alkyl, —O($C_1$-$C_4$)alkyl, ($C_1$-$C_4$)haloalkyl, or —O($C_1$-$C_4$)haloalkyl;

or a salt thereof.

3. The compound of claim 2, wherein X is L-arginine and Y is D-phenylalanine, wherein the phenyl ring is substituted with one or more halo groups.

4. The compound of claim 2, wherein X is L-glutamine and Y is D-phenylalanine, wherein the phenyl ring is substituted with one or more halo groups.

5. A compound of claim 1, which is a compound of formula (Ib):

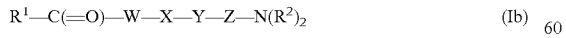

wherein X is L-phenylalanine, wherein the phenyl ring is substituted with one or more halo groups and the phenyl ring is further optionally substituted with one or more ($C_1$-$C_4$)alkyl, —O($C_1$-$C_4$)alkyl, ($C_1$-$C_4$)haloalkyl, or —O($C_1$-$C_4$)haloalkyl, and Y is D-arginine or D-glutamine;

or a salt thereof.

6. The compound of claim 5, wherein X is L-phenylalanine, wherein the phenyl ring is substituted with one or more halo groups, and Y is D-arginine.

7. The compound of claim 1, wherein $R^1$ is H and/or each $R^2$ is H.

8. The compound of claim 1, wherein W is an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO$_2$)L-Phe, (pNO$_2$)D-Phe, 2-L-Nal, 2-D-Nal, β-Ala, ε-Aminocaproic acid, D-Met[O$_2$], L-Met[O$_2$], L-dehydPro, D-dehydPro, L-(3I)Tyr and D-(3I)Tyr.

9. The compound of claim 1, wherein W is L-His, L-Arg, D-Tic, L-Val or D-Phe.

10. The compound of claim 1, wherein Z is an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO$_2$)L-Phe, (pNO$_2$)D-Phe, 2-L-Nal, 2-D-Nal, β-Ala, ε-Aminocaproic acid, D-Met[O$_2$], L-Met[O$_2$], L-dehydPro, D-dehydPro, L-(3I)Tyr and D-(3I)Tyr.

11. The compound of claim 1, wherein Z is L-Tic, D-Tic, L-Cha, D-Pro, 2-D-Nal or D-His.

12. The compound of claim 1, selected from the group consisting of:

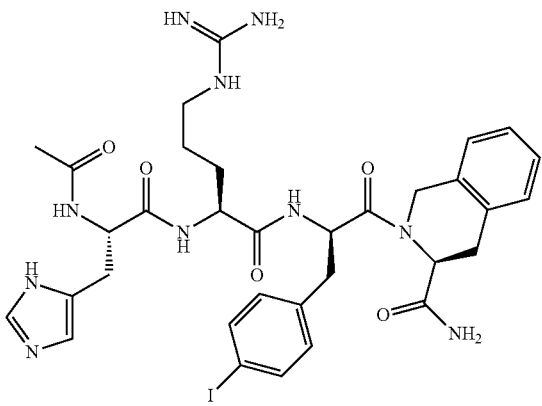

,

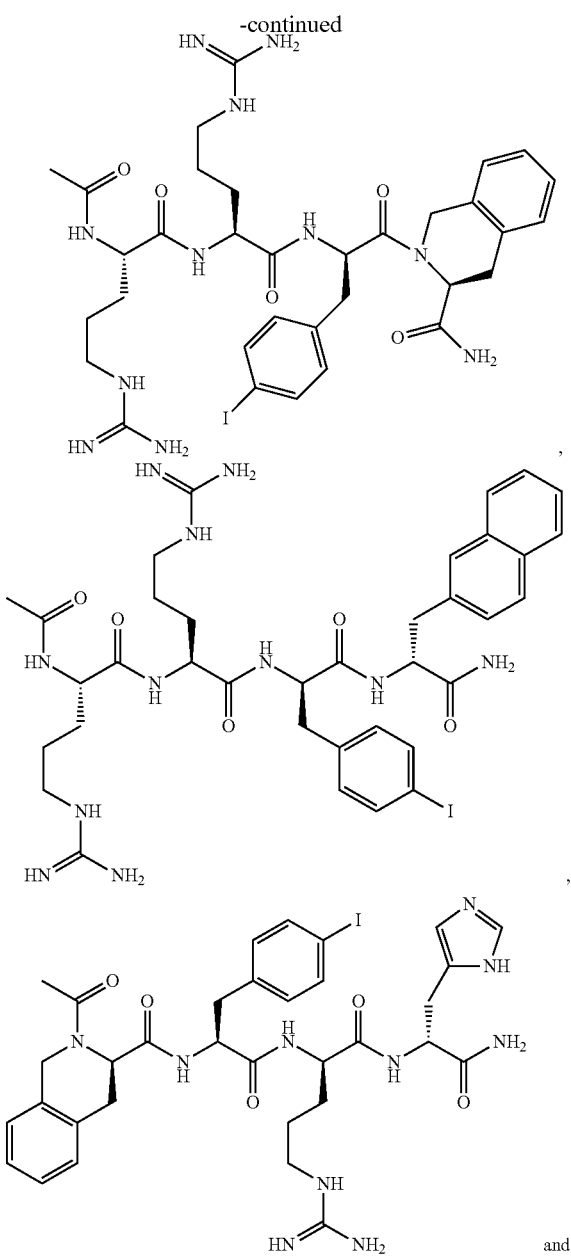

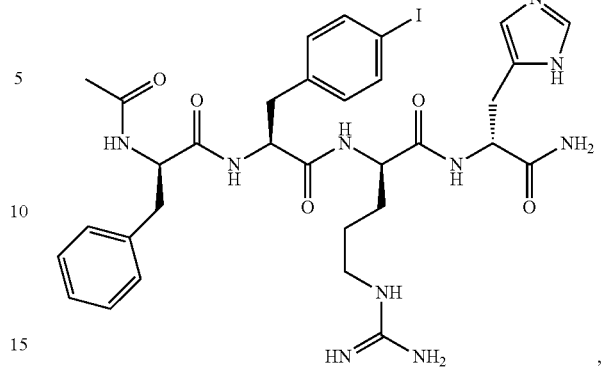

and salts thereof.

13. The compound of claim 1, which is a compound of formula (I) selected from the group consisting of SEQ ID NO. 3-50, and SEQ ID NO. 58-108.

14. The compound of claim 1, wherein the compound is a melanocortin-3 receptor (MC3R) agonist.

15. The compound of claim 1, wherein the compound is a melanocortin-4 receptor (MC4R) antagonist.

16. The compound of claim 1, wherein the compound is a melanocortin-3 receptor (MC3R) antagonist.

17. The compound of claim 1, wherein the compound is not a melanocortin-4 receptor (MC4R) antagonist or agonist.

18. A composition comprising a compound of claim 1, or a salt thereof, and a carrier.

19. A method for decreasing appetite in a mammal in need thereof, comprising administering an effective amount of a compound of claim 1, or a pharmaceutically acceptable salt thereof, to the mammal, wherein the compound is a melanocortin-3 receptor (MC3R) antagonist.

20. A method of treating obesity in a mammal in need thereof, comprising administering an effective amount of a compound of claim 1, or a pharmaceutically acceptable salt thereof, to the mammal, wherein the compound is a melanocortin-3 receptor (MC3R) antagonist.

* * * * *